(12) United States Patent
Becker et al.

(10) Patent No.: US 11,661,477 B2
(45) Date of Patent: May 30, 2023

(54) STAR-SHAPED POLY(PROPYLENE FUMARATE) COPOLYMERS FOR 3D PRINTING APPLICATIONS

(71) Applicants: Matthew L. Becker, Chapel Hill, NC (US); Gaelle Le Fer, Lille (FR)

(72) Inventors: Matthew L. Becker, Chapel Hill, NC (US); Gaelle Le Fer, Lille (FR)

(73) Assignee: THE UNIVERSITY OF AKRON, Akron, OH (US)

( * ) Notice: Subject to any disclaimer, the term of this patent is extended or adjusted under 35 U.S.C. 154(b) by 0 days.

(21) Appl. No.: 17/274,510

(22) PCT Filed: Sep. 10, 2019

(86) PCT No.: PCT/US2019/050338
§ 371 (c)(1),
(2) Date: Mar. 9, 2021

(87) PCT Pub. No.: WO2020/055816
PCT Pub. Date: Mar. 19, 2020

(65) Prior Publication Data
US 2022/0041804 A1    Feb. 10, 2022

Related U.S. Application Data

(60) Provisional application No. 62/729,126, filed on Sep. 10, 2018.

(51) Int. Cl.
*C08G 63/58* (2006.01)
*B33Y 70/00* (2020.01)
*B33Y 80/00* (2015.01)

(52) U.S. Cl.
CPC ............. *C08G 63/58* (2013.01); *B33Y 70/00* (2014.12); *B33Y 80/00* (2014.12)

(58) Field of Classification Search
CPC ........ A61L 24/046; C08L 67/06; C08G 63/58; B33Y 70/00; B33Y 80/00
See application file for complete search history.

(56) References Cited

U.S. PATENT DOCUMENTS 3,089,863 A * 5/1963 Hicks ................. C08L 63/10
528/297
4,888,413 A * 12/1989 Domb ................. A61L 24/046
525/445

(Continued)

FOREIGN PATENT DOCUMENTS

| WO | 2006055940 A2 | 5/2006 |
| WO | 2016/081587 A1 | 5/2016 |
| WO | 2018/142384 A2 | 8/2018 |

OTHER PUBLICATIONS

Frydrych et al., Polymer Degradation and Stability 132 (2016) 202-212.*

(Continued)

*Primary Examiner* — Shane Fang
(74) *Attorney, Agent, or Firm* — Renner, Kenner, Greive, Bobak, Taylor & Weber

(57) ABSTRACT

In various embodiments, the invention relates to poly(propylene fumarate) (PPF)-based star-shaped copolymers synthesized using a core-first approach that uses a multi-functional alcohols as an initiator, and $Mg(BHT)_2(THF)_2$ as catalyst for controlled ring opening copolymerization (RO-COP) of maleic anhydride (MAn) with propylene oxide (PO). In some embodiments, these star-PPF copolymers have lower viscosities than their linear analogs, allowing a decrease in DEF fraction in resin formulation, as well as the use of higher molecular weights. These star-shape PPF can be used to prepare PPF:DEF resins containing as much as 70% by weight of the multi-arm PPF star copolymers, and have a low complex viscosity of high $\overline{M_n}$ star PPF resin that (Continued)

affords rapid printing with a $\overline{M}_n$ nearly eight times larger than the largest linear PPF oligomer printed previously.

24 Claims, 21 Drawing Sheets

(56) References Cited

U.S. PATENT DOCUMENTS

| | | | |
|---|---|---|---|
| 5,733,951 | A | 3/1998 | Yaszemski et al. |
| 6,884,432 | B2 | 4/2005 | Yaszemski et al. |
| 2005/0080223 | A1* | 4/2005 | Tuominen ............... C08G 63/60 528/272 |
| 2019/0209732 | A1* | 7/2019 | Xie ..................... A61L 24/0015 |

OTHER PUBLICATIONS

Cai, et al., Poly(propylene fumarate)-based materials: Synthesis, functionalization properties, device fabrication and biomedical applications, Mar. 28, 2019, Biomaterials 208 (2019) 4571.

"Modern Materials Science and Engineering Dictionary", Hengde Li, Shandong Science and Technology Press, p. 550, Aug. 2001.

Extended European Search Report and Search Opinion, for EP 19 85 9993, dated May 4, 2022.

\* cited by examiner

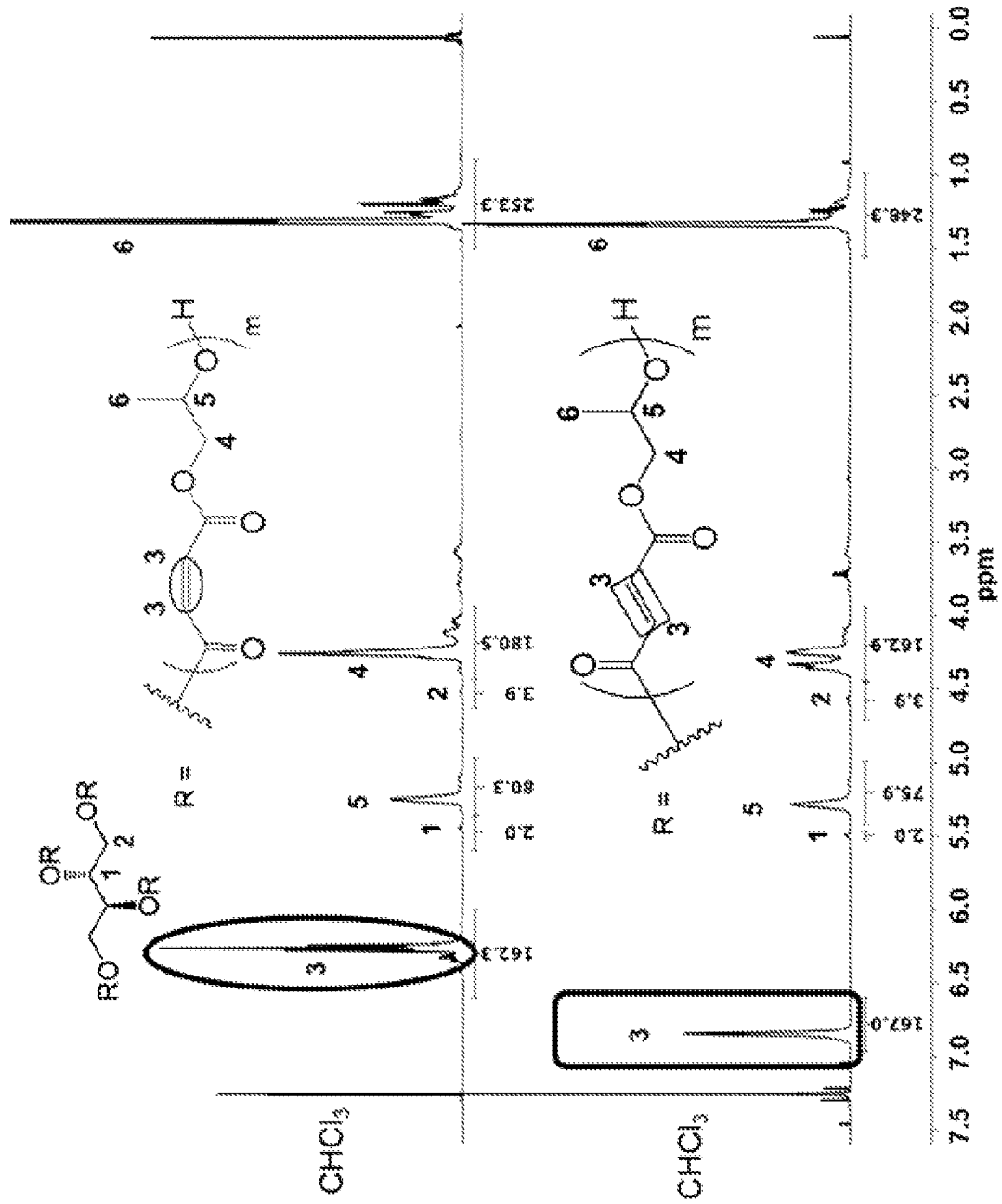
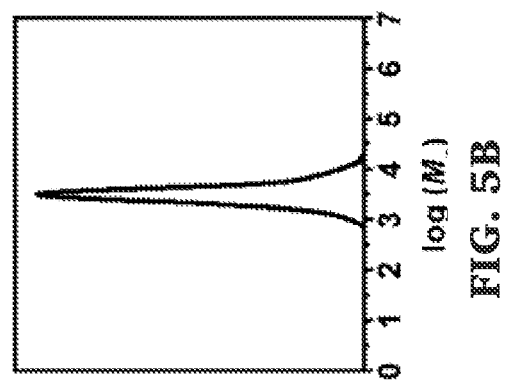
FIG. 5A
FIG. 5B

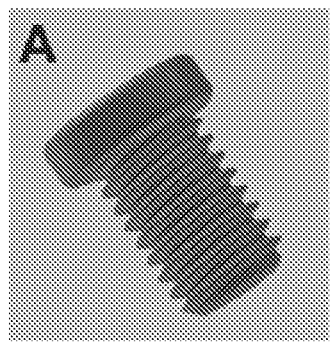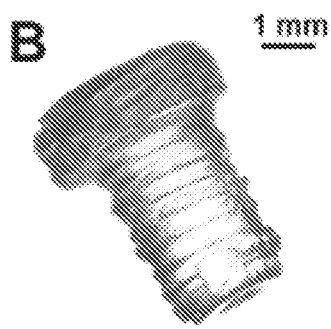
FIG. 16A   FIG. 16B
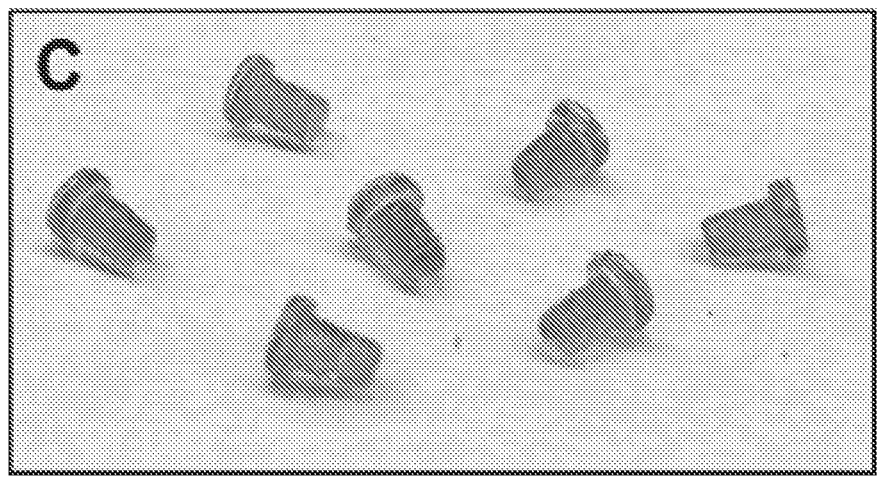
FIG. 16C

STAR-SHAPED POLY(PROPYLENE FUMARATE) COPOLYMERS FOR 3D PRINTING APPLICATIONS

CROSS REFERENCE TO RELATED APPLICATIONS

This application claims the benefit of International application No. PCT/US2019/050338 entitled "Star-Shaped Poly (Propylene Fumarate) Copolymers for 3D Printing Applications," filed Sep. 10, 2019, which claims the benefit of U.S. provisional patent application Ser. No. 62/729,126 entitled "Star-Shaped Poly(Propylene Fumarate) Copolymers for 3D Printing Applications," filed Sep. 10, 2018. Both of these applications are incorporated herein by reference in its entirety.

NAMES OF THE PARTIES TO A JOINT RESEARCH AGREEMENT

The present application stems from work done pursuant to a Joint Research Agreement between The University of Akron of Akron, Ohio and 3D BioActives, LLC of Akron, Ohio.

FIELD OF THE INVENTION

One or more embodiments of the present invention report the elaboration of copolymers involving in the preparation of 3D printable resins for use in biomedical applications. In certain embodiments, the present invention describes the synthesis of star-shaped poly(propylene fumarate) (PPF) copolymers. In other embodiments, the present invention reports the use of these star-shaped PPF copolymers for the preparation of resins that have a viscosity in a three-dimensional (3D) printable viscosity range.

BACKGROUND OF THE INVENTION

Progress in additive manufacturing, also known as three-dimensional (3D) printing, has the potential to revolutionize the way surgeons address complicated reconstructive efforts in many surgical specialties, including such things as oral, maxillofacial, and/or orthopedic trauma, cancer defect repairs, pathogenesis, congenital deformity and senescence. Digital light processing (DLP), also referred to dynamic mask photolithography, is a 3D printing technique based on the selective crosslinking of a photo-sensitive resin in a layer-by-layer process using a UV and/or visible light projector. This method affords high resolution control over scaffold features such as porosity, strut and pore size and overall scaffold shape, offering significant advantages to regenerative medicine, including reproducibility or fabrication of patient specific templates. The architecture of the scaffold is of paramount importance since will directly impact its mechanical strength, degradation characteristics, and capacity to guide new tissues into a surgical defect.

Tissue engineering, especially for the treatment of large bone defects, could really be improved by the development of new resorbable 3D printed materials able to supply attractive alternatives to the autografts, allografts, ceramics, and metals that are currently used in clinical settings. Polymers are attractive materials for tissue engineering scaffolds because they may be chosen and tailored to satisfy specific requirements such as biodegradability, biocompatibility, functionality or mechanical properties. Polyester use has grown steadily in regenerative medicine partly because they exhibit various resorption rates. Saturated polyesters such as poly(s-caprolactone) (PCL), poly(lactic acid) (PLA), poly(glycolic acid) (PGA), poly(lactic-co-glycolic acid) (PLGA) or vinyl polyester, have been utilized in applications including suture, drug delivery systems, imaging systems combining biomaterials and contrast agents, and scaffolds for tissue engineering. Nevertheless, the lack of reactive groups along the backbone limits their post-polymerization and post-printing functionalization and their applicability for stereolithography (SLA).

Poly(propylene fumarate) (PPF), an unsaturated polyester used in a number of medical applications such as controlled drug release, and tissue engineering, has already shown remarkable properties in the fabrication of medical devices and 3D tissue scaffolds using SLA methods, such as cDLP or in liquid crystal display-based printing. The chains can be photo-crosslinked through the alkenes to produce reliable, high-fidelity solid-cured polymer scaffolds with complex geometric designs. Indeed, its carbon-carbon double bonds can be involved in a photo-crosslinking reaction to produce reliable, high-fidelity solid-cured polymer scaffolds with complex geometric designs coupled with very fine (<50 µm) features. PPF presents numerous benefits including its resorption timescale, within a window identified to more closely match new tissue growth than PLA or PCL. PPF degrades via hydrolysis of the ester bonds into a Krebs-cycle constituent (fumaric acid) and propylene glycol, two non-toxic products that are cleared by normal metabolic processes.

PPF was synthesized for the first time in 1994 by Mikos and co-workers (See, e.g., U.S. Pat. No. 5,733,951) via step-growth polycondensation of diethyl fumarate (DEF) and propylene glycol. However, this synthetic method is difficult to control at low molar mass ($\overline{M}_n$), and results in broad molar mass distribution ($Ð_m$), poor end-group fidelity, all of which influence the properties of the final material. Another method using ring-opening copolymerization (RO-COP) of maleic anhydride (MA) and propylene oxide (PO) in the presence of a cobalt catalyst to yield well-defined poly(propylene maleate) (PPM) that could be converted to PPF upon isomerization was introduced by Coates and co-workers (See, A. M. DiCiccio and G. W. Coates, *Journal of the American Chemical Society*, 2011, 133, 10724-10727). These methods were significantly limited for medical and biological applications by the toxicity of the cobalt catalyst, among other things. More recently, the toxicity of cobalt has been addressed by the use of magnesium ethoxide catalyst (Y. Luo, C. K. Dolder, J. M. Walker, R. Mishra, D. Dean and M. L. Becker, Biomacromolecules, 2016, 17, 690-697). PPF with high end-group fidelity has since been developed using magnesium 2,6-di-tert-butyl phenoxide (Mg(BHT)2(THF)2) catalyst and functionalized primary alcohol initiator. See, J A Wilson, A P Kleinfehn, D Luong, S Sallam, C Wesdemiotis, M L Becker, "Magnesium catalyzed polymerization of end functionalized poly(propylene maleate) and poly(propylene fumarate) for 3D Printing" J. Amer. Chem. Soc. 2018, 140(1), 277-284, the disclosure of which is incorporated herein by reference in its entirety.) This result provided a route to expand the diversity of PPF-based copolymers such as poly(lactone)-block-polypropylene fumarate) (See, e.g., S. R. Petersen, J. A. Wilson and M. L. Becker, *Macromolecules*, 2018, 51, 6202-6208, the disclosure of which is incorporated herein by reference in its entirety) or poly(ethylene glycol)-block-poly(propylene fumarate) (PEG-b-PPM) (See, e.g., R. A. Dilla, C. M. Motta, S. R. Snyder, J. A. Wilson, C. Wesdemiotis and M. L. Becker, *ACS Macro Letters*, 2018, 7, 1254-1260, the disclosure of which is incorporated herein by reference in its entirety), via sequential ROP/ROCOP method and PEG macroinitiator, respectively.

Nevertheless, the viscosity of linear PPF (higher than 25 Pa·s at 40° C.) requires, so far, a fifty percent dilution in the reactive diluent diethyl fumarate (DEF) to reduce its viscosity and make possible the 3D printing. Moreover, during the photo-crosslinking process, the DEF is incorporated into the network and can affect the mechanical properties of the 3D printed scaffold and lead to low elastic modulus and fracture strength values, non-suitable for bone regeneration.

To date, however, there has been great difficulty developing a PPF resin having the polymer resin properties required for cDLP 3D printing, while ensuring that the resulting scaffolds possess the optimal biological and mechanical properties. Low viscosities, typically between 0.25 Pa·s and 10 Pa·s are required for rapid printing to accommodate the need for a new layer of liquid resin to flow into the small gap between the surface of the resin tray and the previous cured solid layer supported by the platform and to maintain dispersion of resin additives. The zero-shear viscosity at 40° C. of pure linear PPF (e.g. for a $\overline{M_n}$=1.5 kDa, $Đ_m$=1.7 PPF oligomer) is 2370 Pa·s. Accordingly, reaching a suitable printing viscosity typically requires significant dilution (50 wt. %) in diethyl fumarate (DEF) to avoid printing failures, and long curing times to facilitate layer thickness control. Because the viscosity of linear PPF is closely related to its degree of polymerization, short PPF oligomers in a 0.7-3.5 kDa molar mass range are required, which limits the exploration of mechanical and degradation properties of the printed materials. Indeed, the narrow molar mass ($\overline{M_n}$) range with suitable viscosity properties for printing severely limits the printing speed, the breadth of mechanical properties, and the resorption window of the scaffolds. Further, because DEF can be toxic, unreacted, residual, DEF must be removed from the cured scaffolds before their use as medical devices. By reducing the viscosity of PPF-based copolymers, the amount of DEF required to prepare the 3D printable resin could be reduced.

Branched polymers such as star polymers, cyclic polymer, dendrimers, and hyperbranched polymers are known to possess distinctive rheological and mechanical properties. In comparison with conventional linear polymers, they generally provide smaller hydrodynamic volume and consequently lower solution viscosity and less entanglement in the bulk.

What is needed in the art is a 3D printable PPF polymer having a molecular weight high enough for use in a wide range of applications but a viscosity that is lower than a comparable linear PPFs.

SUMMARY OF THE INVENTION

In various embodiments, the present invention is directed to PPF-based star-shaped copolymers and their use to prepare polymeric resins with viscosity values compatible with 3D printing applications. In one or more embodiments, the present invention is directed to synthesis of multi-arm poly(propylene fumarate) (PPF) copolymers through a core-first approach using multi-functional sugar-based alcohols such as, meso-erythritol or adonitol, as an initiator, and Mg(BHT)$_2$(THF)$_2$ as catalyst for controlled ring opening copolymerization (ROCOP) of maleic anhydride (MAn) with propylene oxide (PO). In some embodiments, the star-PPF copolymers of the present invention have lower viscosities than their linear analogs, allowing the decrease of DEF ratio in resin formulation, as well as the use of higher molecular weights. In some embodiments, the present invention relates to a four-arm poly(propylene fumarate) through a core-first approach using meso-erythritol, a sugar-based alcohol, as an initiator with total DPs in a 20-200 range corresponding to molar masses between 3.2 and 31.2 kDa and narrow, monomodal molar mass distributions ($Đ_m$=1.28-1.48). These star-shape PPF were used to prepare PPF:DEF resins with different weight ratios (50:50 wt %, 60:40 wt % and 70:30 wt %) having a low complex viscosity of high $\overline{M_n}$ star PPF resin that afforded rapid printing of PPF with a $\overline{M_n}$ nearly eight times larger than the largest linear PPF oligomer printed previously.

In a first aspect, the present invention is directed to a star-shaped copolymer having three or more poly(propylene fumarate) arms extending outward from a central core. In one or more embodiments, the central core comprises the residue of a multi-functional alcohol initiator having three or more hydroxyl functional groups. In one or more embodiments, the star-shaped copolymer of the present invention includes any one or more of the above referenced embodiments of the first aspect of the present invention wherein the each of the three or more poly(propylene fumarate) arms comprise about 50 mole percent propylene oxide residues and 50 mole percent maleic anhydride residues.

In one or more embodiments, the star-shaped copolymer of the present invention includes any one or more of the above referenced embodiments of the first aspect of the present invention having a degree of polymerization (DP) of from about 3 to about 650, preferably from about 3 to about 325, and more preferably from about 3 to about 200. In one or more embodiments, the star-shaped copolymer of the present invention includes any one or more of the above referenced embodiments of the first aspect of the present invention having a number average molecular weight ($\overline{M_n}$) of from about 0.5 kDa to about 100 kDa, preferably from about 0.5 kDa to about 50 kDa, and more preferably from about 0.5 kDa to about 25 kDa, as calculated for NMR spectroscopy or measured by one of size exclusion chromatography (SEC) and gel permeation chromatography (GPC). In one or more embodiments, the star-shaped copolymer of the present invention includes any one or more of the above referenced embodiments of the first aspect of the present invention having a molecular mass distribution ($Đ_m$) of from about 1 to about 2, preferably from about 1 to about 1.7, and more preferably from about 1 to about 1.4.

In one or more embodiments, the star-shaped copolymer of the present invention includes any one or more of the above referenced embodiments of the first aspect of the present invention having an average complex viscosity of from about 0.2 Pa·s to about 2.0 Pa·s, preferably from about 0.5 Pa·s to about 1.5 Pa·s, and more preferably from about 0.6 Pa·s to about 1.1 Pa·s, as measured by a rheometer when diluted in 50 weight percent DEF. In one or more embodiments, the star-shaped copolymer of the present invention includes any one or more of the above referenced embodiments of the first aspect of the present invention having an average complex viscosity of from about 0.5 Pa·s to about 10.0 Pa·s, preferably from about 0.8 Pa·s to about 6 Pa·s, and more preferably from about 1.0 Pa·s to about 1.1 Pa·s, as measured by a rheometer when diluted in 40 weight percent DEF. In one or more embodiments, the star-shaped copolymer of the present invention includes any one or more of the above referenced embodiments of the first aspect of the present invention having an average complex viscosity of from about 2 Pa·s to about 30 Pa·s, preferably from about 5

Pa·s to about 25 Pa·s, and more preferably from about 8 Pa·s to about 10 Pa·s, as measured by a rheometer when diluted in 30 weight percent DEF.

In one or more embodiments, the star-shaped copolymer of the present invention includes any one or more of the above referenced embodiments of the first aspect of the present invention having an absorbance at wavelengths from about 305 nm to about 405 nm of from about 0.001 to about 0.3, preferably from about 0.001 to about 0.2, and more preferably from about 0.001 to about 0.1, as measured by a UV-Visible spectrometer.

In one or more embodiments, the star-shaped copolymer of the present invention includes any one or more of the above referenced embodiments of the first aspect of the present invention having the formula:

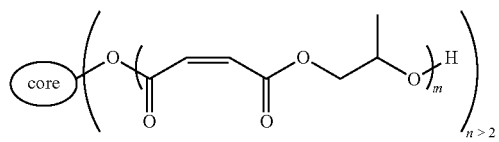

where m is an integer from about 1 to about 200, n is a number of arms greater than 2 and the core comprises the residue of a multi-functional alcohol initiator.

In a second aspect, the present invention is directed to a star-shaped copolymer for use in 3D printable resins comprising the isomerized reaction product of maleic anhydride propylene oxide and a multi-functional alcohol initiator having three or more hydroxyl functional groups. In some embodiments, the star-shaped copolymer comprises about 50 mole percent propylene oxide residues. In one or more embodiments, the star-shaped copolymer of the present invention includes any one or more of the above referenced embodiments of the second aspect of the present invention having a degree of polymerization (DP) of from about 3 to about 650, preferably from about 3 to about 325, and more preferably from about 3 to about 200. In some embodiments, the star-shaped copolymer of the present invention includes any one or more of the above referenced embodiments of the second aspect of the present invention having a number average molecular weight ($\overline{M_n}$) of from about 0.5 kDa to about 100 kDa, preferably from about 0.5 kDa to about 50 kDa, and more preferably from about 0.5 kDa to about 25 kDa, as calculated for NMR spectroscopy or measured by size exclusion chromatography (SEC) or gel permeation chromatography (GPC).

In one or more embodiments, the star-shaped copolymer of the present invention includes any one or more of the above referenced embodiments of the second aspect of the present invention having a molecular mass distribution ($Đ_m$) of from about 1 to about 2, preferably from about 1 to about 1.7, and more preferably from about 1 to about 1.4. In one or more embodiments, the star-shaped copolymer of the present invention includes any one or more of the above referenced embodiments of the second aspect of the present invention having an average complex viscosity of from about 0.2 Pa·s to about 2.0 Pa·s, preferably from about 0.5 Pa·s to about 1.5 Pa·s, and more preferably from about 0.6 Pa·s to about 1.1 Pa·s, as measured by a rheometer when diluted in 50 weight percent DEF. In some embodiments, the star-shaped copolymer of the present invention includes any one or more of the above referenced embodiments of the second aspect of the present invention having an average complex viscosity of from about 0.5 Pa·s to about 10.0 Pa·s, preferably from about 0.8 Pa·s to about 6 Pa·s, and more preferably from about 1.0 Pa·s to about 1.1 Pa·s, as measured by a rheometer when diluted in 40 weight percent DEF. In one or more embodiments, the star-shaped copolymer of the present invention includes any one or more of the above referenced embodiments of the second aspect of the present invention having an average complex viscosity of from about 2 Pa·s to about 30 Pa·s, preferably from about 5 Pa·s to about 25 Pa·s, and more preferably from about 8 Pa·s to about 10 Pa·s, as measured by a rheometer when diluted in 30 weight percent DEF.

The star-shaped copolymer for use in 3D printable resins of claim 12 having an absorbance at wavelengths from about 305 nm to about 405 nm of from about 0.001 to about 0.3, preferably from about 0.001 to about 0.2, and more preferably from about 0.001 to about 0.1, as measured by a UV-Visible spectrometer.

The star-shaped copolymer of claim 12 having the formula:

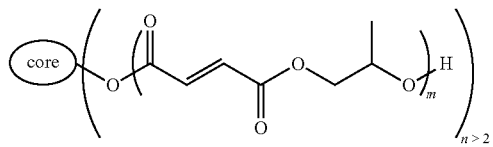

where m is an integer from about 1 to about 200, n is a number of arms greater than 2 and the core comprises the residue of a multi-functional alcohol initiator.

In a third aspect, the present invention relates to a method of making a polymer for use in 3D printable resins comprising: reacting maleic anhydride, and propylene oxide and a multifunctionalized initiator in the presence of a magnesium catalyst to form a star-shaped poly(propylene maleate) copolymer intermediate having a maleic anhydride residue containing a cis double bond; and isomerizing the cis double bond in the maleic anhydride residue by reacting the star-shaped poly(propylene maleate) copolymer intermediate with an organic base catalyst to form a star-shaped poly(propylene fumarate) copolymer with trans double bonds. In some embodiments, the method further comprises: washing the solution with a sodium phosphate aqueous solution to remove any residual amine; and drying the product to recover the star-shaped poly(propylene fumarate) copolymer.

In some embodiments, the method of the present invention includes any one or more of the above referenced embodiments of the third aspect of the present invention wherein the multifunctionalized initiator is a molecule bearing 3 or more functional groups capable of initiating copolymerization of maleic anhydride (MAn) monomer and propylene oxide (PO) monomer. In one or more embodiments, the method of the present invention includes any one or more of the above referenced embodiments of the third aspect of the present invention wherein the multifunctionalized initiator is a multifunctionalized alcohol initiator having 3 or more hydroxyl functional groups capable of initiating copolymerization of maleic anhydride (MAn) monomer and propylene oxide (PO) monomer. In some of these embodiments, multifunctionalized initiator is meso-erythritol or adonitol. In some embodiments, the method of the present invention includes any one or more of the above referenced embodiments of the third aspect of the present invention wherein the magnesium catalyst is $Mg(BHT)_2(THF)_2$.

In one or more embodiments, the method of the present invention includes any one or more of the above referenced embodiments of the third aspect of the present invention wherein the step of reacting comprises: placing a multifunctonalized initiating alcohol and $Mg(BHT)_2(THF)_2$ in a suitable sealed reaction vessel and then adding propylene oxide, maleic anhydride and a suitable solvent; heating the combination until substantially all of the maleic anhydride, and propylene oxide have reacted to form a star-shaped poly (propylene maleate) copolymer intermediate; precipitating the star-shaped poly(propylene maleate) copolymer intermediate into an excess of a non-solvent for the star-shaped poly(propylene maleate) copolymer intermediate; and drying the star-shaped poly(propylene maleate) copolymer intermediate to remove remaining solvent. In one or more embodiments, the method of the present invention includes any one or more of the above referenced embodiments of the third aspect of the present invention wherein the suitable solvent in the step of combing is selected from toluene, hexane, and combinations thereof.

In one or more embodiments, the method of the present invention includes any one or more of the above referenced embodiments of the third aspect of the present invention wherein the step of heating comprises heating the combination to a temperature of from about 40° C. to about 80° C. for from about 1 hour to about 48 hours or until substantially all of the maleic anhydride, and propylene oxide monomers have reacted. In one or more embodiments, the method of the present invention includes any one or more of the above referenced embodiments of the third aspect of the present invention the step of precipitating comprises combing the product with an excess of diethyl ether to cause the star-shaped poly(propylene maleate) copolymer intermediate to precipitate out of solution. In one or more embodiments, the method of the present invention includes any one or more of the above referenced embodiments of the third aspect of the present invention wherein the step of drying is performed by vacuum evaporation.

In one or more embodiments, the method of the present invention includes any one or more of the above referenced embodiments of the third aspect of the present invention wherein the step of isomerizing comprises: dissolving the star-shaped poly(propylene maleate) copolymer intermediate in a suitable solvent; and adding diethylamine or piperidine, to the solution and heating it to a reflux temperature under an inert atmosphere to produce the star-shaped poly (propylene fumarate) copolymer. In some embodiments, the method of the present invention includes any one or more of the above referenced embodiments of the third aspect of the present invention wherein the suitable solvent for the star-shaped poly(propylene maleate) copolymer intermediate is selected from the group consisting of chloroform, dichloromethane, and combinations thereof. In one or more embodiments, the method of the present invention includes any one or more of the above referenced embodiments of the third aspect of the present invention wherein the solution is heated to a reflux temperature under an inert atmosphere for from about 1 to about 48 hours or until substantially all of star-shaped poly(propylene maleate) copolymer intermediate has isomerized. In one or more embodiments, the method of the present invention includes any one or more of the above referenced embodiments of the third aspect of the present invention wherein the buffer solution in the step of washing is a sodium phosphate aqueous solution. In one or more embodiments, the method of the present invention includes any one or more of the above referenced embodiments of the third aspect of the present invention wherein the step of drying is performed by vacuum evaporation.

In a fourth aspect, the present invention is directed to a polymer resin for use in 3D printing comprising the star-shaped copolymer described above. In one or more embodiments, polymer resin for use in 3D printing will comprise from about 50 wt % to about 70 wt % of said polymer resin. In a fifth aspect, the present invention is directed to a 3D printed polymer structure formed from the 3D printable star PPF polymer resin.

BRIEF DESCRIPTION OF THE DRAWINGS

For a more complete understanding of the features and advantages of the present invention, reference is now made to the detailed description of the invention along with the accompanying figures in which:

FIGS. 5A-B are a comparison of $^1H$ NMR spectra of four-arm star poly(propylene maleate) of a total DP80 with a meso-erythritol core (top) and corresponding four-arm star poly(propylene fumarate) obtained after isomerization (bottom) (FIG. 5A) and a size exclusion chromatography profile of four-arm star poly(propylene maleate) of a total DP80 with a meso-erythritol core (FIG. 5B).

FIGS. 15A and 15C are images of a CAD model of a gyroidal scaffold that was created in Matlab using the Schoen gyroid triply periodic minimal surface with 136 μm strut size, 475 μm pore size, and 88.2% porosity. FIG. 15B is an optical microscopy image and FIG. 15D a μ-CT image of a 3D printed gyroidal scaffold (8 mm×4 mm, porosity: 87.6%, strut size: 130.9±9.3 μm, pore size: 442 μm).

FIGS. 16A-C are CAD model of a screw with 4.5 mm height (FIG. 16A), an optical microscopy image of a 3D printed screw (FIG. 16B), and a picture of several of the 3D printed screws (FIG. 16C).

DETAILED DESCRIPTION OF THE ILLUSTRATIVE EMBODIMENTS

Figure 1:
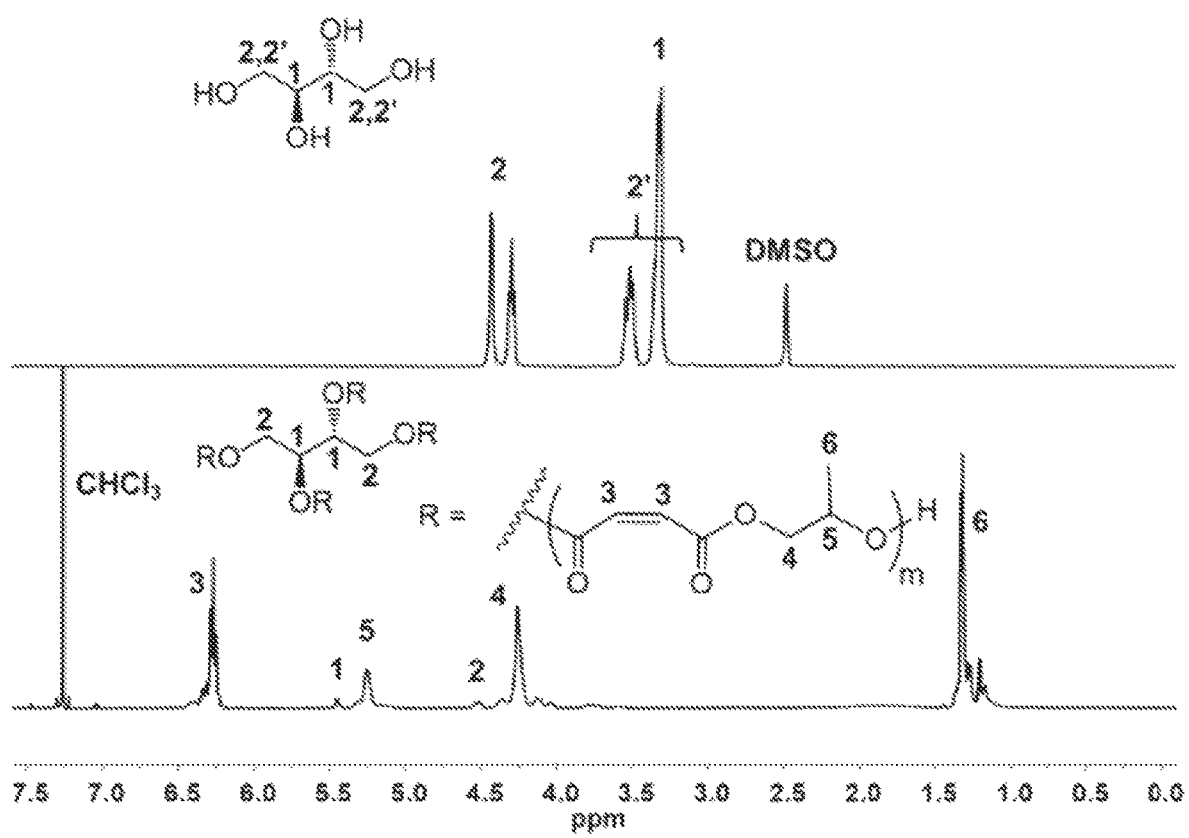
FIG. 1 is a comparison of the $^1H$ NMR spectrum of meso-erythritol (500 MHz, 303 K, DMSO-$d_6$) (upper) and the $^1H$ NMR spectrum of four-arm star-shaped PPM DP 40 with a meso-erythritol core (500 MHz, 303 K, $CDCl_3$) (lower).

As set forth above, additive manufacturing is changing tissue engineering by offering pathways to otherwise unattainable, highly complex scaffold morphologies. Linear poly (propylene fumarate) (PPF) oligomers have demonstrated remarkable properties for 3D printing of porous gyroid scaffolds using continuous digital light processing (cDLP). Nevertheless, the narrow molar mass ($\overline{M}_n$) range with suitable viscosity properties for printing of these linear poly (propylene fumarate) (PPF) oligomers severely limits the printing speed of these resins, the breadth of mechanical properties of the printed polymers, and the resorption window of the scaffolds.

In various embodiments, the present invention is directed to star shaped PPF-based copolymers for 3D printing applications and methods for their making and use that address these issues. These copolymers can be used in the preparation of resins that have a viscosity in a printable viscosity range and allow light transmittance at curing wavelengths. Viscosity is closely related to degree of polymerization and stoichiometry of the monomers, so the degree of polymerization and molecular weight distribution of PPF-based copolymer must be carefully controlled. In various embodiments, these star-shaped PPF copolymers were synthesized through a core-first approach using a multi-functionalized alcohol as initiator, i.e. meso-erythritol, or adonitol, and Mg(BHT)$_2$(THF)$_2$ as catalyst for controlled ROCOP of maleic anhydride (MAn) with propylene oxide (PO). Initiation by meso-erythritol led to 4-arm star-shaped copolymers while initiation by adonitol led to 5-arm star-shaped copolymers. These star copolymers have defined molecular weight and molecular weight distribution. In various embodiments, multi-arm PPF copolymers of the present invention will have a lower viscosity than a corresponding linear PPF of the same or comparable molecular weight. As a result, the multi-arm PPF copolymers of the present invention require less diethyl fumarate (DEF) to prepare a resin having a viscosity suitable for 3D printing on conventional 3D printers (generally from about 0.1 Pa·s to about 5.0 Pa·s). Moreover, because of its relatively low viscosity at higher molecular weights, the multi-arm PPF copolymers of the present invention may be used to prepare 3D printed scaffolds having a high molecular weight PPF structure that is not possible with currently available linear PPF polymers. In fact, in some embodiments, printable resins based on the star PPF polymers of the present invention showed complex viscosity that decreased as the total $\overline{M}_n$ increased, allowing rapid printing of PPF with $\overline{M}_n$ nearly eight times larger than the largest linear PPF oligomer printed previously.

In a one aspect, the present invention is directed to star-shaped PPF-based 3D printable copolymer having from 3 to about 6 PPF arms connected to and extending outward from a central core. In the context of a polymer or copolymer, the terms "star polymer," "star-shaped," and "multi-arm" are used herein interchangeably to refer to a polymer or co polymer having 3 or more arms extending outward from a central core. As used herein, the term "arm" refers to a substantially linear polymer or copolymer chain that is bonded at one end to a central core and extends outward therefrom. As follows from this, the term "PPF arm" is used herein to refer to an arm, as defined above, comprising PPF and the term "PPM arm" is used herein to refer to an arm comprising PPM. As used herein, the term "3D printable," as applied to a polymer or copolymer, refers to a polymer or copolymer that can be used alone or with other ingredients such as diethyl fumarate (DEF), crosslinkers, diluents, photoinitiators, dyes, light attenuating agents, dispersants, emulsifiers, ceramics, BIOGLASS™, hydroxyapatite, β-tricalcium phosphate, and/or solvents to form a resin capable of be printed into a 3 dimensional structure using conventional additive manufacturing (3D printing) technologies.

In various embodiments, these star-shaped PPF-based co polymers of the present invention may have 3, 4, 5, or six arms. While the star-shaped PPF-based 3D printable copolymers of the present invention may in some embodiments have more than 6 arms, this is not preferred as it may create additional difficulties with crosslinking the polymer. In some embodiments, the star-shaped PPF-based co polymers of the present invention will have 3 arms. In other embodiments, the star-shaped PPF-based co polymers of the present invention will have 4 arms. In still other embodiments, the star-shaped PPF-based co polymers of the present invention will have 5 arms.

As will be apparent, the central core of the star-shaped PPF-based 3D printable copolymers of the present invention will comprise the residue of the multi-functional alcohol used to as the initiator and the number of arms on these polymers is likewise controlled by the number of alcohol (i.e. hydroxyl) functional groups present on the multi-functional alcohol initiator. As used herein, the term "residue(s)" is used to refer generally to the portion of a monomer or other chemical unit that has been incorporated into a polymer or other large molecule. By way of example, in one or more embodiments, the terms "4-arm star" and "4-arm star-shaped" are used to refer to PPF copolymers with 4 arms derived from the ROCOP of MAn with PO initiated by an alcohol having four available hydroxyl groups, such as meso-erythritol, with each of the four hydroxyl groups initiating ROCOP of one arm of the 4-arm star polymer and the remainder of the alcohol molecule forming the core. Similarly, the terms "5-arm star" and "5-arm star-shaped" refer to PPF copolymers with 5 arms derived from the ROCOP of MAn with PO initiated by an alcohol having five available hydroxyl groups, such as adonitol, with each of the five hydroxyl groups initiating ROCOP of one arm of the 5-arm star polymer and the remainder of the alcohol molecule forming the core.

As set forth above, it has been found that multi-functional alcohol molecules can be used to initiate of ROCOP of MAn with PO in the presence of a magnesium catalyst, thereby forming the star-shaped PPF-based 3D printable copolymers of the present invention. The initiating alcohol forming the core of the star-shaped PPF-based 3D printable copolymers of the present invention is not particularly limited provided that it has three or more available hydroxyl functional groups and is capable of initiating ROCOP of maleic anhydride (MAn) monomers, with propylene oxide (PO) monomers, in the presence of a magnesium catalyst. Suitable multi-functional alcohol initiators, may include, without limitation, glycerol (propane-1,2,3-triol), meso-erythritol ((2R,3S)-butane-1,2,3,4-tetrol), pentaerythritol (2,2-bis(hydroxymethyl)propane-1,3-diol), theitol ((2R,3R)-Butane-1,2,3,4-tetrol), arabitol ((2R,4R)-pentane-1,2,3,4,5-pentol) xilitol ((2R,3r,4S)-pentane-1,2,3,4,5-pentol), adonitol ((2R,3s,4S)-pentane-1,2,3,4,5-pentol), fucitol ((2R,3S,4R,5S)-hexane-1,2,3,4,5-pentol), sorbitol ((2S,3R,4R,5R)-hexane-1,2,3,4,5,6-hexol), dulcitol ((2R,3S,4R,5S)-hexane-1,2,3,4,5,6-hexol), mannitol (hexane-1,2,3,4,5,6-hexol) Iditol ((2R,3S,4S,5R)-Hexane-1,2,3,4,5,6-hexol), inositol (1R,2S,3r,4R,5S,6s)-cyclohexane-1,2,3,4,5,6-hexol), and volemitol ((2R,3R,5R,6R)-heptane-1,2,3,4,5,6,7-heptol). In some embodiments, the multi-functional alcohol initiator may be a sugar based alcohol. In one or more embodiments, the multi-functional alcohol initiator may be selected from the family of sugar based alcohols that includes meso-erythritol and adonitol. As set forth above, the meso-erythritol molecule bears four hydroxyl functional groups and it has been found that all hydroxyl groups of meso-erythritol are able to initiate the ROCOP of MAn with PO with a controlled manner to produce defined 4-arm star-shaped PPF copolymer. Similarly, the adonitol molecule bears five alcohol moieties and it has likewise been found that all hydroxyl groups of adonitol are able to initiate the copolymerization of MAn with PO with a controlled manner to produce defined 5-arm star-shaped PPF copolymer.

In one or more embodiments, the multi-functional alcohol initiator may include one or more other functional groups for post polymerization functionalization as described in international application publication number WO 2018/144849, the disclosure of which is incorporated herein by reference in its entirety.

In various embodiments, the magnesium catalyst may be $Mg(BHT)_2(THF)_2$ or $MgEt_2$, but is preferably $Mg(BHT)_2(THF)_2$.

In one or more embodiments, the arms of the PPF-based 3D printable star-shaped polymers of the present invention will comprise the isomerized residues a maleic anhydride monomer and residues of propylene oxide monomer. As follows, the terms "residues of propylene oxide monomer," "residues of propylene oxide" and "propylene oxide residue(s)" are all used herein to refer to the portion(s) of propylene oxide monomer incorporated into the poly(propylene fumarate) copolymers. Similarly, the terms "isomerized residue of a maleic anhydride monomer," "isomerized residues of maleic anhydride monomer," "isomerized residues of a maleic anhydride," "isomerized residues of maleic anhydride," and "isomerized maleic anhydride residues" are used interchangeably to refer to residues of the maleic anhydride monomer incorporated into the poly(propylene fumarate) copolymer of the present invention in which the carbon-carbon double bond has subsequently been isomerized from the cis (maleate) configuration to the trans (fumarate) configuration during formation of the poly(propylene fumarate) copolymer from the poly(propylene maleate) copolymer intermediate.

In some embodiments, the arms of the PPF-based 3D printable star-shaped polymers of the present invention may further comprise succinic anhydride residues as described in U.S. Provisional Application No. 62/697,433 filed Jul. 13, 2018, the disclosure of which is incorporated herein by reference in its entirety. In some embodiments, the arms of the PPF-based 3D printable star-shaped polymers of the present invention may further comprise residues of functionalized propylene oxide monomers as described in international application publication number WO 2018/144849, the disclosure of which is incorporated herein by reference in its entirety.

In some other embodiments, the arms of the multi-arm PPF copolymers of the present invention may comprise block copolymers of lactones and PPF as described in WO 2018/142384, the disclosure of which is incorporated herein by reference in its entirety. In these embodiments, the magnesium catalyst is first used to catalyze the formation a lactone block by ring opening polymerization of one or more lactone, and then to catalyze formation of a PPF block by ROCOP of MAn with PO as described above. It has been found that multi-arm PPF copolymers have a lower viscosity and comparable absorption than linear PPF copolymer. As a result, these copolymers can be used to prepare 3D printable resins with a lower weight fraction of the reactive solvent DEF.

As set forth above, the degree of polymerization and dispersity of the PPF must be carefully controlled to obtain polymers having the desired viscosity. As will be understood by those of ordinary skill in the art, the "degree of polymerization" (DP) generally refers to the number of number of monomer units in a macromolecule, polymer or oligomer molecule. As used herein, the degree of polymerization refers to the total number of propylene maleate or propylene fumarate units, respectively, forming the star-shaped PPM copolymer intermediate or star-shaped PPF copolymer of the present invention. As will be apparent, the DP of any one of the arms of the star-shaped PPF copolymer of the present invention (the "degree of polymerization by arm" "DP by arm" or "number of repetitive units by arm") will be the total DP for the star copolymer divided by the number of arms. So, by way of example, a 4-arm shaped PPF copolymer of the present invention having a total DP of 40, would have a DP by arm of 10.

In one or more of embodiments, the copolymers of the present invention have total DPs from about 3 to about 650, preferably from about 3 to about 325, and more preferably from about 3 to about 200. In some embodiments, the copolymers of the present invention will have a total DP of from about 3 to 5, in other embodiments, from about 3 to 10, in other embodiments, from about 3 to 15, in other embodiments, from about 3 to 20, in other embodiments, from about 3 to 30, in other embodiments, from about 3 to 50, in other embodiments, from about 3 to 100, in other embodiments, from about 3 to 200, in other embodiments, from about 10 to 200, in other embodiments, from about 20 to 200, in other embodiments, from about 40 to 200, in other embodiments, from about 80 to 200. Here, as well as elsewhere in the specification and claims, individual range values can be combined to form additional non-disclosed ranges.

In one or more embodiments, the star-shaped PPF copolymer composition of the present invention will have a number average molecular weight ($\overline{M_n}$) of from about 0.5 kDa to about 100 kDa, preferably from about 0.5 kDa to about 50 kDa, and more preferably from about 0.5 kDa to about 30 kDa, as calculated from NMR spectroscopy or measured by size exclusion chromatography (SEC) or gel permeation chromatography (GPC). In some embodiments, the star-shaped PPF copolymer composition of the present invention will have a number average molecular weight ($\overline{M_n}$) of from about 0.5 kDa to about 80 kDa, in other embodiments, from about 0.5 kDa to about 60 kDa, in other embodiments, from about 0.5 kDa to about 40 kDa, in other embodiments, from about 0.5 kDa to about 20 kDa, in other embodiments, from about 5 kDa to about 100 kDa, in other embodiments, from about 10 kDa to about 100 kDa, in other embodiments, from about 20 kDa to about 100 kDa, in other embodiments, from about 30 kDa to about 100 kDa, and in other embodiments, from about 50 kDa to about 100 kDa, as calculated from NMR spectroscopy or measured by size exclusion chromatography (SEC) or gel permeation chromatography (GPC).

In one or more of these embodiments, the star copolymer composition of the present invention will have a molecular mass distribution ($Đ_m$) of from about 1 to about 2, preferably from about 1 to about 1.7, and more preferably from about 1 to about 1.4. In some embodiments, the star copolymer composition of the present invention will have a $Đ_m$ of from about 1.0 to about 2.0, in other embodiments, from about 1.2 to about 2.0, in other embodiments, from about 1.4 to about 2.0, in other embodiments, from about 1.6 to about 2.0, in other embodiments, from about 1.8 to about 2.0, in other embodiments, from about 1.0 to about 1.9, in other embodiments, from about 1.0 to about 1.7, in other embodiments, from about 1.0 to about 1.5, and in other embodiments, from about 1.0 to about 1.3. Here, as well as elsewhere in the specification and claims, individual range values can be combined to form additional non-disclosed ranges. As used herein, the terms "dispersity," "polydispersity," "molecular mass distribution," and "molecular weight distribution" are used interchangeably to refer to the ratio of the weight average molecular weight to the number average molecular weight ($M_w/M_n$) of a material.

In one or more embodiments, the star-shaped PPF copolymer compositions of the present invention have an average complex viscosity of from about 0.1 Pa·s to about 10.0 Pa·s, preferably from about 1.0 Pa·s to about 5.0 Pa·s, and more preferably from about 3.0 Pa·s to about 5.0 Pa·s, as measured by a rheometer. In some embodiments, the star-shaped PPF copolymer compositions of the present invention have an average complex viscosity of from about 0.5 Pa·s to about 10.0 Pa·s, in other embodiments, from about 1.0 Pa·s to about 10.0 Pa·s, in other embodiments, from about 2.0 Pa·s to about 10.0 Pa·s, in other embodiments, from about 3.0 Pa·s to about 10.0 Pa·s, in other embodiments, from about 5.0 Pa·s to about 10 Pa·s, in other embodiments, from about 0.1 Pa·s to about 8.0 Pa·s, in other embodiments, from about 0.1 Pa·s to about 6.0 Pa·s, in other embodiments, from about 0.1 Pa·s to about 4.0 Pa·s, in other embodiments, from about 0.1 Pa·s to about 2.0 Pa·s, as measured by a rheometer. Here, as well as elsewhere in the specification and claims, individual range values can be combined to form additional non-disclosed ranges.

In various embodiments, the star-shaped PPF copolymer composition of the present invention may have an absorbance at 3D printable wavelengths (from about 305 nm to about 405 nm) of from about 0.001 to about 0.3, preferably from about 0.001 to about 0.2, and more preferably from about 0.001 to about 0.01, as measured by a UV-Visible spectrometer (range from 0.0097 for DP120 to 0.0683 for DP20). Here, as well as elsewhere in the specification and claims, individual range values can be combined to form additional non-disclosed ranges.

As will be apparent to those of skill in the art, the absorbance is calculated based on the measured transmittance using the formula:

$$A = 2 - \log_{10}(\% \ T) \quad \text{(Equation 1)}$$

where the transmittance (T) is the ratio of light that passes through the sample and absorbance (A) is the amount of light not transmitted (i.e. absorbed), relative to a reference standard.

In one or more embodiments, the star-shaped PPF copolymer composition of the present invention may have the following formula:

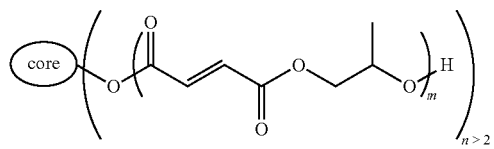

where m is the degree of polymerization by arm (also named number of repetitive units by arm) from about 1 to about 200, n is a number of arms greater than 2, and the "core" structure comprises the residue of the multi-functionalized alcohol initiator used to form the polymer. In some embodiments, n is from 3 to 6. In some embodiments, n is 4. In some embodiments, n is 5. In some embodiments, n is 5. In some embodiments, the core comprises the residue of meso-erythritol and n is 4. In some other embodiments, the core comprises the residue of adonitol and n is 5.

In another aspect, the present invention is directed to methods for making the multi-arm PPF star polymers described above. As will be apparent to those of skill in the art, the degree of polymerization may be controlled by controlling the available moles of initiator and/or the time and temperature of the polymerization reaction. In embodiments where the polymerization reaction is allowed to go to completion (where substantially all of the monomers have been reacted), the degree of polymerization may be controlled by controlling the available moles of initiating alcohol as a function of the total moles of available monomer. In some other embodiments, the degree of polymerization may be controlled by controlling ratio of the moles of initiating alcohol functions to both the moles of propylene oxide and the moles of maleic anhydride used to form the copolymer. In one or more of these embodiments, the maleic anhydride and propylene oxide are combined, with a 1:1 molar ratio, in a suitable sealed reaction vessel with an initiating alcohol, Mg(BHT)$_2$(THF)$_2$, and a suitable solvent. One of ordinary skill in the art will be able to select, configure, or create a suitable reaction vessel without undue experimentation. In one or more of these embodiments, maleic anhydride, propylene oxide and initiator are combined at a molar ratio of maleic anhydride to propylene oxide to alcohol initiating function of from about 200:200:1 to about 3:3:1.

Suitable solvents for this purpose are not particularly limited provided that the reaction proceeds and may include, without limitation, toluene, pentane, hexane, heptane, octane, THF, or a combination thereof. One of ordinary skill in the art will be able to select a suitable reaction solvent without undue experimentation.

In these embodiments, the combination of reactive species is heated until substantially all of the maleic anhydride and propylene oxide have reacted to form the star-shaped poly(propylene maleate) copolymer intermediate. In one or more embodiments, the star-shaped poly(propylene maleate) copolymer intermediate may have the following formula:

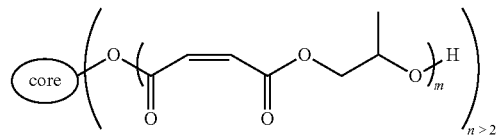

where m is the degree of polymerization by arm (also named number of repetitive units by arm) from about 1 to about 200, n is a number of arms greater than 2, and the core comprises the residue of the multi-functionalized initiator used to form the copolymer. In some embodiments, n is from 3 to 6. In some embodiments, n is 4. In some embodiments, n is 5. In some embodiments, the core comprises the residue of meso-erythritol and n is 4. In some other embodiments, the core comprises the residue of adonitol and n is 5.

In one or more of these embodiments, the sealed reaction vessel containing the reactive mixture is heated to a temperature of from about 40° C. to about 80° C. for from about 1 hour to about 200 hours (or until essentially all of the monomer is consumed) to produce a star-shaped cis-isomer poly(propylene maleate) intermediate of the star-shaped trans-isomer poly(propylene fumarate) copolymer composition of the present invention. In some embodiments, the sealed reaction vessel is heated to a temperature of from about 40° C. to about 75° C., in other embodiments, from about 40° C. to about 70° C., in other embodiments, from about 40° C. to about 65° C., in other embodiments, from about 40° C. to about 60° C., in other embodiments, from about 50° C. to about 80° C., in other embodiments, from about 60° C. to about 90° C., and in other embodiments, from about 70° C. to about 100° C. In some embodiments, the sealed reaction vessel is heated for from about 1 hour to about 200 hours, in other embodiments, in other embodiments from about 1 hour to about 150 hours, from about 1 hour to about 100 hours, in other embodiments, from about 1 hour to about 48 hours, in other embodiments, from about 1 hour to about 24 hours. In other embodiments, from about 24 hours to about 200 hours, in other embodiments, from about 48 hours to about 200 hours, in other embodiments, from about 150 hours to about 200 hours, and in other embodiments, from about 100 hours to about 200 hours.

The star-shaped poly(propylene maleate) copolymer intermediate may be recovered by any suitable method known in the art for that purpose. In some embodiments, the star-shaped poly(propylene maleate) copolymer intermediate may be recovered by precipitation into an excess of a non-solvent for the star-shaped poly(propylene maleate) copolymer intermediate such as diethyl ether, isopropyl alcohol, ethyl alcohol (also named ethanol), hexane, or a combination thereof.

The recovered star-shaped poly(propylene maleate) copolymer intermediate is then dried to remove remaining solvent. The star-shaped poly(propylene maleate) copolymer intermediate may be dried using any suitable method known in the art including, but not limited to vacuum evaporation, air drying, rotary evaporation, or a combination thereof.

As set forth above, the cis double bonds in the maleic anhydride residues of the star-shaped poly(propylene maleate) copolymer intermediate are next isomerized to arrive the star-shaped poly(propylene fumarate) copolymer described above. As used herein, the terms "isomerize" and "isomerization" refer broadly to the conversion of the cis-isomer (PPM) to its trans-isomer (PPF) form or, in the context of a chemical reaction or process (an "isomerization reaction") to a reaction or process that converts the cis-isomer (PPM) to its trans-isomer (PPF) form. And as set forth above, the terms "isomerized residue of a maleic anhydride monomer," "isomerized residues of maleic anhydride monomer," "isomerized residue of a maleic anhydride" and "isomerized residues of maleic anhydride" specifically refers to one or more residues of the maleic anhydride monomer used to form the star-shaped PPF-based 3D printable polymer composition of the present invention wherein the double bond has been isomerized from the cis (maleate) configuration to the trans (fumarate) configuration during formation of the poly(propylene fumarate) copolymer from the star-shaped poly(propylene maleate) copolymer intermediate, as described below. While the isomerization of the star-shaped poly(propylene maleate) copolymer intermediate does result in some other changes to the polymer, it should be understood that most general characteristics of the star-shaped PPF-based 3D printable polymer composition of the present invention, such as the approximate $\overline{M}_n$, $Đ_m$, and $T_g$ ranges, are determined in the initial ROCOP reaction and do not change during the isomerization reaction.

In one or more of these embodiments, the star-shaped poly(propylene maleate) copolymer intermediate is first dissolved in a suitable organic solvent. Suitable solvents for this purpose are not particularly limited provided that the reaction proceeds and may include, without limitation, chloroform, dichloromethane or a combination thereof. In one or more embodiments, the star-shaped poly(propylene maleate) copolymer intermediate is dissolved in chloroform. Next, a quantity of an organic base, such as diethylamine or pyridine, is added to the solution and it is heated to reflux temperature under an inert atmosphere to produce the star-shaped poly(propylene fumarate) copolymer of the present invention.

In some of these embodiments, the solution is heated to a reflux temperature under an inert atmosphere for from about 1 to about 48 hours (or until substantially all of star-shaped poly(propylene maleate) copolymer intermediate has isomerized) to produce the star-shaped poly(propylene fumarate) copolymer of the present invention. In some embodiments, the solution is refluxed for from about 1 hours to about 48 hours, in other embodiments, from about 1 hours to about 36 hours, in other embodiments, from about 1 hours to about 30 hours, in other embodiments, from about 1 hours to about 24 hours, in other embodiments, from about 6 hours to about 48 hours, in other embodiments, from about 12 hours to about 48 hours, in other embodiments, from about 18 hours to about 48 hours, in other embodiments, from about 24 hours to about 48 hours, and in other embodiments, from about 36 hours to about 48 hours to produce the star-shaped poly(propylene fumarate) copolymer of the present invention.

Finally, the star-shaped poly(propylene fumarate) produced may be washed with a sodium phosphate aqueous solution to remove residual monomers and base, and then dried to recover the star-shaped poly(propylene fumarate) copolymer. Finally, the star-shaped poly(propylene fumarate) copolymer may be purified by any suitable method known in the art for that purpose. In some of these embodiments, the star-shaped poly(propylene fumarate) copolymer is purified by repeated washing in an excess of sodium phosphate aqueous solution or a suitable acid solution, combining the organic layers, and drying the resulting polymer under vacuum to produce the purified polymer.

In another aspect, the present invention is directed to a photo-crosslinkable 3D printable resin comprising the star PPF copolymers described above. As set forth above, the star PPF copolymers of the present invention will, in various embodiments, have a substantially higher number average molecular mass ($\overline{M}_n$) at printable viscosities when compared to linear PPF polymers and will also crosslink more quickly than a comparable linear PPF. As a result, the star PPF copolymers of the present invention allow for the formulation of 3D printable resins having less DEF as a diluent, higher $\overline{M}_n$ and faster printing times than 3D printable resins prepared with conventional linear PPF polymers.

In one or more embodiments, the photo-crosslinkable 3D printable resin of the present invention will comprise one or more of the star PPF copolymers described above and DEF. In some embodiments, the photo-crosslinkable 3D printable resin of the present invention will comprise two or more different star PPF copolymers. In some embodiments, the photo-crosslinkable 3D printable resin of the present invention may also comprise one or more linear PPF. As will be apparent, the DEF serves both as a solvent/diluent for the star PPF copolymers and as a crosslinking agent when the polymer is later printed and cured. In various embodiments, the photo-crosslinkable 3D printable resin of the present invention will comprise from about 50 wt % to about 70% of the star PPF copolymers described above. In some embodiments, the photo-crosslinkable 3D printable resin of the present invention will comprise from about 55 wt % to about 70%, in other embodiments, from about 60 wt % to about 70% wt %, in other embodiments, from about 65 wt % to about 70% wt %, in other embodiments, from about 50 wt % to about 65% wt %, in other embodiments, from about 50 wt % to about 60% wt %, and in other embodiments, from about 50 wt % to about 55% wt % of the star PPF copolymers described above.

In one or more embodiments, the photo-crosslinkable 3D printable resins of the present invention having from about 30% to about 50% of DEF by weight will have an average complex viscosity of from about 0.01 Pa·s to about 25.0 Pa·s, preferably from about 2.0 Pa·s to about 5.0 Pa·s, and more preferably from about 0.1 Pa·s to about 1.5 Pa·s, as measured by a rheometer. In some embodiments, these photo-crosslinkable 3D printable resins (comprising from about 30% to about 50% of DEF by weight) will have an average complex viscosity of from about 0.5 Pa·s to about 25.0 Pa·s, in other embodiments, from about 1.0 Pa·s to about 25.0 Pa·s, in other embodiments, from about 2.0 Pa·s to about 25.0 Pa·s, in other embodiments, from about 4.0 Pa·s to about 25.0 Pa·s, in other embodiments, from about 8.0 Pa·s to about 25 Pa·s, in other embodiments, from about 0.1 Pa·s to about 20.0 Pa·s, in other embodiments, from about 0.1 Pa·s to about 15.0 Pa·s, in other embodiments, from about 0.1 Pa·s to about 10.0 Pa·s, in other embodiments, from about 0.1 Pa·s to about 4.0 Pa·s, as measured by a rheometer. Here, as well as elsewhere in the specification and claims, individual range values can be combined to form additional non-disclosed ranges.

The photo-crosslinkable 3-D printable resin will also contain one or more photoinitiators. The photoinitiators that may be used in the 3-D printable resin are not particularly limited and any photoinitiator capable of producing a radical at a suitable wavelength (approximately 254-450 nm) may be used. As will be appreciated by those of skill in the art, the choice of photoinitiator is often dictated by the requirements of the 3D printer being used. Suitable photoinitiators may include, without limitation, phenylbis(2,4,6-trimethylbenzoyl)phosphine oxide (BAPO), IRGACURE™ 819/BAPO (BASF, Florham Park, N.J.) or IRGACURE™ 784 (BASF, Florham Park, N.J.).

In addition, the photo-crosslinkable 3-D printable resin may contain one or more other additives commonly used in 3D printable resins such as dyes, light attenuating agents, radical scavengers, dispersants, emulsifiers, ceramics, bioglass, hydroxyapatite, β-tricalcium phosphate, crosslinkers and/or solvents. The dyes that may be used are not particularly limited and may be any dye conventionally used in 3D printing, provided that it does not quench the radicals necessary for crosslinking. The light attenuating agents that may be used are likewise not particularly limited and may include, without limitation, oxybenzone (2-Hydroxy-4-methoxybenzophenone) (Sigma-Aldrich). Suitable emulsifiers may include, without limitation, sucrose, threhalose, or any sugar molecule.

In various embodiments, the 3-D printable resin of embodiments of the present invention may include one or more other additives to support and/or promote tissue growth. The additives are not particularly limited provided that they do not quench the radicals needed for crosslinking of the 3-D printable resin. In various embodiments, the 3-D printable resin may contain additives such as, ceramics, BIOGLASS™, hydroxyapatite, β-tricalcium phosphate, and combinations thereof.

In one or more embodiments, the photo-crosslinkable 3D printable resin are formed by dissolving one or more of the star PPF copolymers described above in from about 30 wt % to about 50 wt % DEF to form a PPF:DEF solution containing from about 50 wt % to about 70 wt % of the star PPF copolymers described above. The various other resin components described above (e.g. photoinitiators, dyes, light attenuating agents, dispersants, emulsifiers, ceramics, bioglass, hydroxyapatite, β-tricalcium phosphate, crosslinkers and/or solvents) may be added to the 3-D printable resin at any time prior to crosslinking of the PPF polymer and are mixed evenly throughout the resin, as is known in the art. In some embodiments, a PPF/DEF solution having from about 50 wt % to about 70 wt % of the star PPF copolymers described above is first prepared. Next, two photoinitiators, phenylbis(2,4,6-trimethylbenzoyl)phosphine oxide (BAPO) and Irgacure 784, and a radical scavenger oxybenzone (HMB) are added to the PPF:DEF solutions at 3%, 0.4% and 0.7% by weight, respectively and mixed evenly throughout the resin, following a previously reported protocol with modification in the mixing ratio of copolymer and DEF to obtain a 3D printable star PPF resin. See, J. P. Fisher, D. Dean and A. G. Mikos, *Biomaterials,* 2002, 23, 4333-4343 and Y. Luo, C. K. Dolder, J. M. Walker, R. Mishra, D. Dean and M. L. Becker, *Biomacromolecules,* 2016, 17, 690-697, the disclosures of which are incorporated herein in their entirety.

The photo-crosslinkable 3-D printable resins of the present invention be printed using conventional additive manufacturing (3D printing) techniques, such as stereolithography or continuous digital light processing (cDLP) techniques and photocrosslinked to form 3D printed structures having virtually any shape. Any suitable light-based 3D printer may be used. Suitable 3-D printers may include, without limitation, Carbon3D printers (CARBON3D™, Redwood City, Calif.), PERFACTORY™ P3 3D printer (EnvisionTEC, Dearborn, Mich.), Micro HR 279 printer EnvisionTEC (Dearborn, Mich., USA), photocentric stereolithographic or photochemical 3D printers. In some embodiments, photo-crosslinkable 3-D printable resins of the present invention be printed using Micro HR 279 (EnvisionTEC, Dearborn, Mich., USA) printer using a 405 nm LED UV light projector with an irradiance of 225 mW·dm$^2$.

In various embodiments, the star PPF printed structure may be formed by first generating a set of instructions for 3-D printing a desired structure and sending those instructions to a suitable 3-D printer. In some of these embodiments, the set of instructions may comprise a computer assisted design (CAD) file generated using suitable computer software that are readable by the 3D printer to be used. In some embodiments, the design files may be created using SolidWorks software (Dassault Systems SolidWorks Corp., Waltham, Mass.). In some embodiments, the CAD models were sliced digitally into layers using the Perfactory software suite prior to manufacturing. The Perfactory P3 is an inverted system that projects upward through a transparent glass plate into a reservoir containing the resin. In one or more embodiments, the CAD or other computer file containing instructions for printing the star PPF printed structure may be generated as set forth in U.S. Pat. Nos. 6,849,223, 7,702,380, 7,747,305, 8,781,557, 9,208,558, 9,275,191, 9,292,920, 9,330,206, 9,626,756, 9,672,302, 9,672,617, and 9,688,023, the disclosures of which are incorporated herein by reference in their entirety.

As set forth above, the star PPF copolymers of the present invention will, in various embodiments, have a substantially higher number average molecular mass ($\overline{M}_n$) at printable viscosities when compared to linear PPF polymers and will also crosslink more quickly than a comparable linear PPF. These star PPF copolymers have been shown to greatly reduce printing times and to produce 3D printed structures with substantially better definition and mechanical properties than comparable linear PPF polymers. In some embodiments, printing times have been reduced by more than 50%.

Experimental

In order to more fully illustrate and reduce the invention to practice, four-arm PPF copolymers according to the present invention were synthesized as set forth above using sugar-based alcohol meso-erythritol as initiator with total DPs in a 20-200 range and their shape evaluated by a combination of $^1$H NMR spectroscopy, size exclusion chromatography (SEC), MALDI-ToF and viscosity measurements. (See, Examples 12-15) These star PPF polymers were used to prepare PPF:DEF resins with complex viscosities compatible with DLP 3D printing even for high DP values, and used to 3D printing of Gyroid scaffolds with a cylinder shape (8 mm×4 mm) and screws (4.5 mm height), which were evaluated.

Results and Discussion

The synthesis of four-arm star polypropylene maleate (PPM) was performed through a core-first approach using meso-erythritol as a multifunctional initiator possessing four hydroxy initiating functionalities and Mg(BHT)$_2$(THF)$_2$ as catalyst for the ring-opening copolymerization (ROCOP) of maleic anhydride (MAn) with propylene oxide (PO) (Scheme 1). Various total monomer concentrations were investigated for their influence on the copolymerization and with the aim of obtaining defined star-shaped copolymer with low viscosity adapted for 3D printing application.

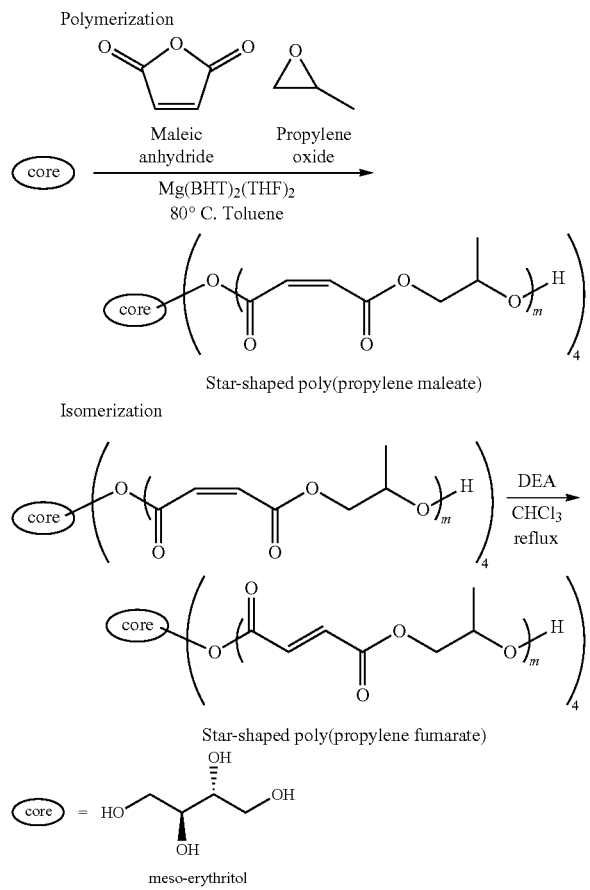

Scheme 1
Synthesis of star-shaped poly(propylene maleate) (PPM) polymers and subsequent isomericzation into star-shaped poly(propylene fumarate) (PPF).

Figure 2A:
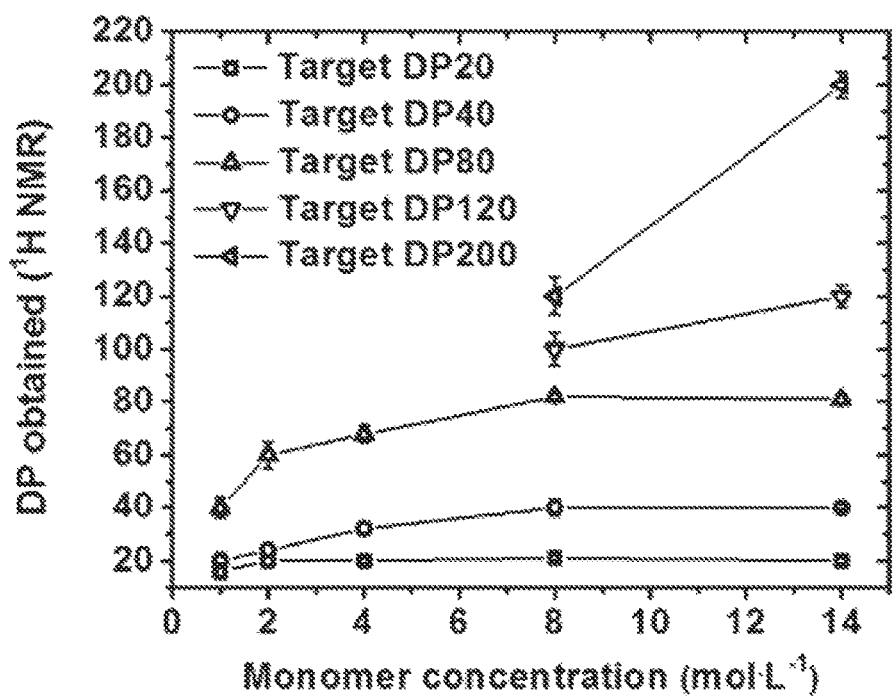
FIGS. 2A-C are graphs showing the evolution of total DP of four-arm shaped PPM as a function of monomer concentration (FIG. 2A); comparing the kinetic plots for the copolymerization of maleic anhydride and propylene oxide for star shaped PPM target DP40 (total monomer concentration 2 M, 4 M and 8 M), and linear PPM target DPs 10 and 40 (total initial monomer concentration=8 M), conducted at 80° C. in toluene with $[OH]_0$:$[Cat.]_0$=1:0.05 (FIG. 2B); and comparing changes in $\overline{M}_n$ over increasing MAn conversion determined by $^1H$ NMR (500 MHz, 303 K, $CDCl_3$) for the polymers described in FIG. 2B (FIG. 2C).

Initial copolymerization conditions employed a 1:1 molar ratio of MAn:PO, total monomer concentrations of 1, 2, 4, 8 and 14 M, and amounts of meso-erythritol targeting degrees of polymerization (DPs) of 5, 10, 20, 30 and 50 units for each arm corresponding to total target DPs 20, 40, 80, 120 and 200 respectively. The chemical structures of meso-erythritol used as initiator (FIG. 1 (upper)) and of poly(propylene maleate) (PPM) copolymers obtained were investigated by $^1$H NMR spectroscopic analyses (FIG. 1 (lower)). The star structure of copolymers was attested by the downfield shift of the signals 1, and 2' from the initiator (from 3.35 to 5.44 ppm and from 3.35 and 3.50 ppm to about 4.50 ppm respectively). The ratio of MAn and PO incorporated into the polymer backbone remained roughly equimolar, moreover, the absence of signal corresponding to the methylene protons observed from the homopolymerization of PO ($\delta$=3.3-3.5 ppm) confirmed the alternating copolymerization process. The DP values and the corresponding molar masses were calculated using the ratio of the proton integration 1 from the core and integrating for 2 $^1$H and the signal integration 3 attributed to the olefin protons of MAn repetitive units. The obtained DPs were plotted versus the monomer concentration for each of the target DPs (FIG. 2A). The resulting plot revealed a strong concentration dependence of the DP obtained. Higher target DP generally required higher monomer concentration. As an example, while the total target DP20 was reached from a 2 M concentration, a 14 M concentration was necessary to obtain full monomer conversion leading to a total DP of 200 (4×50).

Figure 2B:
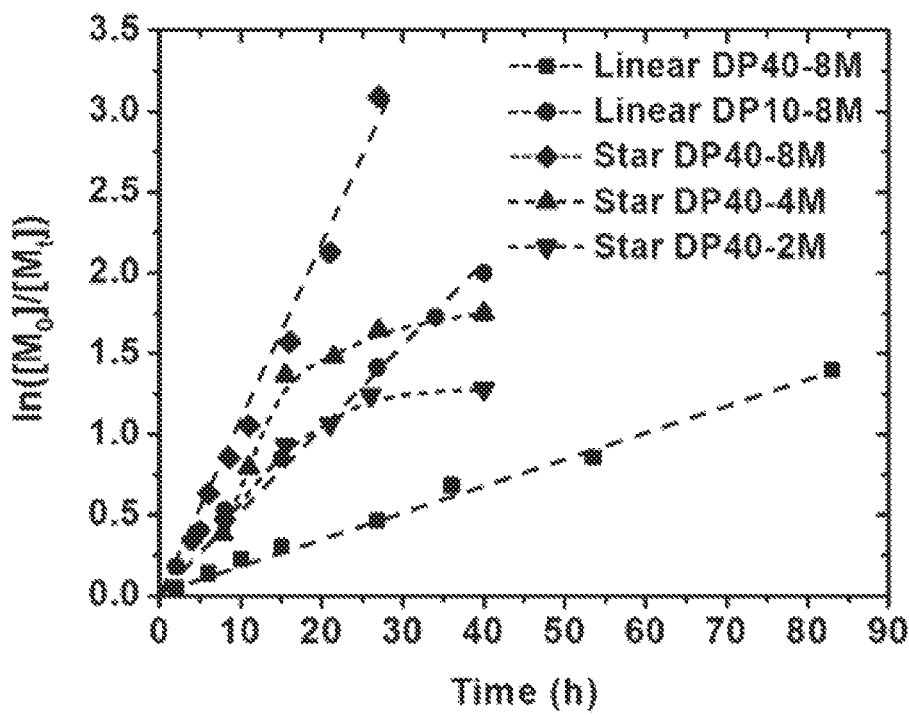
Figure 2C:
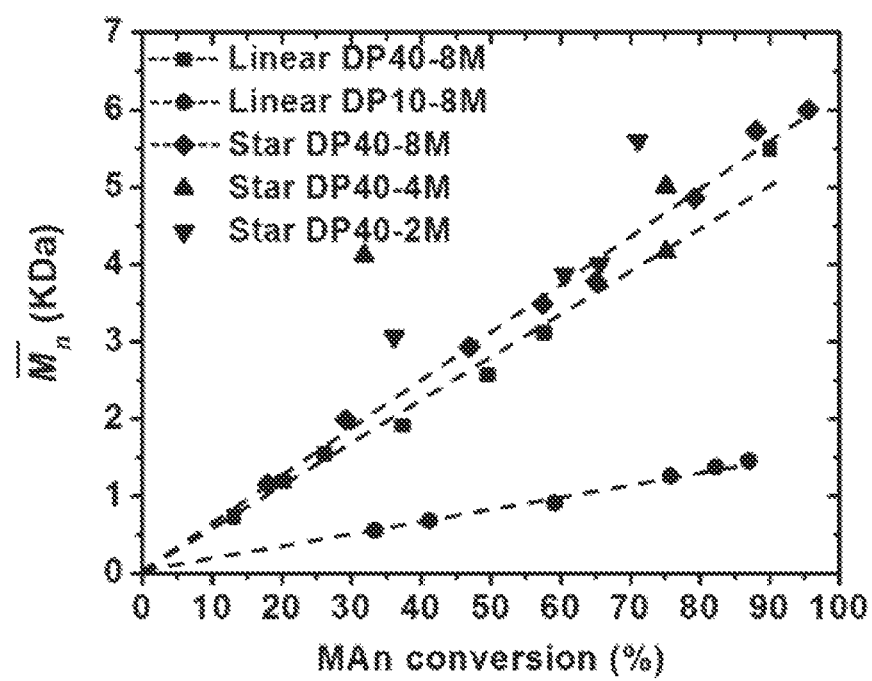
Figure 3A:
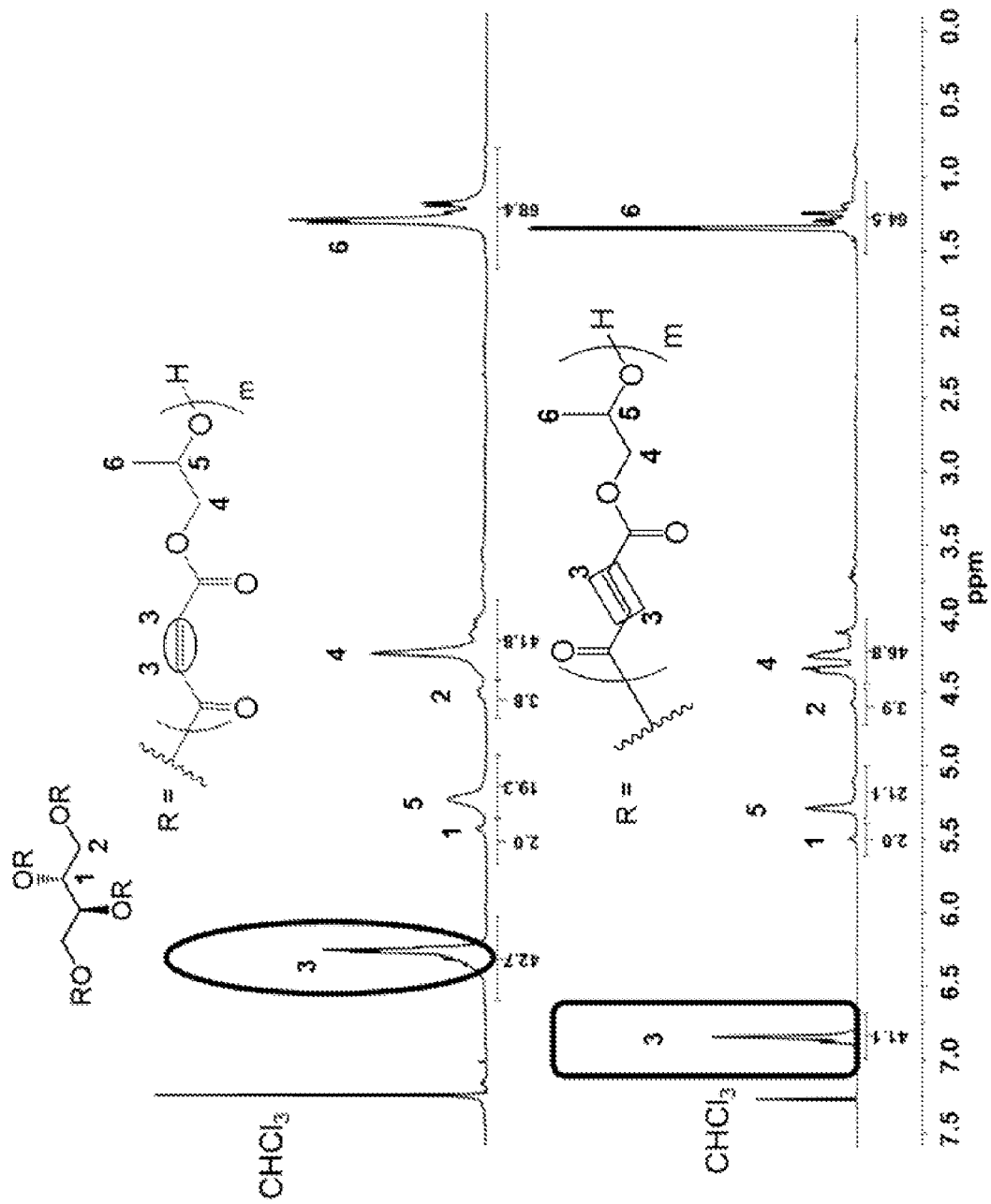
FIG. 3 are a comparison of $^1H$ NMR spectra of four-arm star poly(propylene maleate) of a total DP20 with a meso-erythritol core (top) and corresponding four-arm star poly (propylene fumarate) obtained after isomerization (bottom) (FIG. 3A) and a size exclusion chromatography profile of four-arm star poly(propylene maleate) of a total DP20 with a meso-erythritol core (FIG. 3B).
Figure 3B:
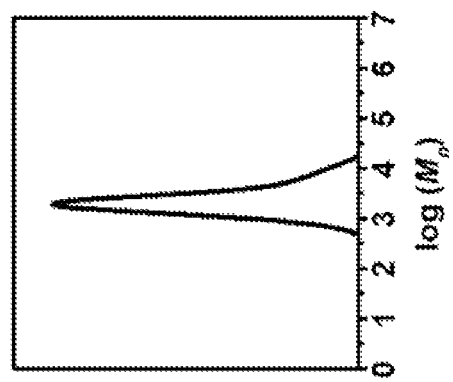
Figures 4A, 4B:
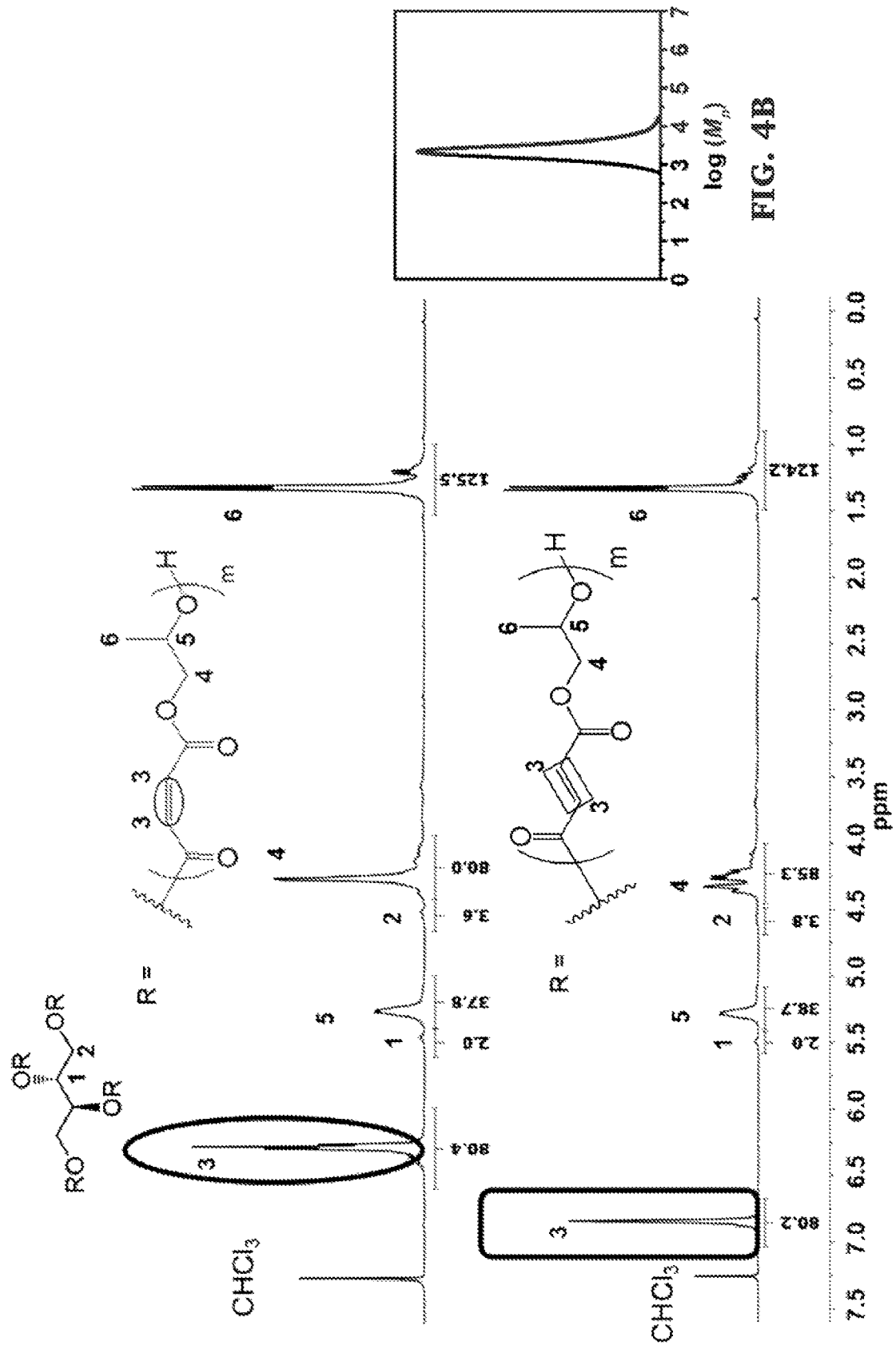
FIGS. 4A-B are a comparison of $^1H$ NMR spectra of four-arm star poly(propylene maleate) of a total DP40 with a meso-erythritol core (top) and corresponding four-arm star poly(propylene fumarate) obtained after isomerization (bottom) (FIG. 4A) and a size exclusion chromatography profile of four-arm star poly(propylene maleate) of a total DP40 with a meso-erythritol core (FIG. 4B).
Figures 6A, 6B:
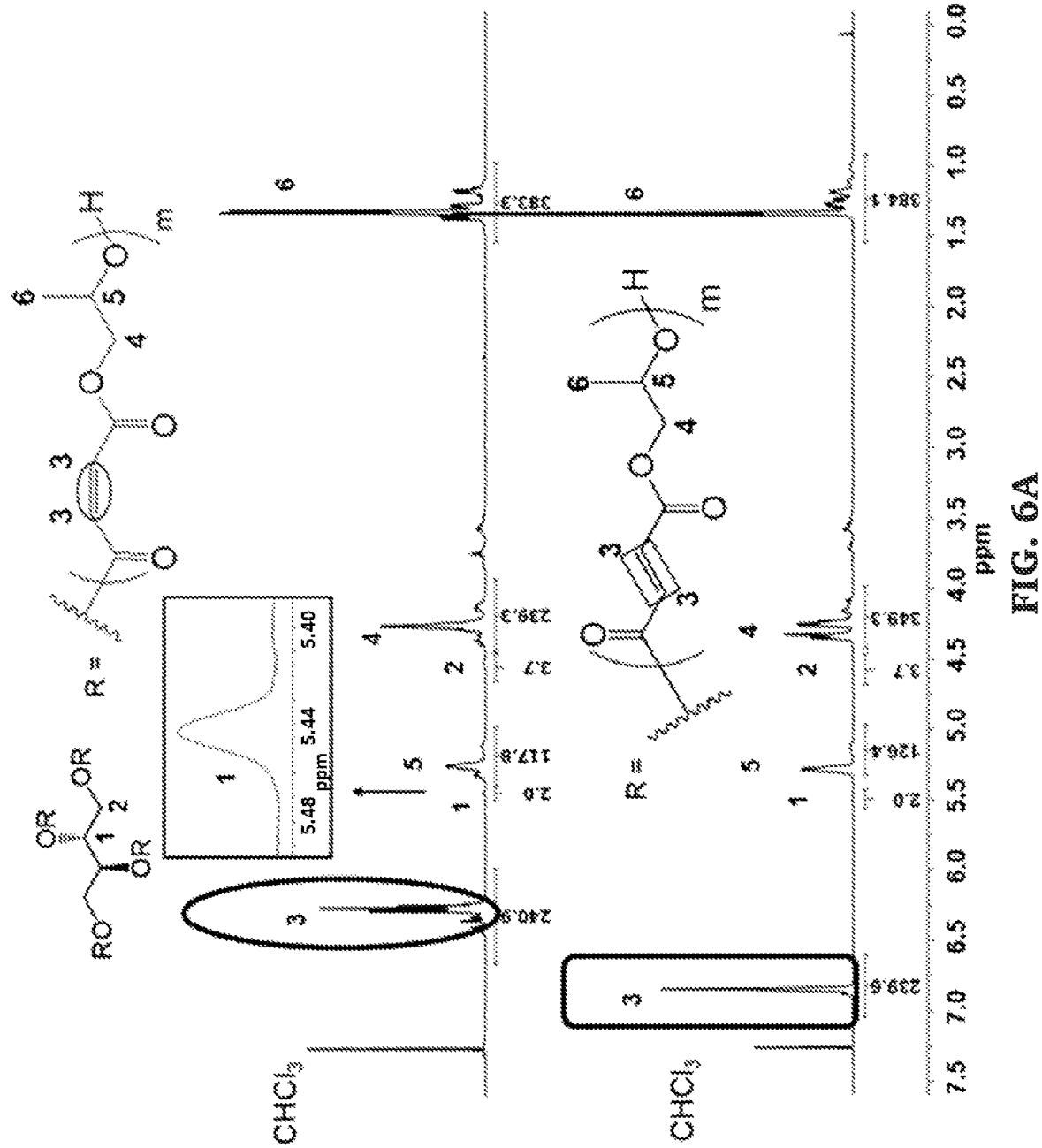
FIGS. 6A-B are a comparison of $^1H$ NMR spectra of four-arm star poly(propylene maleate) of a total DP120 with a meso-erythritol core (top) and corresponding four-arm star poly(propylene fumarate) obtained after isomerization (bottom) (FIG. 6A) and a size exclusion chromatography profile of four-arm star poly(propylene maleate) of a total DP120 with a meso-erythritol core (FIG. 6B).
Figure 7A:
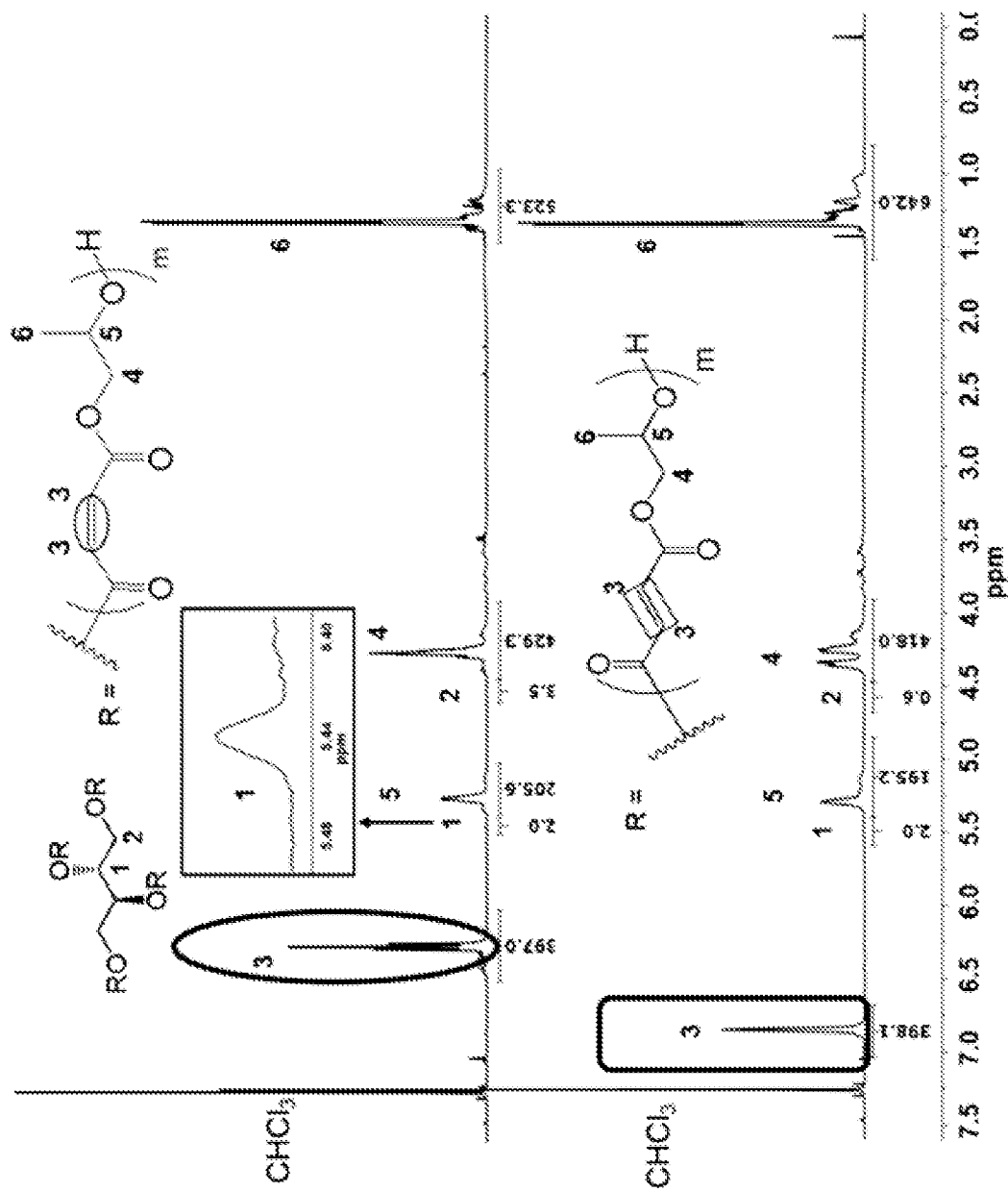
FIGS. 7A-B are a comparison of $^1H$ NMR spectra of four-arm star poly(propylene maleate) of a total DP200 with a meso-erythritol core (top) and corresponding four-arm star poly(propylene fumarate) obtained after isomerization (bottom) (FIG. 7A) and a size exclusion chromatography profile of four-arm star poly(propylene maleate) of a total DP200 with a meso-erythritol core (FIG. 7B).
Figure 7B:
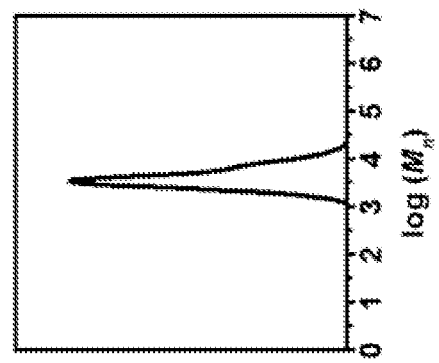

For a better understanding of the influence of the concentration during the copolymerization process, kinetic studies were performed at various concentrations (2 M, 4 M, 8 M) at target DP 40 using meso-erythritol as an initiator. For comparison, kinetic studies at 8 M were also conducted during the synthesis of linear PPM oligomers DP10 and DP40, corresponding to the DP of one arm or the total DP within the star structure. For this purpose, the $\ln([M_0]/[M_t])$ values and the MAn conversion were monitored via $^1$H NMR of the crude reaction mixture by comparing the monomer proton resonance ($\delta$=7.01 ppm) to the corresponding polymer proton resonance ($\delta$=6.27 ppm). The monomer conversion of PO was not characterized due to the low vapor pressure and boiling point of the PO leading to unreliable integrations assessed by $^1$H NMR spectroscopy. FIG. 2B and FIG. 2C show respectively the evolution of the $\ln([M_0]/[M_t])$ values with time and the evolution of number-average molar mass ($\overline{M_n}$) with the MAn conversion. For the star PPM synthesis, at 8 M (blue diamonds), the kinetic plot of $\ln([M]_0/[M]_t)$ against time revealed a linear relationship, which demonstrated a pseudo-first-order kinetics and thus suggested a living polymerization mechanism with a maintained number of active chains overtime and no termination side reactions. However, for copolymerizations performed at 2 M and 4 M (pink and green triangles respectively), the slowdown of the polymerization rate followed by a plateau, characteristic of an early termination of the polymerization, was observed demonstrating a loss of the living characteristics. The ROCOP of MAn with PO at 8 M to afford linear PPM followed pseudo-first-order-kinetics, as well for DP10 (red circles) and DP40 (black squares). From the slopes of these linear kinetic plots, the propagation rate constants $k_p'$ for the star PPM, and the linear PPM DP40 and DP10 respectively were calculated and found to be 2.30×10$^2$ L·mol$^{-1}$s$^{-1}$, 3.84×10$^{-3}$ L·mol$^{-1}$ s$^{-1}$ and 2.88×10$^{-3}$ L·mol$^{-1}$·s$^{-1}$. The synthesis of the star shape PPM DP40 is therefore eight times faster than the linear PPM DP40 and six times faster than the linear DP10.

$\overline{M_n}$ value obtained by $^1$H NMR was plotted against MAn conversion. The plot obtained showed that $\overline{M_n}$ increased linearly with conversion and no transfer reactions occurred during the copolymerization except at 2 M and 4 M.

These studies determined the optimal concentration conditions for the synthesis of four-arm star PPM with various DPs, from 20 to 200. The synthesis conditions and the molecular characteristics obtained by $^1$H NMR and size exclusion chromatography (SEC) in tetrahydrofuran (THF) are summarized in the Table 1. A strong correlation between expected DPs and DPs determined from $^1$H NMR was observed. As reported previously for star polymers, the SEC profiles of four-arm PPM (FIGS. 3-7) showed monomodal peaks shifted to earlier elution times compared with the linear polymer, due to their smaller hydrodynamic volume, inherent to the star architectures. Consequently, the apparent $\overline{M_n}$ values are lower than the actual values. The molar mass distributions (Dim) were between 1.28-1.48, corresponding to the $Đ_m$ range reported for the PPM synthesis by ROCOP of MAn with PO. (See, e.g., J. A. Wilson, D. Luong, A. P. Kleinfehn, S. Sallam, C. Wesdemiotis and M. L. Becker, *Journal of the American Chemical Society*, 2017, 140, 277-284, the disclosure of which is incorporated herein by reference in its entirety).

Figure 8:
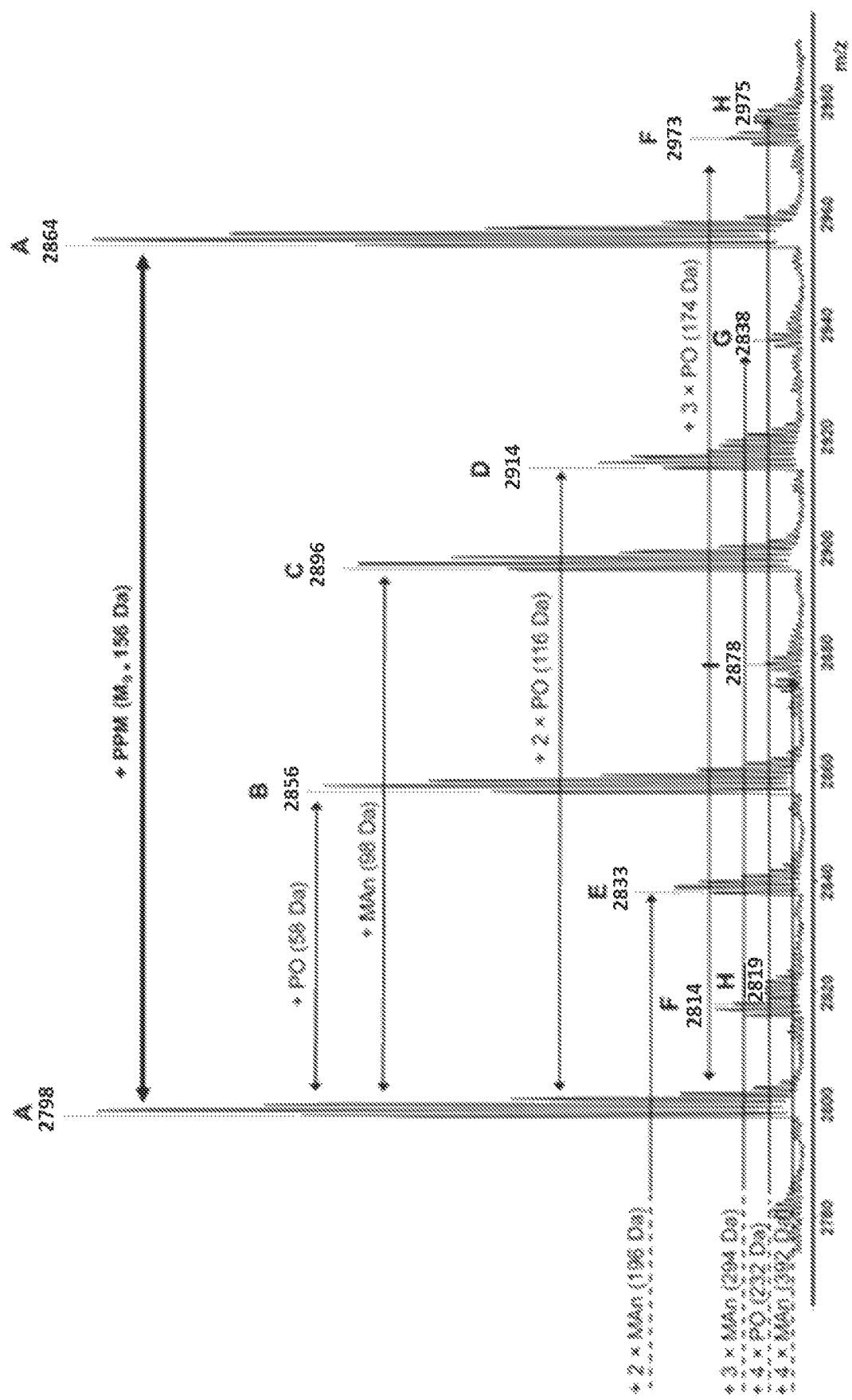
FIG. 8 is an enlarged portion of a MALDI-ToF MS spectrum of a DP20 four-arm poly(propylene maleate) (PPM) and corresponding end-group for each distribution.
Figure 9:
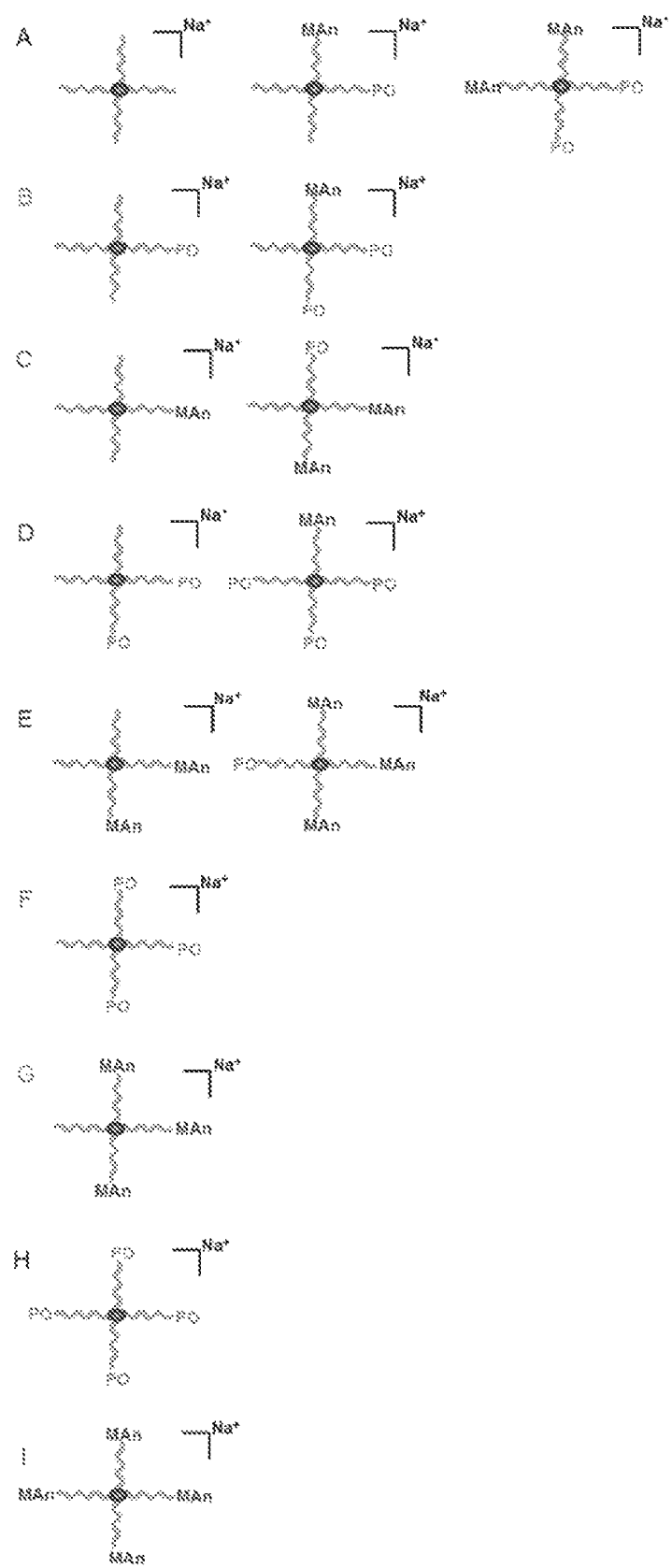
FIG. 9 are end-chain possibilities for each distribution from MALDI-ToF MS spectrum of four-arm poly(propylene maleate) (PPM).

Matrix assisted laser desorption/ionization time of flight mass spectrometry (MALDI-ToF MS) was used to investigate the chemical structure of the star polymer (FIG. 8) The end groups for all the distributions were calculated considering the molar mass of one Na+ cationizing agent (22.99 Da) to correspond to a meso-erythritol initiation. As expected from an alternating copolymerization system and as previously demonstrated for the linear PPM, (see, e.g., S. Sallam, Y. Luo, M. L. Becker and C. Wesdemiotis, *European Journal of Mass Spectrometry*, 2017, 23, 402-410, the disclosure of which is incorporated herein by reference in its entirety), several major contributions were observed and attributable to a full polymeric repeat unit (group A), a half polymeric repeat unit (i.e. one extra PO (group B) or one extra MAn (group C) incorporated on the chain-end of one arm) (See, FIG. 9). Due to the star architecture, more distributions were observed corresponding to two extra PO (group D), two extra MAn (group E), three extra PO (group F), three extra MAn (group G), four extra PO (group H) or four extra MAn (group I). Chain-end possibilities for each distribution are illustrated in FIG. 9.

3-7). As previously reported for PPF oligomers (see, e.g., S. Sallam, Y. Luo, M. L. Becker and C. Wesdemiotis, *European Journal of Mass Spectrometry*, 2017, 23, 402-410, the disclosure of which is incorporated herein by reference in its entirety), no degradation occurred during the isomerization step, as demonstrated by integration value of each signal.

Figure 12:
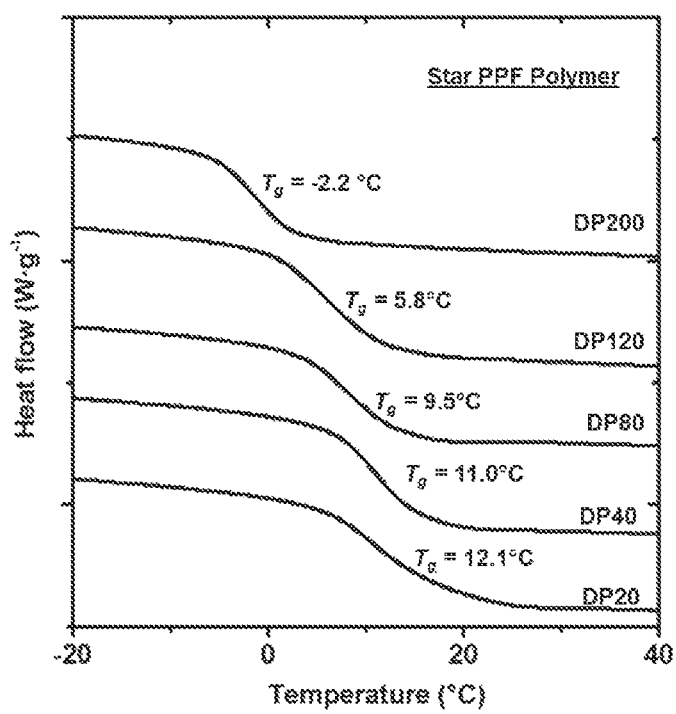
FIG. 12 is a comparison of differential scanning calorimetry (DSC) traces for PPF star polymers at DP20, DP40, DP80 DP120, and DP200. Temperature scan rate was 10° C.·min$^{-1}$.

Differential scanning calorimetry (DSC) was employed to investigate the thermal properties of star PFF copolymers (FIG. 12). As expected, the polymers were amorphous and their glass transition temperature ($T_g$) are reported in Table 1, above. In contrast to linear PPF for which $T_g$ values increased with the $\overline{M_n}$, PPF stars showed a decrease in $T_g$ values, from 12.1° C. for DP20 to −2.2° C. for DP200, highlighting an enhancement in chain mobility as the length of the arms increases.

The complex viscosities ($\eta^*$) of star PPF resin formulations in diethyl fumarate (DEF) were then investigated as function of DP and PPF:DEF weight ratios (i.e., 50:50, 60:40 and 70:30). The zero-shear viscosity ($\eta_0$) was calculated by extrapolation of the complex viscosity to zero angular frequency from a plot of complex viscosity versus

TABLE 1

Synthetic Conditions and Characterization of Star-shaped Poly(propylene maleate) (PPM).

| Target DP | [MAn]:[PO]:[I]:[Cat][a] | [Monomer] (M) | MAn converion (Mol %)[b] | DP (PPM) ($^1$H NMR)[b] | $\overline{M_n}$ $^1$H NMR[b] (KDa) | $\overline{M_n}$ SEC[c] (KDa) | $\overline{M_w}$ SEC[c] (KDa) | $Đ_m$ SEC[c] | $T_g$[d] (° C.) |
|---|---|---|---|---|---|---|---|---|---|
| 20 (4 × 5) | 20:20:1:0.2 | 4 | 99 | 21 | 3.4 | 1.8 | 2.7 | 1.45 | 12.1 |
| 40 (4 × 10) | 40:40:1:0.2 | 8 | 95 | 40 | 6.3 | 3.2 | 4.4 | 1.40 | 11.0 |
| 80 (4 × 20) | 80:80:1:0.2 | 8 | 99 | 82 | 12.9 | 3.2 | 4.6 | 1.48 | 9.5 |
| 120 (4 × 30) | 120:120:1:0.2 | 12 | 92 | 120 | 18.8 | 1.9 | 2.6 | 1.35 | 5.8 |
| 200 (4 × 50) | 200:200:1:0.2 | 14 | 96 | 198 | 31.0 | 3.5 | 4.5 | 1.28 | −2.2 |

[a][I] = 4[OH] for meso-erythritol,
[b]$^1$H NMR in CDCl$_3$,
[c]SEC in THF, RI detector, PS standards,
[d]DSC.

Since the homopolymerization of MAn has not been observed during copolymerization with PO, neither in previous study nor in the present work, the presence of a distribution corresponding to four MAn units as chain ends demonstrated the synthesis of four-arm star shape PPM. Hence, the copolymerization of MAn and PO using Mg(BHT)$_2$(THF)$_2$ as a catalyst has been initiated both from primary alcohol and secondary alcohol groups.

Figure 10A:
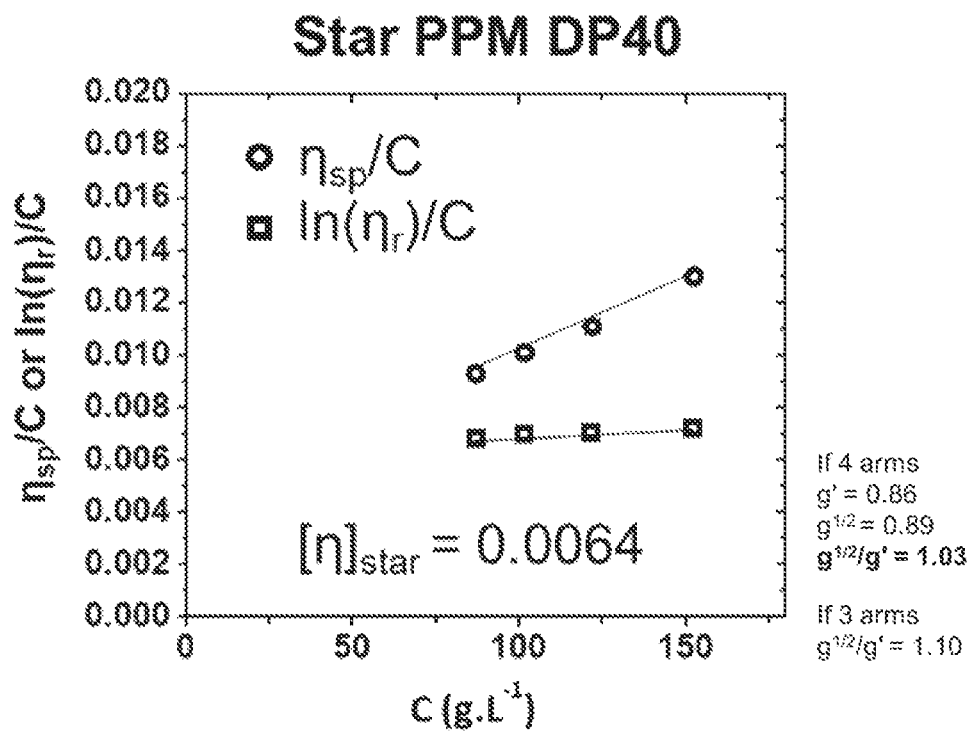
FIGS. 10A-B are graphs showing $\eta_{sp}/C$ and $\ln(\eta_r)/C$ versus polymer concentration for star PPF DP40 (FIG. 10A) and linear PPM DP40 (FIG. 10B) solution in THF. Calculation of $g^{1/2}/g'$ ratios corresponding to three or four arms demonstrating the synthesis of four-arm PPF.
Figure 10B:
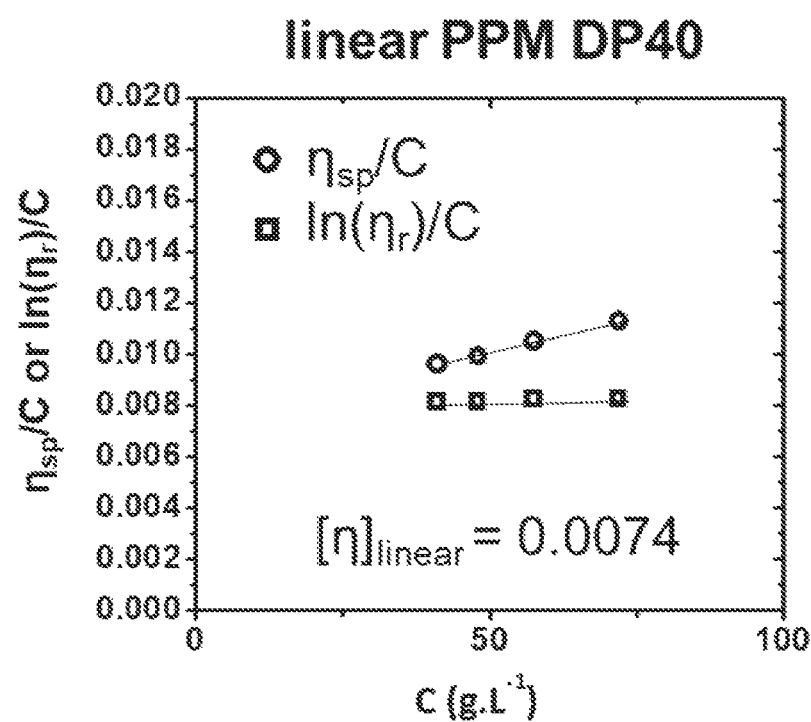

To confirm the arm number of star PPM, the intrinsic viscosities of star PPM DP40 (FIG. 10A) and linear PPM DP40 (FIG. 10B) were measured in THE. The values were obtained by plotting the reduced viscosity ($\eta_{red}=\eta_{sp}/C$) and the inherent viscosity ($\eta_{inh}=\ln(\eta_r)/C$) with the concentration and found to be $[\eta]_{star}=6.4\times10^{-3}$ L·g$^{-1}$ and $[\eta]_{linear}=7.4\times10^{-3}$ L·g$^{-1}$. As expected, star polymers present a lower $[\eta]$ value due to higher segment density and reduced amount of chain entanglements compared to linear polymers of equivalent $\overline{M_n}$. The ratios $g'=[\eta]_{star}/[\eta]_{linear}$ was equal to 0.86, the value $g=6f/[(f+1)(f+2)]$ for $f=4$ (arms) was 0.8, and consequently $g^{1/2}=0.89$. The relationship $g^{1/2}/g'=1.03\approx1.0$ confirmed the number of arms is four.

Figure 11:
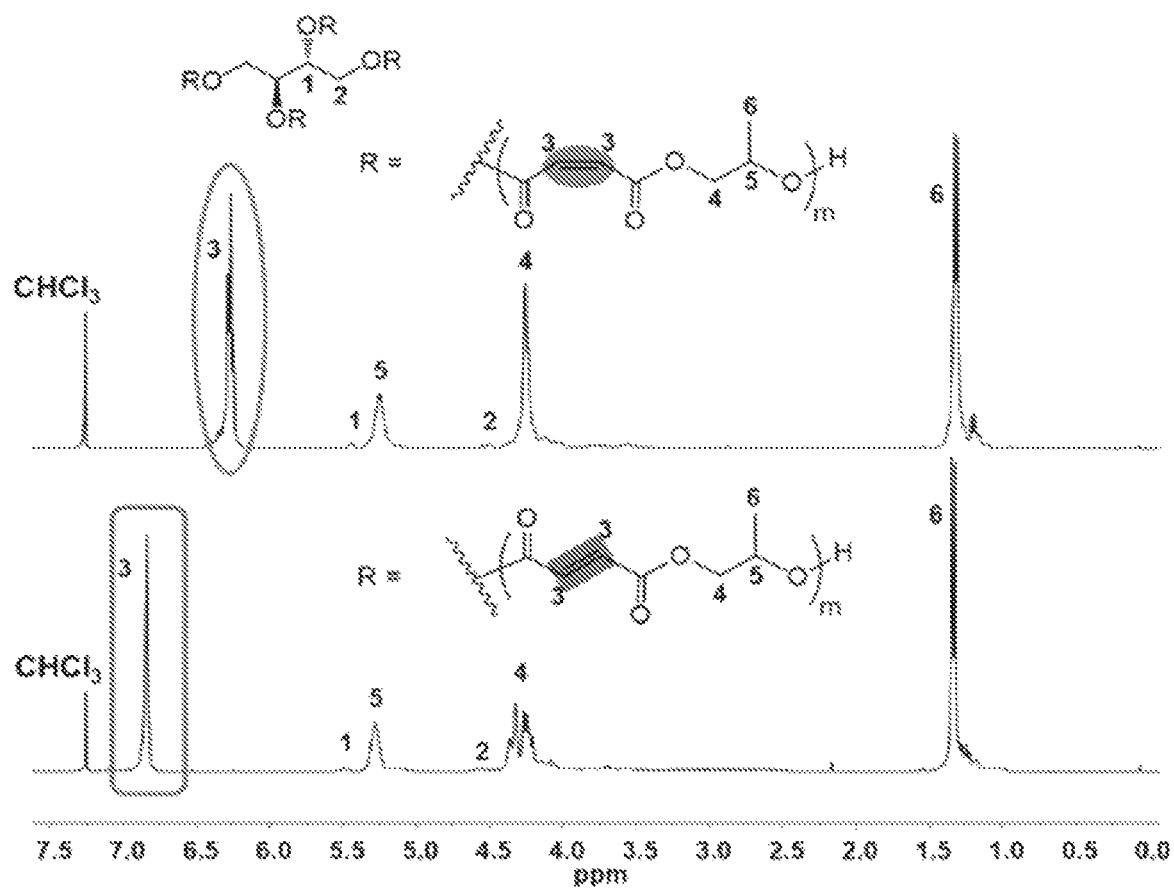
FIG. 11 is a comparison of the $^1$H NMR spectrum of four-arm star-shaped PPM DP 40 (upper) and $^1$H NMR spectrum of four-arm star-shaped PPF DP 40 with a meso-erythritol core (500 MHz, 303 K, CDCl$_3$) (lower).
Figure 13:
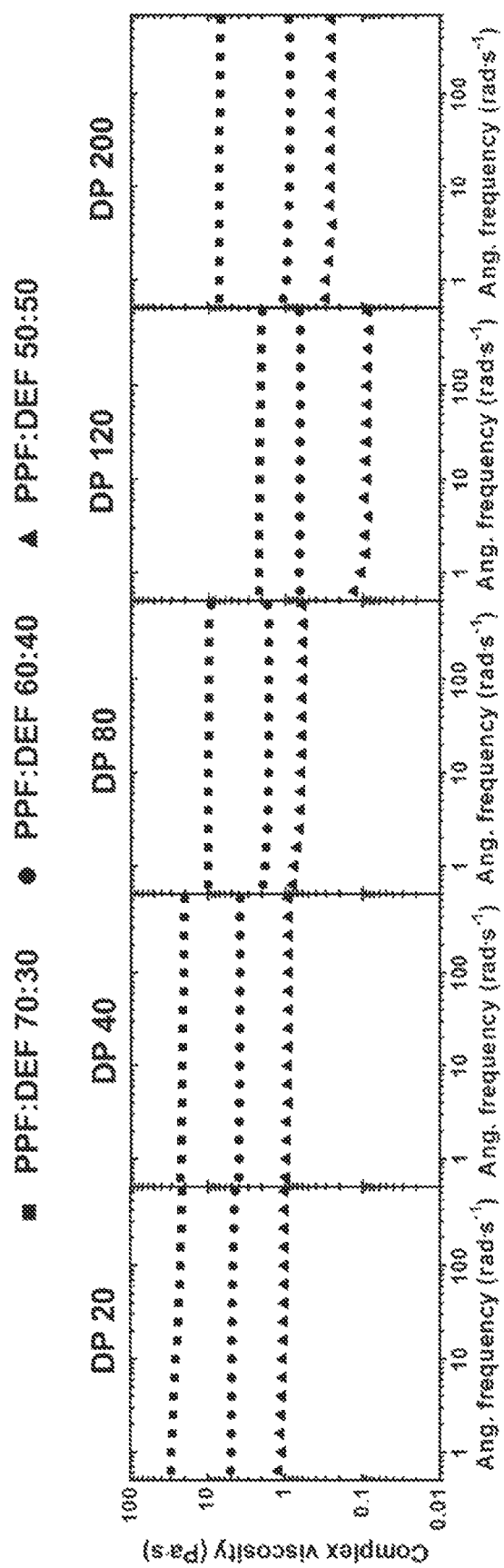
FIG. 13 is a comparison of the complex viscosity ($\eta^*$) of PPF:DEF solutions (without photoinitiators and radical scavenger) as a function of the DP of the star PPF (20, 40, 80, 120 and 200).
Figure 14:
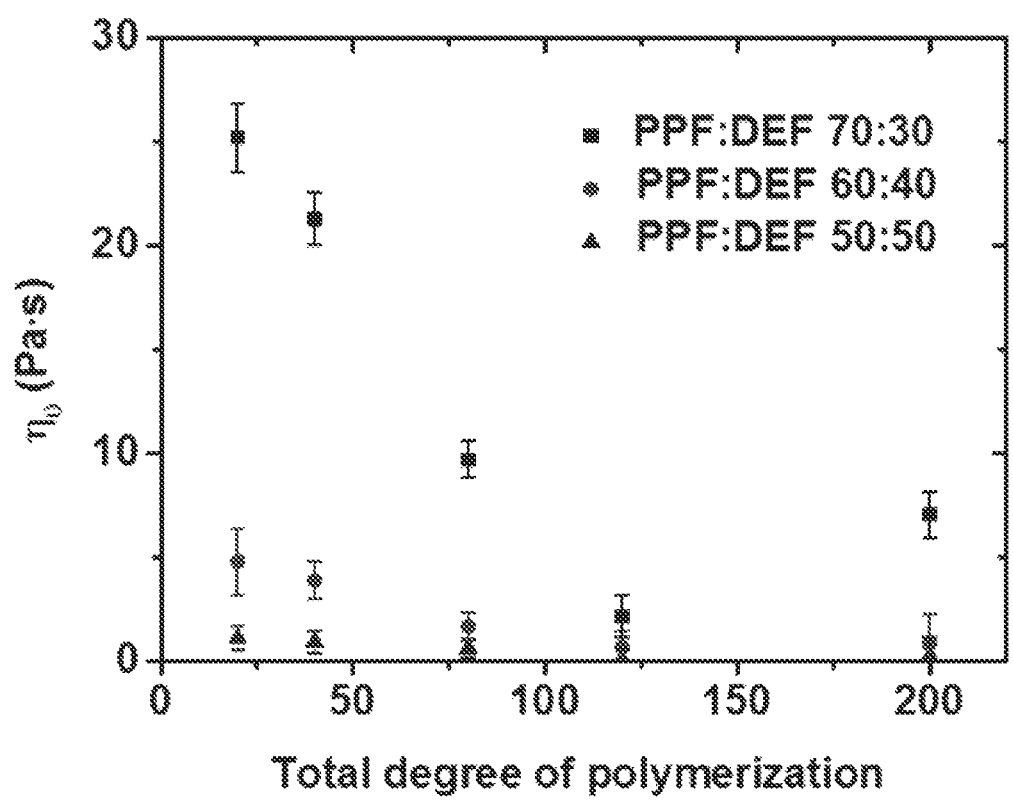
FIG. 14 is a graph showing zero-shear viscosity ($\eta_0$) of PPF:DEF solutions as a function of the DP of the star PPF for three PPF:DEF ratios (50:50, 60:40 and 70:30).

$^1$H NMR spectra obtained before and after isomerization reaction attested that star PPM (FIG. 11 (upper)) was successfully isomerized to star PPF (FIG. 11 (lower)) by showing the disappearance of the proton resonance signal corresponding to cis-alkene protons ($\delta$=6.3 ppm) and the appearance of the new proton resonance signal corresponding to trans-alkene protons ($\delta$=6.7 ppm). All the other $^1$H NMR spectra are shown in supporting information (FIGS.

angular frequency (FIG. 13). The zero-shear viscosity ($\eta_0$) as a function of number-average molar mass ($\overline{M_n}$) of star PPF are presented in FIG. 14.

The zero-shear viscosity values ($\eta_0$) for the PPF:DEF weight ratio 70:30 (black squares in FIG. 14), for each DP, were found, as expected, to be systematically higher than the values obtained for the PPF:DEF weight ratios 60:40 (red circles) which are higher than the PPF:DEF weight ratio 50:50 (blue triangle). Interestingly, the star shape caused an important and linear decrease of the zero-shear viscosity as the DP increased from 20 to 120, followed by a slight increase for DP200. On the contrary, for the linear PPF oligomers, it has been previously shown that increasing DP leads to a drastic increase of the zero-shear viscosity (see, e.g., Y. Luo, G. Le Fer, D. Dean and M. L. Becker, *Biomacromolecules*, 2019, 20, 1699-1708, the disclosure of which is incorporated herein by reference in its entirety), which makes it impossible to 3D print resins based on PPF with DP higher than about 20, limiting the exploration of properties of the materials obtained. It is believed that this rheological behavior can be explained by the $T_g$ decrease of the PPF stars as their $\overline{M_n}$ increases and by a possible increase of chain entanglement for the highest $\overline{M_n}$, corresponding to a $\eta_0$ increase.

Because of the low viscosity, the PPF:DEF (50:50) resin based on the four-arm star PPF DP200 was used for digital light processing (DLP) 3D printing of model gyroid scaffolds (FIG. 15), after addition of photo-initiators and radical scavenger. Cure tests and printing tests were performed to determine the most appropriate UV exposure time/layer for each formulation. A 25 µm layer thickness allowed for better attachment of the gyroid structures on the basement plate while an increase of the total DP of the PPF used in the formulation led to a significant decrease of the curing time/layer. Indeed, for the previously used linear PPF of DP10, a curing time/layer of 225 s was necessary, when only 60 s allowed the printing for the star PPF of DP200. Consequently, the total printing duration of scaffolds with a 4 mm height has been reduced from more than 13 h for the linear DP10 to less than 5 h 30 min for the star DP200. Consequently, the total printing duration of scaffolds with a 4 mm height has been reduced from more than 13 h for the linear DP10 to less than 5 h 30 min for the star DP200.

Figure 15A:
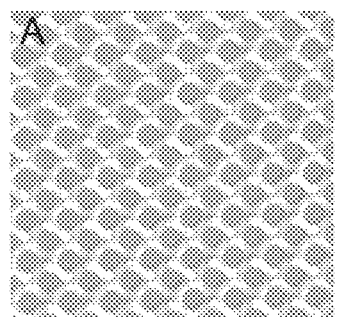
FIGS. 15A-D are comparisons of a printed gyroidal scaffold and the CAD model from which it was printed.
Figure 15B:
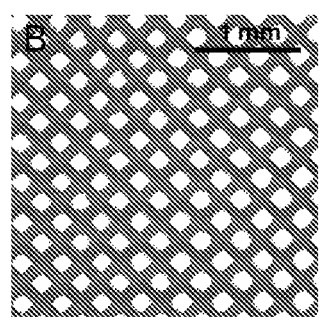
Figure 15C:
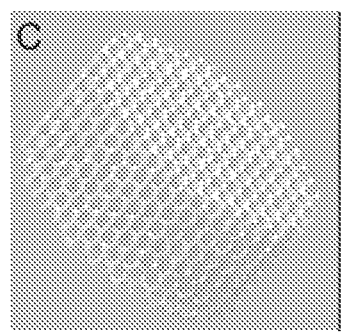
Figure 15D:
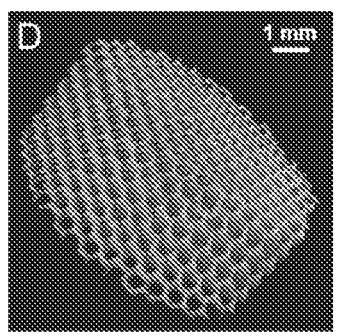

Because the internal pore geometry impacts directly the capacity of the scaffold to guide neo-tissues, the vasculature infusion into the defect and can improve cell seeding and/or nutrient flow for ex vivo culturing, it is of primary importance to well characterize the relationship between the resin formulation, the printing parameters and the scaffold architecture. For this purpose, the scaffolds were imaged by optical microscopy to depict the gyroid architecture features in greater detail and to determine their actual strut size (FIG. 15B). The structure of the gyroid scaffolds was also characterized by X-ray micro-computed tomography (µ-CT) to determine their total porosity (FIG. 15D). The corresponding pore sizes were calculated using the Schoen's gyroid triply periodic minimal surface equation. (See, J. M. Walker, E. Bodamer, O. Krebs, Y. Luo, A. Kleinfehn, M. L. Becker and D. Dean, *Biomacromolecules*, 2017, 18, 1419-1425 and J. M. Walker, E. Bodamer, A. Kleinfehn, Y. Luo, M. Becker and D. Dean, *Progress in Additive Manufacturing*, 2017, 2, 99-108, the disclosures of which are incorporated herein by reference in their entirety). The scaffolds obtained from the star PPF of DP200 were homogeneous with highly reproducible spatial arrangement of pores. The porosity values, the measured strut sizes and pore sizes correspond closely to CAD model used.

Moreover, PPF star-based screws were successfully printed using a CAD model (FIG. 16A) with a 4.5 mm height. (See Example 15). Indeed, resorbable screws are a structure of interest since screws are commonly used to provide a press fit between bone and to graft such. The screws obtained (FIG. 16C) were imaged by optical microscopy (FIG. 16B) showing good correlation with the model.

CONCLUSION

Here, four-arm PPF was synthesized through a core-first approach using sugar-based alcohol meso-erythritol as the initiator with total DPs in a 20-200 range. The star-shape of these polymers was confirmed by a combination of $^1$H NMR spectroscopy, size exclusion chromatography (SEC), MALDI-ToF and viscosity measurements. These results indicated initiation of the copolymerization of MAn and PO using Mg(BHT)$_2$(THF)$_2$ as a catalyst from both primary alcohol and secondary alcohol groups. The star PPF allowed for the preparation of PPF:DEF resins with complex viscosities compatible with DLP 3D printing even for high DP values, allowing accurate 3D printing of gyroids scaffolds based on PPF with $\overline{M_n}$, nearly 8 times largest than of the largest PPF oligomer previously printed.

EXAMPLES

The following examples are offered to more fully illustrate the invention, but are not to be construed as limiting the scope thereof. Further, while some of examples may include conclusions about the way the invention may function, the inventor do not intend to be bound by those conclusions, but put them forth only as possible explanations. Moreover, unless noted by use of past tense, presentation of an example does not imply that an experiment or procedure was, or was not, conducted, or that results were, or were not actually obtained. Efforts have been made to ensure accuracy with respect to numbers used (e.g., amounts, temperature), but some experimental errors and deviations may be present. Unless indicated otherwise, parts are parts by weight, molecular weight is number average molecular weight, temperature is in degrees Centigrade, viscosity is in Pa·s, and pressure is at or near atmospheric.

In a first set of Experiments (Examples 1-11), multi-arm star-shaped poly(propylene maleate) (PPM) copolymers were synthesized by ring opening copolymerization (RO-COP) of maleic anhydride (MAn) and propylene oxide (PO) using two sugar-based alcohols, i.e. meso-erythritol or adonitol, as initiators. Meso-erythritol was used as a multi-functionalized initiator to synthesize a four-arm PPM, while adonitol was used as a multi-functionalized initiator to synthesize five-arm PPM. Various monomers/initiator molar ratios were used to obtain copolymers with different PPM arm lengths. In the isomerization reaction, the cis-isomer (PPM) was converted to the trans-isomer (PPF) form in the presence of a catalyst. Because the isomerization step does not result in significant other changes to the polymer, most general aspects of the star-shaped PPF copolymers of embodiments of the present invention, such as the approximate DP, $\overline{M_n}$ and the Ð$_m$ are determined in the first reaction. Finally, these star-shaped PPF copolymers were combined with DEF in varying amounts to form PPF:DEF resins and the complex viscosity of which were evaluated for suitability for 3D printing.

Materials

All materials for Examples 1-11 were purchased from Millipore-Sigma. Mg(BHT)$_2$(THF)$_2$ was synthesized as modified method of previous report. (See, Wilson, J. A.; Hopkins, S. A.; Wright, P. M.; Dove, A. P., *Polym. Chem.*, 2014, 5, 2691-2694, the disclosure of which is incorporated herein by reference in its entirety.) All solvent were purchased from Fisher and dried using a Pure Solv MD-3 solvent purification system (Innovative Technology Inc.) and degassed prior to use. Meso-erythritol and adonitol were dried by azeotropic distillation before use. Maleic anhydride was dried under vacuum over P$_2$O$_1$ for one week. Propylene oxide was dried over calcium hydride overnight prior to vacuum distillation. All other reagents were used as received.

Instrumental Methods

Proton ($^1$H) NMR experiments were performed in CDCl$_3$ at 25° C. using a Varian Varian NMRS 500 spectrometer. All chemical shifts were recorded in parts per million (ppm) relative to the reference peak solvent: chloroform at δ=7.26. Degrees of polymerization (DPs) and molecular weights were calculated from $^1$H NMR integrations. The dispersities (Ð) of polymers were determined by size exclusion chromatography (SEC) on a Tosoh EcoSEC HLC-8320GPC with TSKgel GMHHR-M columns in series. The detector used in this determination is a refractive index detector (RI). Tetrahydrofurane (THF) was used as eluent flowing at 1.0 mL·min$^{-1}$. Molecular weights were calculated through a calibration curve determined from polystyrene standards. The sample concentration is 10 mg·mL$^{-1}$ General Procedure for Synthesis of Star-Shaped PPM Copolymer The general procedure for synthesis of these multi-arm star-shaped poly(propylene maleate) (PPM) copolymers was as follows: in a glovebox, the sugar-based alcohol initiator (meso-erythritol or adonitol), Mg(BHT)$_2$(THF)$_2$ catalyst, anhydrous toluene, MAn and PO were introduced in a flame-dried Schlenk, in this order. The total monomer concentration was 8 M. The Schlenk was sealed with PTFE plug and removed from the glovebox. The mixture was stirred at 80° C., under stirring, for a defined period time (typically until the PPM precipitated in the bottom of the Schlenk and the supernatant looked clear). The resultant copolymer was recovered by precipitation in diethyl ether and then dried under vacuum to afford a sticky beige powder.

Example 1

Synthesis of 4-Arm Star Poly(Propylene Maleate) of a Total DP20 with a Meso-Erythritol Core Meso-erythritol (112.12 g·mol$^{-1}$, 249.1 mg, 2.04 mmol), Mg(BHT)$_2$(THF)$_2$ (604.95 g·mol$^{-1}$, 246.8 mg, 4.08×10$^{-1}$ mmol), anhydrous toluene (10.2 mL), MAn (98.06 g·mol$^{-1}$, 4.0 g, 40.8 mmol) and PO (58.08 g·mol$^{-1}$, 2.85 mL, 40.8 mmol) were introduced in a flame-dried schlenk, in this order. The schlenk was sealed with a PTFE plug and removed from the glovebox. The solution was stirred at 80° C. for 24 hrs. The resultant copolymer was recovered by precipitation in diethyl ether and then dried under vacuum to afford a sticky beige powder. Yield: 88%.

Figure 17:
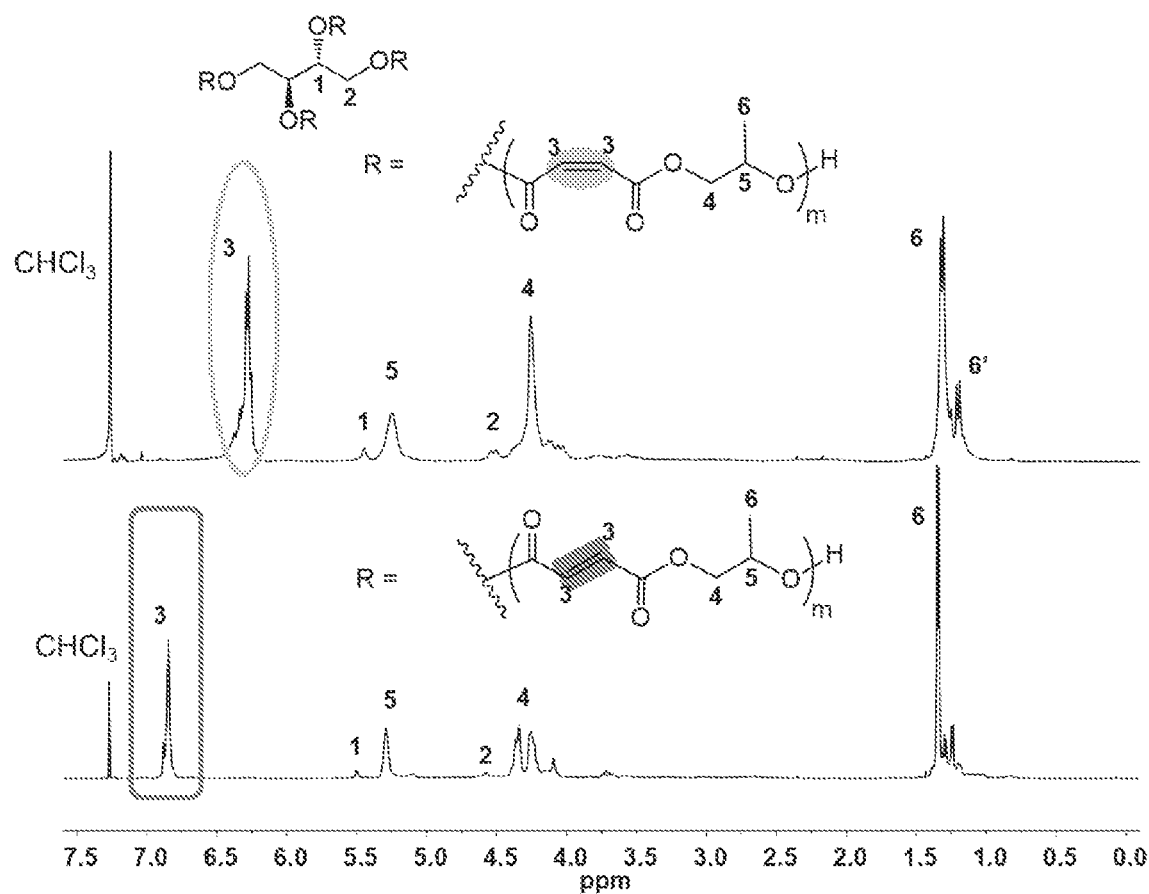
FIG. 17 is a comparison of $^1$H NMR spectra of 4-arm star poly(propylene maleate) of a total DP20 with a meso-erythritol core (top) and corresponding 4-arm star poly (propylene fumarate) obtained after isomerization (bottom).
Figure 18:
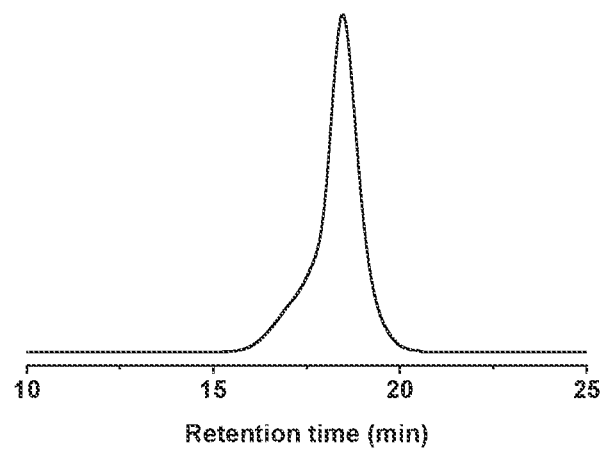
FIG. 18 is the size exclusion chromatography profile of 4-arm star poly(propylene maleate) of a total DP20 with a meso-erythritol core.

The resulting 4-arm star poly(propylene maleate) copolymer was characterized by $^1$H NMR (500 MHz, 298 K, CDCl$_3$): 6.42-6.18 (m, 42.1H, C=OCHCHC=O), 5.44 (m, 2H, CH(OR)CH$_2$OR), 5.36-5.17 (m, 21.2H, CH$_2$CHCH$_3$O), 4.55-4.47 (d, 1.7H, CH(OR)CHHOR), 4.45-4.00 (m, 44.9H, OCH$_2$CHCH$_3$), 1.41-1.23 (m, 54.3H, CH(CH$_3$)O), 1.23-1.0 (m, 12.1H, CH(CH$_3$)OH). A $^1$H NMR spectrum of 4-arm star poly(propylene maleate) of a total DP20 with a meso-erythritol core is shown in FIG. 17 (top). The degree of polymerization and the resulting molecular weight ($\overline{M_n}$) were confirmed by $^1$H NMR calculations. The molecular mass distribution (dispersity) (Đ$_m$) was determined by size exclusion chromatography (SEC), and the trace is shown in FIG. 18. The results are reported on Table 2, below.

Example 2

Synthesis of 4-Arm Star Poly(Propylene Maleate) of a Total DP40 with a Meso-Erythritol Core Meso-erythritol (112.12 g·mol$^{-1}$, 124.5 mg, 1.02 mmol), Mg(BHT)$_2$(THF)$_2$ (604.95 g·mol$^{-1}$, 123.4 mg, 2.04×10$^{-1}$ mmol), anhydrous toluene (10.2 mL), MAn (98.06 g·mol$^{-1}$, 4.0 g, 40.8 mmol) and PO (58.08 g·mol$^{-1}$, 2.85 mL, 40.8 mmol) were introduced in a flame-dried schlenk, in this order. The schlenk was sealed with a PTFE plug and removed from the glovebox. The solution was stirred at 80° C. for 48 hrs. The resultant copolymer was recovered by precipitation in diethyl ether and then dried under vacuum to afford a sticky beige powder. Yield: 78%

Figure 19:
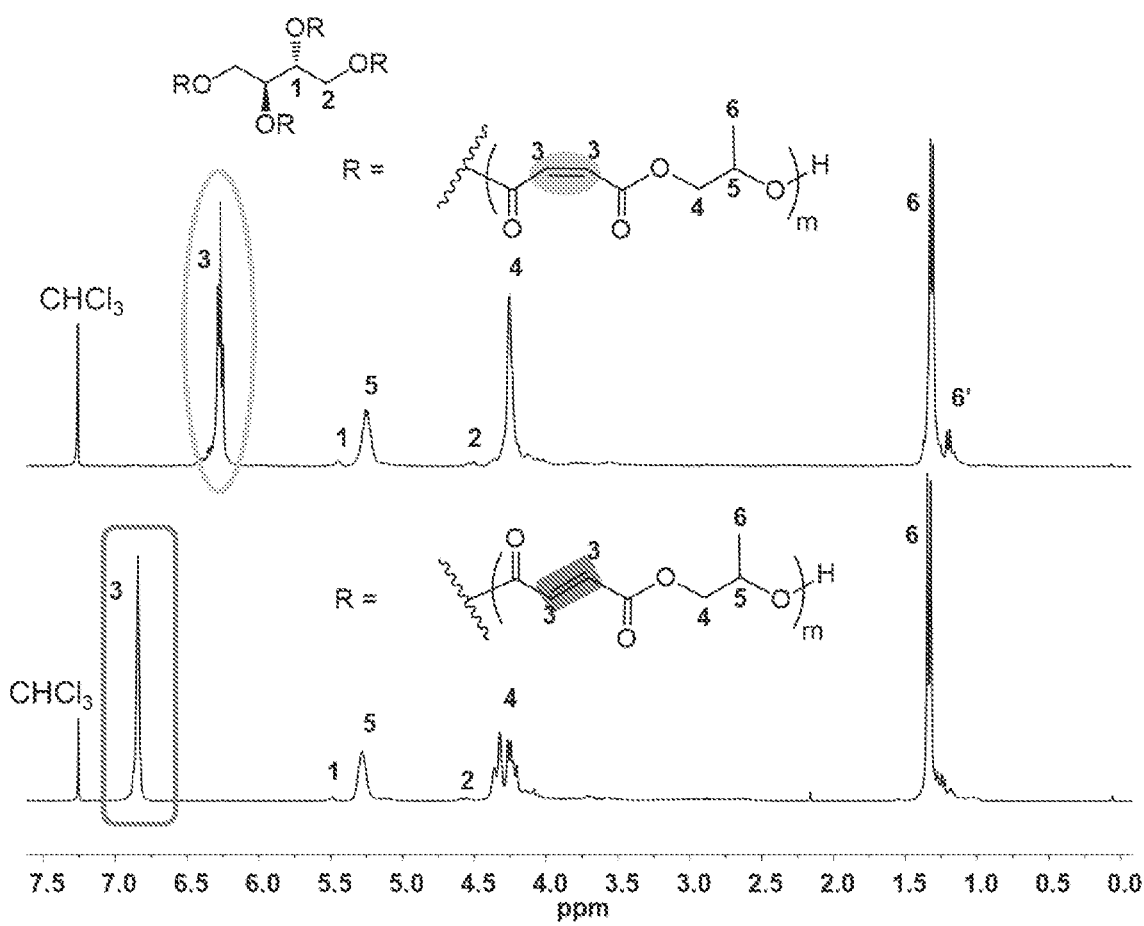
FIG. 19 is a comparison of $^1$H NMR spectra of 4-arm star poly(propylene maleate) of a total DP40 with a meso-erythritol core (top) and corresponding 4-arm star poly (propylene fumarate) obtained after isomerization (bottom).
Figure 20:
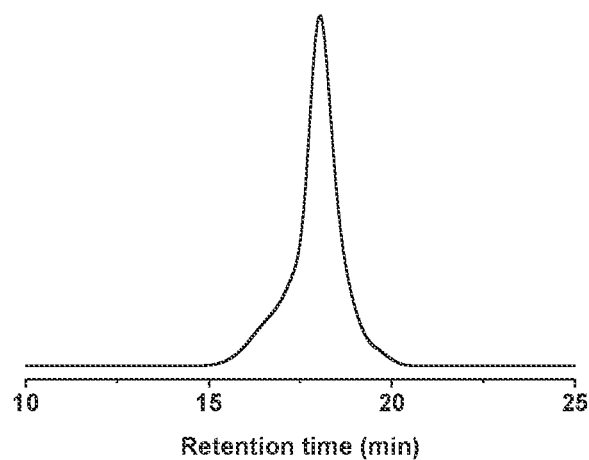
FIG. 20 is the size exclusion chromatography profile of 4-arm star poly(propylene maleate) of a total DP40 with a meso-erythritol core

The resulting 4-arm star poly(propylene maleate) copolymer was characterized by $^1$H NMR (500 MHz, 298 K, CDCl$_3$): 6.42-6.18 (m, 79.3H, C=OCHCHC=O), 5.44 (m, 2H, CH(OR)CH$_2$OR), 5.36-5.17 (m, 37.5H, CH$_2$CHCH$_3$O), 4.55-4.47 (d, 2.1H, CH(OR)CHHOR), 4.45-4.00 (m, 86.5H, OCH$_2$CHCH$_3$), 1.41-1.25 (m, 130.2H, CH(CH$_3$)O), 1.25-1.0 (m, 11.8H, CH(CH$_3$)OH). A $^1$H NMR spectrum of 4-arm star poly(propylene maleate) of a total DP40 with a meso-erythritol core is shown in FIG. 19 (top). The degree of polymerization and the resulting molecular weight ($\overline{M_n}$) were confirmed by $^1$H NMR calculations. The dispersity (Đ$_m$) was determined by size exclusion chromatography (SEC), and the trace is shown in FIG. 20. The results are reported on Table 2, below.

Example 3

Synthesis of 4-Arm Star Poly(Propylene Maleate) of a Total DP80 with a Meso-Erythritol Core Meso-erythritol (112.12 g·mol$^{-1}$, 62.3 mg, 5.10×10$^{-1}$ mmol), Mg(BHT)$_2$(THF)$_2$ (604.95 g·mol$^{-1}$, 61.7 mg, 1.02×10$^{-1}$ mmol), anhydrous toluene (10.2 mL), MAn (98.06 g·mol$^{-1}$, 4.0 g, 40.8 mmol) and PO (58.08 g·mol$^{-1}$, 2.85 mL, 40.8 mmol) were introduced in a flame-dried schlenk, in this order. The schlenk was sealed with a PTFE plug and removed from the glovebox. The solution was stirred at 80° C. for 100 hrs. The resultant copolymer was recovered by precipitation in diethyl ether and then dried under vacuum to afford a sticky beige powder. Yield: 82%

Figure 21:
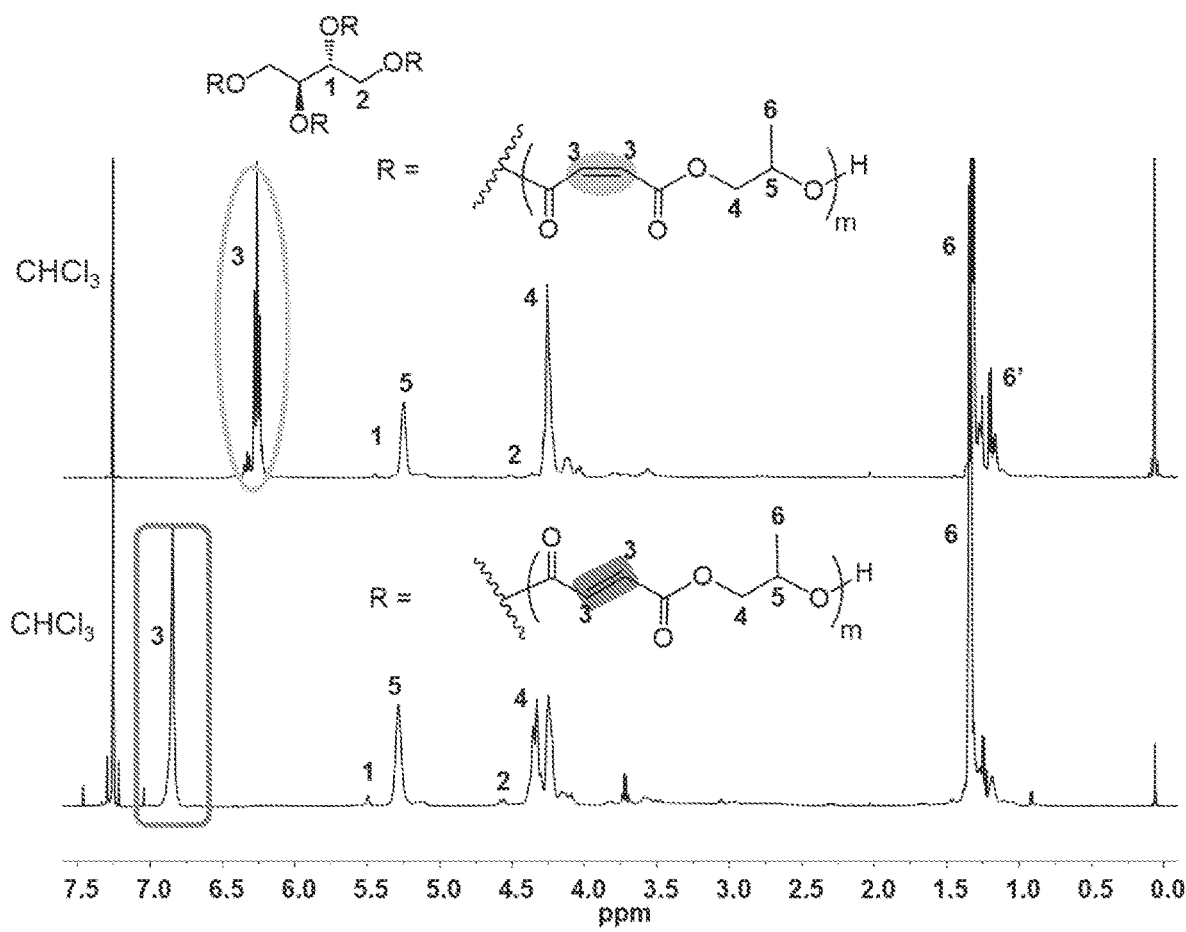
FIG. 21 is a comparison of $^1$H NMR spectra of 4-arm star poly(propylene maleate) of a total DP80 with a meso-erythritol core (top) and corresponding 4-arm star poly (propylene fumarate) obtained after isomerization (bottom).
Figure 22:
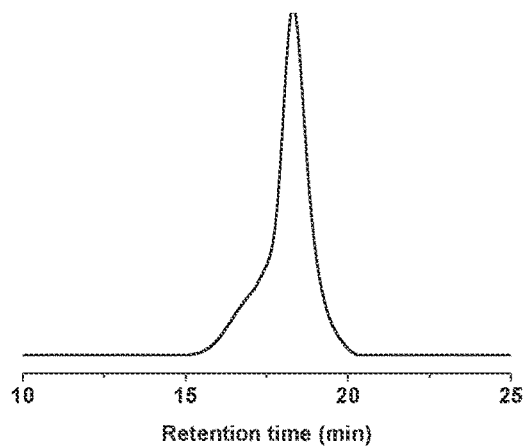
FIG. 22 is the size exclusion chromatography profile of 4-arm star poly(propylene maleate) of a total DP80 with a meso-erythritol core

The resulting 4-arm star poly(propylene maleate) copolymer was characterized by $^1$H NMR (500 MHz, 298 K, CDCl$_3$): 6.47-6.18 (m, 161.3H, C=OCHCHC=O), 5.44 (m, 2H, CH(OR)CH$_2$OR), 5.37-5.05 (m, 82.2H, CH$_2$CHCH$_3$O), 4.58-4.46 (d, 2.4H, CH(OR)CHHOR), 4.45-3.98 (m, 194.8H, OCH$_2$CHCH$_3$), 1.51-1.25 (m, 251.4H, CH(CH$_3$)O), 1.21-1.0 (m, 13.6H, CH(CH$_3$)OH). A $^1$H NMR spectrum of 4-arm star poly(propylene maleate) of a total DP80 with a meso-erythritol core is shown in FIG. 21 (top). The degree of polymerization and the resulting molecular weight ($\overline{M_n}$) were confirmed by $^1$H NMR calculations. The dispersity (Đ$_m$) was determined by size exclusion chromatography (SEC), and the trace is shown in FIG. 22. The results are reported on Table 2.

Example 4

Synthesis of 4-Arm Star Poly(Propylene Maleate) of a Total DP120 with a Meso-Erythritol Core Meso-erythritol (112.12 g·mol$^{-1}$, 31.1 mg, 2.55×10$^{-1}$ mmol), Mg(BHT)$_2$(THF)$_2$ (604.95 g·mol$^{-1}$, 30.8 mg, 5.10×10$^{-2}$ mmol), anhydrous toluene (7.6 mL), MAn (98.06 g·mol$^{-1}$, 3.0 g, 30.6 mmol) and PO (58.08 g·mol$^{-1}$, 2.14 mL, 30.6 mmol) were introduced in a flame-dried schlenk, in this order. The schlenk was sealed with PTFE plug and removed from the glovebox. The solution was stirred at 80° C. for 150 hrs. The resultant copolymer was recovered by precipitation in diethyl ether and then dried under vacuum to afford a sticky beige powder. Yield: 72%

Figure 23:
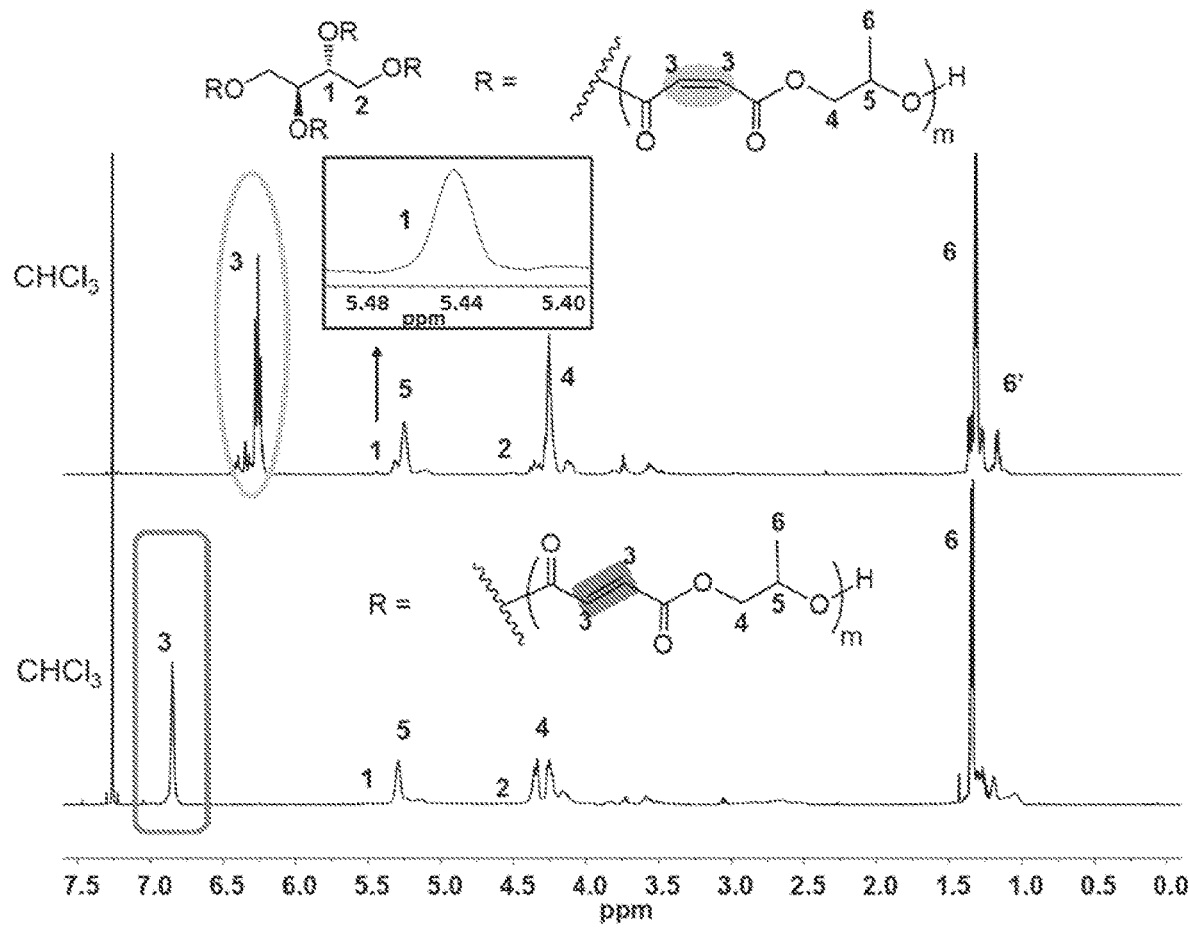
FIG. 23 is a comparison of $^1$H NMR spectra of 4-arm star poly(propylene maleate) of a total DP120 with a meso-erythritol core (top) and corresponding 4-arm star poly (propylene fumarate) obtained after isomerization (bottom).
Figure 24:
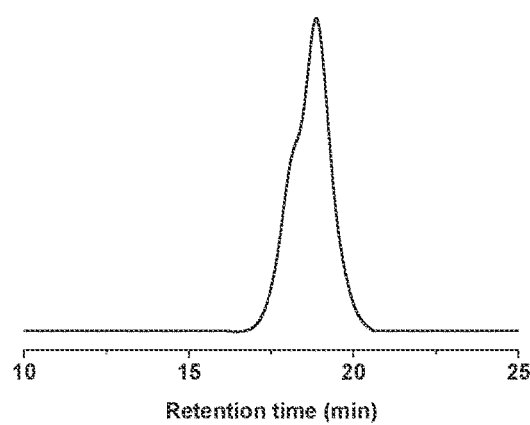
FIG. 24 is the size exclusion chromatography profile of 4-arm star poly(propylene maleate) of a total DP120 with a meso-erythritol core

The resulting copolymer was characterized by $^1$H NMR (500 MHz, 298 K, CDCl$_3$): 6.50-6.18 (m, 239.9H, C=OCHCHC=O), 5.44 (m, 2H, CH(OR)CH$_2$OR), 5.37-4.96 (m, 113.2H, CH$_2$CHCH$_3$O), 4.58-4.46 (d, 2.1H, CH(OR)CHHOR), 4.45-3.94 (m, 232.8H, OCH$_2$CHCH$_3$), 1.49-1.22 (m, 318.5H, CH(CH$_3$)O), 1.22-1.0 (m, 14.9H, CH(CH$_3$)OH). A $^1$H NMR spectrum of 4-arm star poly (propylene maleate) of a total DP120 with a meso-erythritol core is shown in FIG. 23 (top). The degree of polymerization and the resulting molecular weight ($\overline{M_n}$) were confirmed by $^1$H NMR calculations. The dispersity ($Đ_m$) was determined by size exclusion chromatography (SEC), the trace is shown in FIG. 24. The results are reported on Table 2, below.

TABLE 2

Molecular characteristics of 4-arm star-shaped PPM.

| Copolymer | Target DP | MAn Conversion (%) | DP ($^1$H NMR) | $\overline{M_n}$ $^1$H NMR (g · mol$^{-1}$) | $Đ_m$ |
|---|---|---|---|---|---|
| Example 1 | 20 (4 × 5) | 99 | 21 | 3,400 | 1.45 |
| Example 2 | 40 (4 × 10) | 95 | 40 | 6,300 | 1.44 |
| Example 3 | 80 (4 × 20) | 99 | 82 | 12,900 | 1.48 |
| Example 4 | 120 (4 × 30) | 82 | 120 | 18,800 | 1.35 |

Example 5

Synthesis of 5-Arm Star Poly(Propylene Maleate) of a Total DP40 with an Adonitol Core Adonitol (152.15 g·mol$^{-1}$, 116.3 mg, 7.65×10$^{-1}$ mmol), Mg(BHT)$_2$(THF)$_2$ (604.95 g·mol$^{-1}$, 92.5 mg, 1.53×10$^{-1}$ mmol), anhydrous toluene (7.6 mL), MAn (98.06 g·mol$^{-1}$, 3.0 g, 30.6 mmol) and PO (58.08 g·mol$^{-1}$, 2.14 mL, 30.6 mmol) were introduced in a flame-dried schlenk, in this order. The schlenk was sealed with a PTFE plug and removed from the glovebox. The solution was stirred at 80° C. for 48 hrs. The resultant copolymer was recovered by precipitation in diethyl ether and then dried under vacuum to afford a sticky beige powder. Yield: 85%

Figure 25:
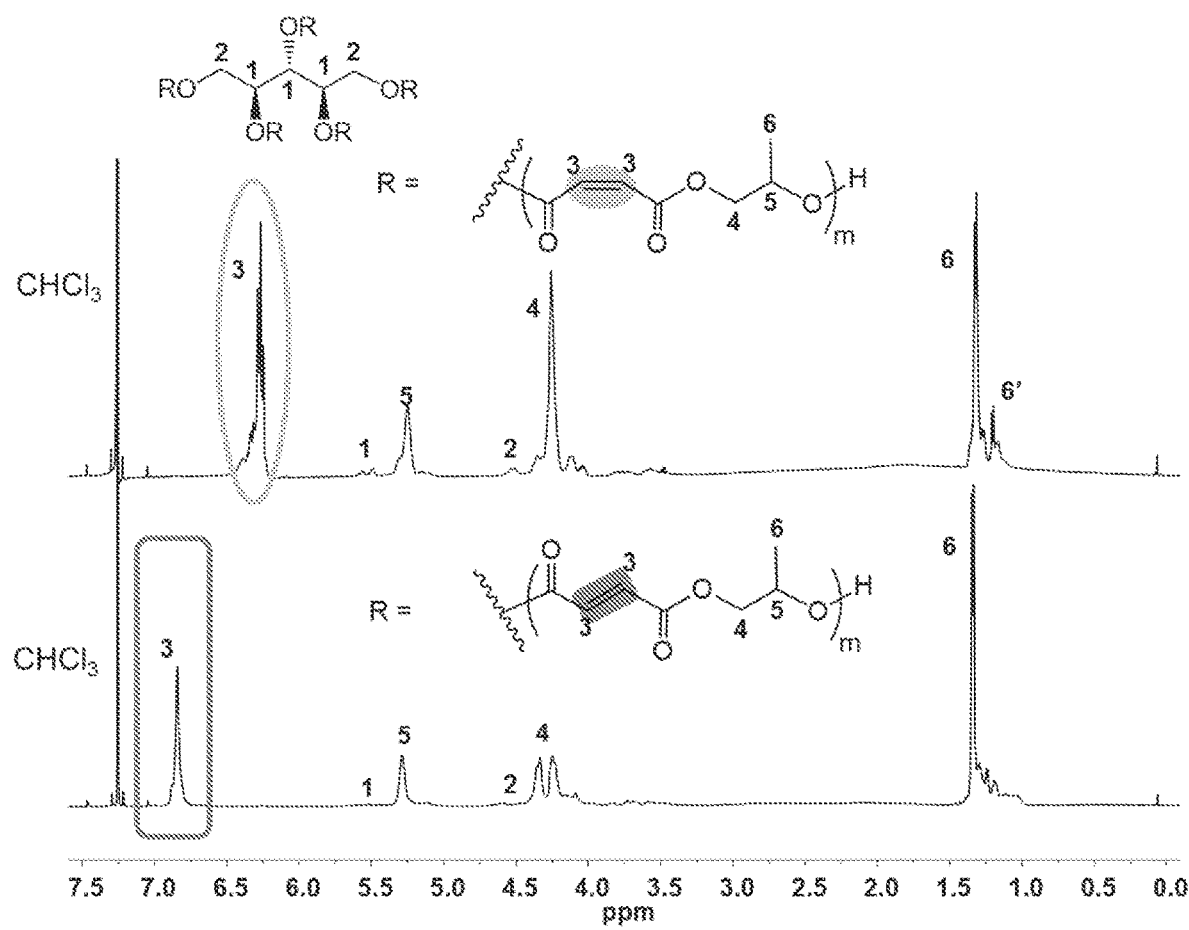
FIG. 25 is a comparison of $^1$H NMR spectra of 5-arm star poly(propylene maleate) of a total DP44 with a adonitol core (top) and corresponding 5-arm star poly(propylene fumarate) obtained after isomerization (bottom).
Figure 26:
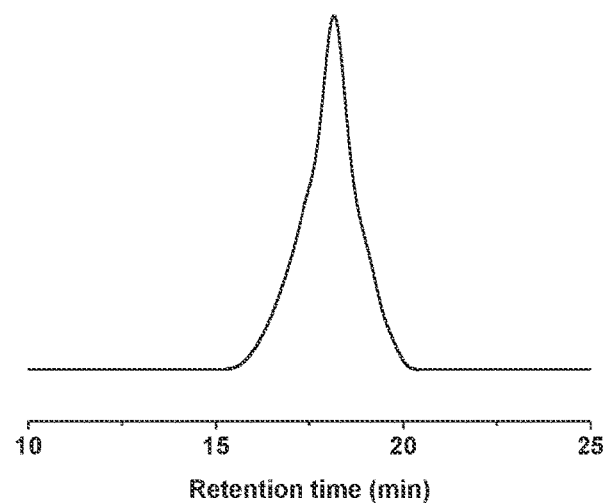
FIG. 26 is the size exclusion chromatography profile of 5-arm star poly(propylene maleate) of a total DP40 with an adonitol core.

The resulting 5-arm star poly(propylene maleate) copolymer was characterized by $^1$H NMR (500 MHz, 298 K, CDCl$_3$): 6.47-6.16 (m, 79.8H, C=OCHCHC=O), 5.64-5.43 (m, 3H, ORCH$_2$CH(OR)CH(OR)CH(OR)CH$_2$OR), 5.40-5.00 (m, 36.7H, CH$_2$CHCH$_3$O), 4.61-4.45 (d, 2.3H, CH(OR)CHHOR), 4.45-3.95 (m, 78.1H, OCH$_2$CHCH$_3$), 1.44-1.22 (m, 119.1H, CH(CH$_3$)O), 1.22-1.0 (m, 14.18H, CH(CH$_3$)OH). A $^1$H NMR spectrum of 5-arm star poly(propylene maleate) of a total DP40 with an adonitol core is shown in FIG. 25 (top). The degree of polymerization and the resulting molecular weight ($\overline{M_n}$) were confirmed by $^1$H NMR calculations. The dispersity ($Đ_m$) was determined by size exclusion chromatography (SEC), the trace is shown in FIG. 26. The results are reported on Table 3, below.

TABLE 3

Molecular characteristics of 5-arm star-shaped PPM.

| Copolymer | Target DP | MAn conversion (%) | DP ($^1$H NMR) | $\overline{M_n}$ $^1$H NMR (g · mol$^{-1}$) | $Đ_m$ |
|---|---|---|---|---|---|
| Example 5 | 40 (5 × 8) | 97 | 44 | 7,000 | 1.72 |

Isomerization of the Star-Shaped PPM into a Star-Shaped PPF

The general procedures for the isomerization reaction are as follows: the multi-arm PPM copolymer was dissolved in chloroform, to reach a concentration of 0.5 mol·L$^{-1}$ of MAn residues. Diethylamine (DEA) (0.15 eq/MAn residue) was added and the solution was refluxed for 24 hrs under inert atmosphere. The organic layer was washed with 1 M sodium phosphate aqueous solution and the copolymer was recovered by evaporation under vacuum to afford a sticky beige powder.

Example 6

Isomerization of 4-Arm Star PPM of a Total DP20 with a Meso-Erythritol Core into the Corresponding Star-Shaped PPF 6 g of the star-shaped PPM (1.79 mmol, 37.1 mmol of MAn residue) recovered from Example 1 were dissolved in 74 mL of chloroform and 0.58 mL of diethylamine (5.57 mmol) was added to the solution. The solution was heated to reflux under inert atmosphere for 24 hours. The organic solution was then washed with a sodium phosphate aqueous solution, chloroform removed by evaporation under vacuum to afford a sticky beige powder. Yield: 93%.

The resulting copolymer was characterized by $^1$H NMR (500 MHz, 298 K, CDCl$_3$) a $^1$H NMR spectrum of 4-arm star poly(propylene fumarate) of a total DP20 with a meso-erythritol core is shown in FIG. 17 (bottom). $^1$H NMR spectra performed before and after isomerization reaction attests that the 4-arm star PPM of Example 1 was successfully isomerized to form the corresponding 4-arm star PPF by showing a disappearance of the proton resonance signal corresponding to cis-alkene protons ($\delta$=6.2 ppm) and an appearance of the new proton resonance signal corresponding to trans-alkene protons ($\delta$=6.7 ppm).

Example 7

Isomerization of 4-Arm Star PPM of a Total DP40 with a Meso-Erythritol Core into the Corresponding Star-Shaped PPF 4.8 g of the star-shaped PPM (7.62×10$^{-1}$ mmol, 30.5 mmol of MAn residue) recovered from Example 2 were dissolved in 61 mL of chloroform and 0.47 mL of diethylamine (4.57 mmol) was added to the solution. The solution was heated to reflux under inert atmosphere for 24 hours. The organic solution was then washed with an aqueous sodium phosphate solution, and the chloroform removed by evaporation under vacuum to afford a sticky beige powder. Yield: 95%

The resulting copolymer was characterized by $^1$H NMR (500 MHz, 298 K, CDCl$_3$) a $^1$H NMR spectrum of 4-arm star poly(propylene fumarate) of a total DP40 with a meso-erythritol core is shown in FIG. 19 (bottom). $^1$H NMR spectra performed before and after isomerization reaction attested that star PPM of Example 2 was successfully isomerized to form the corresponding star PPF by showing the disappearance of the proton resonance signal corresponding to cis-alkene protons ($\delta$=6.2 ppm) and the appearance of the new proton resonance signal corresponding to trans-alkene protons ($\delta$=6.7 ppm).

Example 8

Isomerization of 4-Arm Star PPM of a Total DP80 with a Meso-Erythritol Core into the Corresponding Star-Shaped PPF 5.5 g of the star-shaped PPM (4.26×10$^{-1}$ mmol, 35.0 mmol of MAn residue) recovered from Example 3 were dissolved in 70 mL of chloroform and 0.54 mL of diethylamine (5.24 mmol) was added to the solution. The solution was heated to reflux under inert atmosphere for 24 hours. The organic solution was then washed with a sodium phosphate aqueous solution, chloroform removed by evaporation under vacuum to afford a sticky beige powder. Yield: 91%. The resulting copolymer was characterized by $^1$H NMR (500 MHz, 298 K, CDCl$_3$) a $^1$H NMR spectrum of 4-arm star poly(propylene fumarate) of a total DP80 with a meso-erythritol core is shown in FIG. 21 (bottom). $^1$H NMR spectra performed before and after isomerization reaction attested that star PPM of Example 3 was successfully isomerized into the corresponding star PPF by showing the disappearance of the proton resonance signal corresponding to cis-alkene protons (δ=6.2 ppm) and the appearance of the new proton resonance signal corresponding to trans-alkene protons (δ=6.7 ppm).

Example 9

Isomerization of 4-Arm Star PPM of a Total DP120 with a Meso-Erythritol Core into the Corresponding Star-Shaped PPF 3.5 g of the star-shaped PPM (1.86×10$^{-1}$ mmol, 23.2 mmol of MAn residue) recovered from Example 4 were dissolved in 46 mL of chloroform and 0.36 mL of diethylamine (3.48 mmol) was added to the solution. The solution was heated to reflux under inert atmosphere for 24 hours. The organic solution was then washed with a sodium phosphate aqueous solution, chloroform removed by evaporation under vacuum to afford a sticky beige powder. Yield: 95%

The resulting copolymer was characterized by $^1$H NMR (500 MHz, 298 K, CDCl$_3$), a $^1$H NMR spectrum of 4-arm star poly(propylene fumarate) of a total DP120 with a meso-erythritol core is shown in FIG. 23 (bottom). $^1$H NMR spectra performed before and after isomerization reaction attested that star PPM of Example 5 was successfully isomerized to form the corresponding star PPF by showing the disappearance of the proton resonance signal corresponding to cis-alkene protons (δ=6.2 ppm) and the appearance of the new proton resonance signal corresponding to trans-alkene protons (δ=6.7 ppm).

Example 10

Isomerization of 5-Arm Star PPM of a Total DP40 with an Adonitol Core into the Corresponding Star-Shaped PPF 3.6 g of the star-shaped PPM (5.14×10$^1$ mmol, 23.1 mmol of MAn residue) recovered from Example 5 were dissolved in 46 mL of chloroform and 0.36 mL of diethylamine (3.47 mmol) was added to the solution. The solution was heated to reflux under inert atmosphere for 24 hours. The organic solution was then washed with a sodium phosphate aqueous solution, chloroform removed by evaporation under vacuum to afford a sticky beige powder. Yield: 97%

The resulting copolymer was characterized by $^1$H NMR (500 MHz, 298 K, CDCl$_3$), a $^1$H NMR spectrum of 5-arm star poly(propylene fumarate) of a total DP44 with an adonitol core is shown in FIG. 25 (bottom). $^1$H NMR spectra performed before and after isomerization reaction attested that star PPM of Example 5 was successfully isomerized to the corresponding star PPF by showing the disappearance of the proton resonance signal corresponding to cis-alkene protons (δ=6.2 ppm) and the appearance of the new proton resonance signal corresponding to trans-alkene protons (δ=6.7 ppm).

Preparation of Star-Shape PPF-Based Resin for 3D Printing

As will be apparent to those of skill in the art, the viscosity and therefore the flowability of the fluid polymer resin used is an important variable in certain 3D printing methods. In general, the more viscous (i.e. less flowable) the polymer resin used, the longer it takes to print the 3D object via a photo crosslinking method (e.g., 3D Systems (Rock Hill, S.C.) stereolithography or using a Texas Instruments (Dallas, Tex.) Digital Light Processing™ chip. Flowability of polymeric resins may be increased by heating or by the addition of poorly-toxic solvents, such as DEF. In practice, these methods of reducing viscosity are limited since too much heat can result in autocatalysis of the polymer and a large amount of DEF dramatically reduces the material properties of the resulting 3D printed material.

For linear PPF copolymers, it is generally understood to be preferable to use low molecular weight PPF like a solvent to reduce the viscosity of the blended polymer, and with it the flowability of 3D printing resins made with that PPF polymer. Because of this, it has not been possible to investigate of the influence of higher molecular weights on the mechanical properties of the 3D printed resins. However, because the star-shaped PPF copolymers of the present invention have substantially lower viscosities than their linear counterparts, it has become possible to investigate 3D printable PPF polymers over a much larger range of molecular weights.

Example 11

Complex Viscosity of the PPF:DEF Resins of Examples 6-10

The complex viscosities of the PPF:DEF resins of Examples 6-10 above was measured using the following procedure. 0.80 g of star-shaped PPF copolymer produced in Examples 6-10 were mixed with 0.80 g, 0.53 g and 0.34 g of DEF and heated at 45° C. overnight to prepare respectively 50:50, 60:40 and 70:30 PPF:DEF solutions. After they had cooled down to room temperature, the complex viscosity of the each solution was measured under frequency sweep mode from 0.6 rad·s$^{-1}$ to 630 rad·s$^{-1}$ angular frequency with 10% strain using TA instrument ARES-R2 rheometer with a 50 mm diameter plate.

Figure 27:
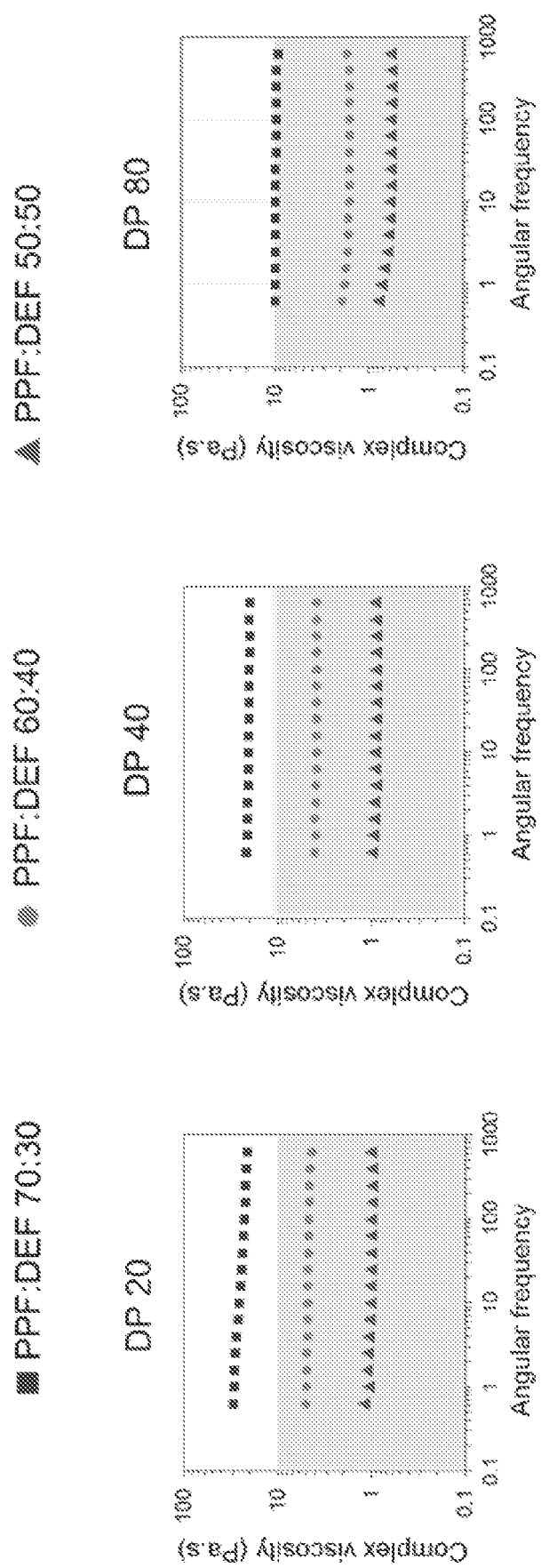
FIG. 27 is a comparison of the complex viscosity of resins versus the angular frequency for PPF:DEF ratios of 70:30, 60:40 and 50:50 and for 4-arm star poly(propylene fumarate) having a meso-erythritol core and total DPs of 20, 40 and 80.
Figure 28:
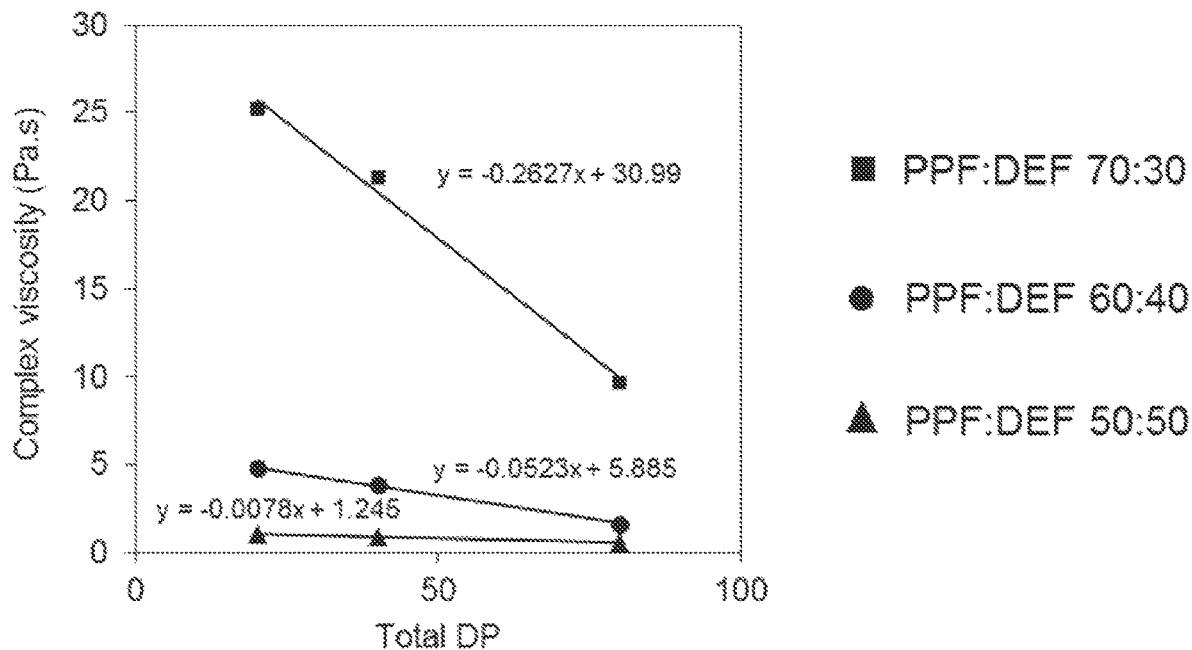
FIG. 28 is a graph plotting the complex viscosity of resins versus the total DP of 4-arm star-shaped PPF.

The complex viscosities at the three various PPF:DEF weight ratios for 4-arm PPF with a meso-erythritol core and total DPs from 20 to 80 are plotted in FIG. 27 and the average values are reported in Table 4, below. Solutions of 4-arm star-shaped PPF having a DP20 have complex viscosities in a 1-25 Pa·s range while solutions of 4-arm star-shaped PPF with a DP80 have complex viscosities in a 0.6-10 Pa·s range. As can be seen, as the DP of the copolymer increases, the complex viscosity of copolymer/DEF solution is reduced, allowing preparation of resin of high molecular weight PPF in a printable viscosity range. Further, the average viscosity of PPF:DEF solutions increased with an increase in the copolymer content of the solution. The average viscosity of the 70% PPF resin with DP from 80 were found to be in the 3D printable range below 10 Pa·s. And as can be seen in FIG. 28, plotting the average complex viscosity values of the resins versus the total DP reveals a high DP-dependence for PPF:DEF 70/30 ratio and allows predictable development of low-viscosity resins, even for low fractions of DEF, by further increasing the DP.

TABLE 4

Average viscosity values of PPF:DEF resins based on 4-arm star-shaped PPF for DP20 to DP80 and a meso-erythritol core.

| Total DP | Average complex viscosity (Pa · s) | | |
|---|---|---|---|
| | PPF:DEF 50:50 | PPF:DEF 60:40 | PPF:DEF 70:30 |
| 20 | 1.10 | 4.78 | 24.90 |
| 40 | 0.98 | 3.89 | 21.30 |
| 80 | 0.63 | 1.67 | 9.71 |

Figure 29:
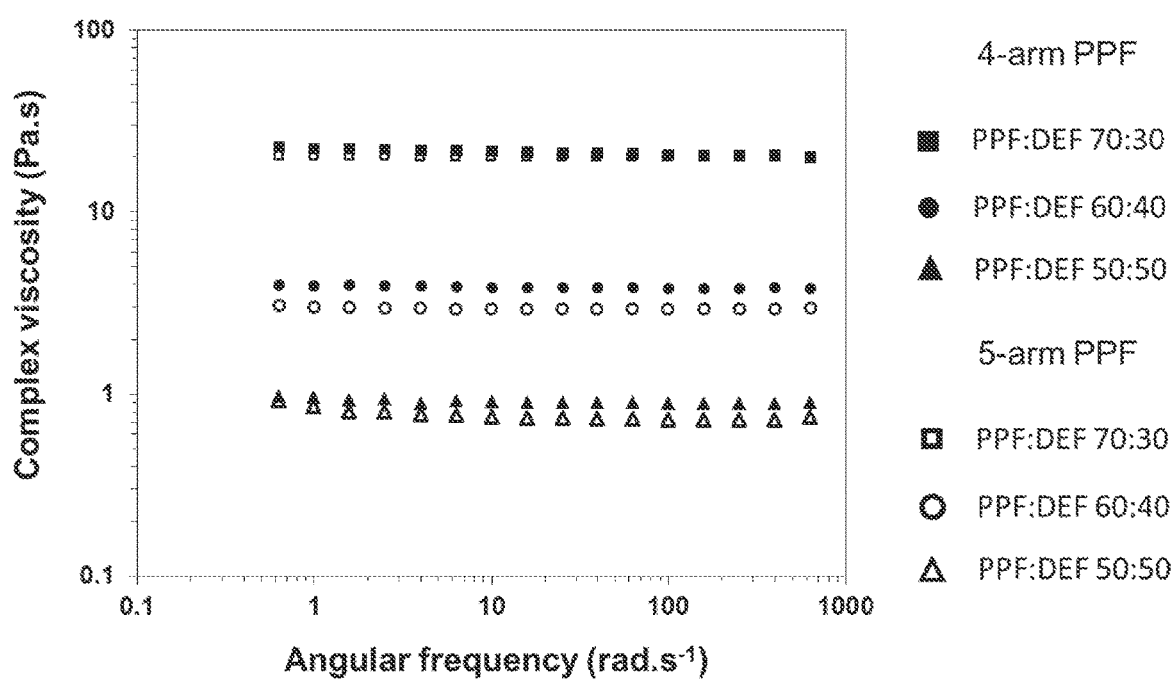
FIG. 29 is a graph plotting the complex viscosity of resin versus the angular frequency for various PPF:DEF ratios (70:30, 60:40 and 50:50) for 4-arm star PPF and 5-arm PPF total DP40

The average complex viscosities at the three various PPF:DEF weight ratios for 5-arm PPF with an adonitol core and total DP40 are shown in Table 5, below. The values range from 0.76 Pa·s for PPF:DEF 50:50 to 20.15 Pa·s for PPF:DEF 70:30 that is below the values obtained for 4-arm PPF with the same DP, as evidence in FIG. 29, demonstrating the correlation between the number of arms and the complex viscosity.

TABLE 5

Average complex viscosity values of PPF:DEF resins based on 5-arm star-shaped PPF for DP40 and an adonitol core.

| Total DP | Average complex viscosity (Pa · s) | | |
|---|---|---|---|
| | PPF:DEF 50:50 | PPF:DEF 60:40 | PPF:DEF 70:30 |
| 40 | 0.76 | 2.96 | 20.15 |

In addition, because the $\overline{M_n}$ and $Đ_m$ of these polymers are predictable and well known, batches with different $\overline{M_n}$ can be blended to get desired viscosity, degradation and/or other characteristics. Batches of star-shaped PPF can also be blended with linear PPF.

In a second set of Experiments (Examples 12-14), four-arm PPF copolymers were synthesized using sugar-based alcohol meso-erythritol as initiator with total DPs in a 20-200 range and their shape evaluated by a combination of $^1$H NMR spectroscopy, size exclusion chromatography (SEC), MALDI-ToF and viscosity measurements. The star PPF polymers were used to prepare PPF:DEF resins with complex viscosities compatible with DLP 3D printing even for high DP values, and used to 3D printing of gyroids scaffolds, which were evaluated.

Materials

All reagents for Examples 12-15 were purchased from Sigma-Aldrich (St. Louis, Mo., USA). All solvents were purchased from Fisher Scientific (Hampton, N.H., USA) and dried using an Innovative Technology Inc. (Newburyport, Mass., USA) Pure Solv MD-3 solvent purification system. $Mg(BHT)_2(THF)_2$ was synthesized as reported previously. See, J. A. Wilson, S. A. Hopkins, P. M. Wright and A. P. Dove, *Polymer Chemistry*, 2014, 5, 2691-2694, the disclosure of which is incorporated herein by reference in its entirety. Meso-erythritol was dried by azeotropic distillation before use. Maleic anhydride was dried under vacuum over $P_2O_5$ for one week. Propylene oxide was dried over calcium hydride overnight prior to vacuum distillation. All other reagents were used as received.

Characterization Techniques for Examples 12-15

Proton ($^1$H) NMR experiments were performed in DMSO-$d_6$ or CDCl$_3$ at 25° C. using a Varian (Palo Alto, Calif., USA) Mercury NMRS 500 spectrometer. All chemical shifts were recorded in parts per million (ppm) relative to the reference peak solvent: DMSO at δ=2.50 ppm and chloroform at δ=7.26 ppm.

The relative number-average molar masses ($\overline{M_n}$) and the molar mass distributions ($Đ_m$) of the copolymers were determined by size exclusion chromatography (SEC) on a Tosoh (Grove City, Ohio, USA) EcoSEC HLC-8320GPC with TSKgel GMHHR-M columns in series. The detector used in this determination was a refractive index detector (RI) and tetrahydrofuran (THF) was used as the eluent flowing at 1.0 mL·min$^{-1}$. The sample concentrations were 10 mg·mL$^{-1}$. Relative $\overline{M_n}$ were calculated using a calibration curve determined from NIST-traceable polystyrene standards.

MALDI-ToF mass spectra were recorded on a Bruker Ultra-Flex III MALDI-ToF/ToF mass spectrometer equipped with a Nd:YAG laser emitting at 355 nm. The instrument was operated in positive ion mode. All samples were dissolved in THF at a final concentration of 10 mg·mL$^{-1}$. Trans-2-[3-(4-tert-butylphenyl)-2-methyl-2-propenylidene]malononitrile (DCTB) (20 mg mL$^{-1}$) served as a matrix and sodium trifluoroacetate (NaTFA) (10 mg·mL$^{-1}$) as cationizing agent. Samples were prepared and mixed in the ratio 10:1. Matrix and sample solutions were applied onto the MALDI-ToF target plate via the sandwich method. FlexAnalysis software was used to analyze MALDI-ToF data.

To confirm the number of arms on the star PPM, the intrinsic viscosities of star-shaped PPM with a degree of polymerization (DP) of 40 were measured in THF using an Ubbelohde viscometer at 35° C. Each sample was prepared in THF and then diluted directly by adding a known volume in the viscometer. The flow time was recorded at each concentration (n=3). The ratios (g') of intrinsic viscosities of the star-shaped PPF to that of linear PPF bearing similar $\overline{M_n}$ were experimentally estimated in accordance with Equation 2:

$$g'=[\eta]_{star}/[\eta]_{linear} \qquad \text{(Equation 2)}$$

where $[\eta]_{star}$ and $[\eta]_{linear}$ are the intrinsic viscosities of star PPF and linear PPF, respectively. For a star-shaped polymer with perfect arm structures, there is a strong relationship of $g^{1/2}=g'$ or $g^{1/2}/g'=1.0$ as proposed by Zimm and Kilb (See, B. H. Zimm and R. W. Kilb, *Journal of Polymer Science*, 1959, 37, 19-42, the disclosure of which is incorporated herein by reference in its entirety). The parameter (g) was defined as the ratio of mean-square radius of gyration ($R_g$) of a star-shaped polymer to that of a linear counterpart with similar $\overline{M_n}$, and could be calculated according to Equation 3, where the parameter f is the number of arms of the star-shaped polymer.

$$g=6f/[(f+1)(f+2)] \qquad \text{(Equation 3)}$$

Complex viscosity ($\eta^*$) of PPF:DEF resins was obtained by using an ARES-G2 rheometer from TA (New Castle, Del., USA) using 50 mm diameter parallel plates with a gap of 0.4 mm. Measurements were performed at 25° C., at 8% stain and at frequencies ranging from 0.1 Hz to 100 Hz (0.6 to 628.3 rad s$^1$). Oscillatory shear measurements were done in the linear response regime.

The scaffolds were imaged using an Olympus Stereoscope (Center Valley, Pa., USA) to depict the gyroid architecture features in greater detail. The structure of the gyroid scaffolds were characterized nondestructively using X-ray micro-computed tomography (t-CT) Skyscan 1172 (Bruker; Billerica, Mass., USA). 3D scanning of scaffolds was carried out using the following parameters: 40 kV voltage, medium camera (pixel size=8.73 µm), no filter, 238 ms camera exposure preset time and 7.0 µm resolution.

Differential scanning calorimetry (DSC) was performed using a DSC-TA Discovery DSC250 (New Castle, Del., USA) scanning a temperature range from −40 to 80° C. with heating and cooling ramps of 10° C.·min$^{-1}$. The glass transition temperature ($T_g$) was determined from the midpoint of the transition in the second heating cycle.

Example 12

Synthesis of Star-Shaped Poly(Propylene Maleate) (PPM)

Four-arm star-shaped poly(propylene maleate) (PPM) copolymers were synthesized by ring-opening copolymerization (ROCOP) of maleic anhydride (MAn) and propylene oxide (PO) using meso-erythritol as an initiator. Various [monomers]/[initiator] molar ratios were used to obtain copolymers with different PPM arm lengths and consequently various degrees of polymerization (DPs). For instance, four-arm star PPM with target a degree of polymerization (DP) 40, was prepared as follows: in a glovebox, meso-erythritol (112.12 g·mol$^{-1}$, 124.5 mg, 1.02 mmol), Mg(BHT)$_2$(THF)$_2$ (604.95 g·mol$^{-1}$, 123.4 mg, 2.04×10$^{-1}$ mmol), anhydrous toluene (10.2 mL), MAn (98.06 g·mol$^{-1}$, 4.0 g, 40.8 mmol) and PO (58.08 g·mol$^{-1}$, 2.85 mL, 40.8 mmol) were introduced, in this order, in a flame-dried Schlenk tube. The Schlenk tube was sealed with a PTFE plug and removed from the glovebox. The solution was stirred at 80° C. for 48 h (typically until the PPM precipitates in the bottom of the Schlenk and the supernatant looked clear). The resultant copolymer was recovered by precipitation in diethyl ether and then dried under vacuum to afford a highly viscous oil (Yield: 78%). The influence of the total monomer concentration (1 M, 2 M, 4 M, 8 M and 14 M) on the monomer conversion was investigated by performing syntheses of star PPM with meso-erythritol as an initiator and total target DPs of 20, 40, 80, 120 and 200. Moreover, the influence of the total monomer concentration on the copolymerization process was investigated by performing kinetic studies at 2 M, 4 M and 8 M, with meso-erythritol as an initiator and total target DP 40. The initial mixture was split in several vials, immersed in a preheated bath at 80° C. (corresponding to the time zero of the reaction), copolymerizations were conducted under stirring and stopped by quenching to ambient temperature and adding an excess of chloroform. The monomer conversions were determined by $^1$H NMR in CDCl$_3$ on crude samples from reaction volumes. For comparison, the kinetics of copolymerization using propargyl alcohol as monofunctional initiator were investigated for monomer concentrations of 8 M and target total DPs of 10 and 40.

Example 13

Isomerization of PPM

The copolymer was dissolved in chloroform at a concentration of 0.5 mol·L$^{-1}$ of MAn residues and diethylamine (DEA) was added to reach 0.15 eq/MAn residue. As an example, four-arm star PPM with target total DP40 were isomerized in the corresponding four-arm star PPF as follows: star-shaped PPM (4.8 g, 7.62×10$^{-1}$ mmol, 30.5 mmol of olefin) was dissolved into chloroform (61 mL, 0.5 mol·L$^{-1}$ of olefin), DEA (0.47 mL, 0.15 mol. eq. olefin) was added and the solution was heated under reflux for 24 h under a nitrogen atmosphere. After cooling to ambient temperature, the organic solution was washed with 1 M sodium phosphate solution (250 mL, pH=6) and the copolymer was recovered after evaporation of the chloroform. Yield: 95%.

Example 14

Resin Preparation

Polymeric resins were prepared by mixing star-shaped PPF with diethyl fumarate (DEF), which acts as both a solvent and crosslinking agent. Various PPF:DEF weigh ratios were investigated, i.e., 70:30, 60:40 and 50:50 wt %. PPF and DEF were carefully introduced in the flask and mixtures were maintained at 45° C. overnight under stirring to insure adequate mixing. In order to print 3D scaffolds, two photoinitiators, phenylbis(2,4,6-trimethylbenzoyl)phosphine oxide (BAPO) and Irgacure 784, and a radical scavenger oxybenzone (HMB) were added to the PPF:DEF solutions at 3%, 0.4% and 0.7% by weight, respectively and mixed evenly throughout the resin, following a previously reported protocol. See, J. P. Fisher, D. Dean and A. G. Mikos, *Biomaterials*, 2002, 23, 4333-4343 and Y. Luo, C. K. Dolder, J. M. Walker, R. Mishra, D. Dean and M. L. Becker, *Biomacromolecules*, 2016, 17, 690-697, the disclosures of which are incorporated herein in their entirety.

Example 15

3D Printing

Gyroid scaffolds with a cylinder shape (8 mm×4 mm) and screws (4.5 mm height) were printed from liquid resins of star PPF of DP200 (PPF:DEF 50:50 wt %) with an EnvisionTEC (Dearborn, Mich., USA) Micro HR 279 printer using a 405 nm LED UV light projector with an irradiance of 225 mW·dm$^{-2}$ and the CAD models were sliced digitally into layers using the Perfactory software suite prior to manufacturing. The Perfactory P3 is an inverted system that projects upward through a transparent glass plate into a reservoir containing the resin. After each projection, the build platform moves vertically upward to allow resin inflow for the next layer. Prior to scaffold printing, cure tests of PPF-based resins were performed to determine the optimal printed layer thickness and UV exposure time depending on the resin formulation. 20 mg of resin were placed in the middle of the resin tray and after irradiation with UV for varying time durations (i.e., 60, 120, 180 and 240 s), the uncured liquid resin was gently removed by tissue paper. The resulting film was peeled off the resin tray with a razor blade and the thickness of the cured film was measured by a digital caliper (Marathon, Ontario, CA) with 10 µm precision. Following these cure tests and printing tests, the layer thickness was fixed to 25 µm and projection time ranged from 60 s to 225 s depending on the PPF molar mass. After printing, scaffolds were immediately rinsed with acetone, 70% ethanol (v/v), and distilled water for 15 s each.

In light of the foregoing, it should be appreciated that the present invention significantly advances the art by providing a star-shaped PPF polymer for 3D printing that is structurally and functionally improved in a number of ways. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

APPENDIX

TABLE 6

Result of rheometry measurement of 70:30 PPF:DEF resin based of 4-arm star-shaped PPF total DP20

| Angular frequency rad·s$^{-1}$ | Step time s | Temp °C. | Oscillation strain % | Oscillation stress Pa | Tan δ | Storage modulus Pa | Loss modulus Pa | Complex viscosity Pa·s |
|---|---|---|---|---|---|---|---|---|
| 0.628319 | 20.0053 | 25.007 | 4.98044 | 0.997712 | 12.3486 | 1.61697 | 19.9672 | 31.8829 |
| 0.995818 | 32.6945 | 25.017 | 4.9795 | 1.5559 | 14.8258 | 2.10278 | 31.1753 | 31.3774 |
| 1.57826 | 40.7173 | 25.009 | 4.98018 | 2.44135 | 16.0773 | 3.04323 | 48.9268 | 31.0603 |
| 2.50138 | 45.8063 | 25.004 | 4.98011 | 3.82005 | 16.0411 | 4.77258 | 76.5576 | 30.6656 |
| 3.96442 | 49.0375 | 25.007 | 4.97765 | 5.97796 | 15.2965 | 7.8345 | 119.84 | 30.2934 |
| 6.28319 | 58.1353 | 25.005 | 4.97993 | 9.32941 | 13.3893 | 13.9529 | 186.82 | 29.8161 |
| 9.95818 | 63.9077 | 25.005 | 4.98392 | 14.5247 | 11.5026 | 25.241 | 290.337 | 29.2656 |
| 15.7826 | 71.2327 | 25.006 | 4.98762 | 22.4924 | 9.70164 | 46.2383 | 448.588 | 28.5734 |
| 25.0138 | 76.657 | 25.01 | 4.99669 | 34.6455 | 8.17381 | 84.2004 | 688.238 | 27.7195 |
| 39.6442 | 82.8925 | 25.003 | 5.00641 | 53.0382 | 6.95166 | 150.843 | 1048.61 | 26.7228 |
| 62.8319 | 90.7717 | 25.01 | 5.0048 | 80.3842 | 6.01076 | 263.588 | 1584.36 | 25.5625 |
| 99.5818 | 96.6888 | 25.008 | 4.95275 | 119.757 | 5.29575 | 448.662 | 2376 | 24.2815 |
| 157.826 | 103.063 | 25.007 | 4.79748 | 173.562 | 4.73818 | 747.079 | 3539.79 | 22.9224 |
| 250.138 | 111.189 | 25.008 | 4.50235 | 243.295 | 4.32734 | 1216.68 | 5264.99 | 21.603 |
| 396.442 | 117.257 | 25.014 | 4.03484 | 323.039 | 3.88541 | 1995.56 | 7753.55 | 20.1952 |
| 628.319 | 124.338 | 25.009 | 3.41457 | 388.928 | 3.38295 | 3228.85 | 10923 | 18.1282 |

TABLE 7

Result of rheometry measurement of 60:40 PPF:DEF resin based of 4-arm star-shaped PPF total DP20

| Angular frequency rad·s$^{-1}$ | Step time s | Temp °C. | Oscillation strain % | Oscillation stress Pa | Tan δ | Storage modulus Pa | Loss modulus Pa | Complex viscosity Pa·s |
|---|---|---|---|---|---|---|---|---|
| 0.628319 | 20.0055 | 24.999 | 4.98097 | 0.158679 | 13.7229 | 0.231532 | 3.17728 | 5.07021 |
| 0.995818 | 32.6947 | 24.996 | 4.97942 | 0.247576 | 18.4597 | 0.268948 | 4.96469 | 4.99286 |
| 1.57826 | 40.7175 | 24.997 | 4.98091 | 0.389952 | 24.2052 | 0.323164 | 7.82227 | 4.96047 |
| 2.50138 | 45.8067 | 24.997 | 4.9803 | 0.614772 | 25.2413 | 0.488659 | 12.3344 | 4.9349 |
| 3.96442 | 49.039 | 24.997 | 4.97621 | 0.966226 | 36.6461 | 0.529652 | 19.4097 | 4.8978 |
| 6.28319 | 58.1362 | 25 | 4.9793 | 1.53191 | 37.661 | 0.816619 | 30.7547 | 4.89649 |
| 9.95818 | 63.9078 | 25.006 | 4.98096 | 2.41231 | 48.1853 | 1.00488 | 48.4203 | 4.86341 |
| 15.7826 | 71.2315 | 24.999 | 4.98003 | 3.81251 | 47.7727 | 1.60215 | 76.5391 | 4.85064 |
| 25.0138 | 76.6563 | 24.998 | 4.98107 | 6.02326 | 43.094 | 2.80528 | 120.891 | 4.83425 |
| 39.6442 | 82.8925 | 24.998 | 4.97801 | 9.49791 | 36.5326 | 5.22071 | 190.726 | 4.81275 |
| 62.8319 | 90.7718 | 25 | 4.96539 | 14.9344 | 28.7566 | 10.4528 | 300.587 | 4.78689 |
| 99.5818 | 96.6897 | 24.999 | 4.92381 | 23.2914 | 22.1589 | 21.3257 | 472.554 | 4.75022 |
| 157.826 | 103.063 | 24.997 | 4.82693 | 35.7541 | 17.2766 | 42.8027 | 739.484 | 4.69327 |
| 250.138 | 111.191 | 24.998 | 4.65003 | 53.7424 | 13.8238 | 83.3871 | 1152.73 | 4.62042 |
| 396.442 | 117.258 | 24.999 | 4.38394 | 79.1724 | 12.1477 | 148.166 | 1799.88 | 4.55543 |
| 628.319 | 124.342 | 25 | 3.9999 | 109.741 | 8.85075 | 308.024 | 2726.24 | 4.36656 |

TABLE 8

Result of rheometry measurement of 50:50 PPF:DEF resin based of 4-arm star-shaped PPF total DP20

| Angular frequency rad·s$^{-1}$ | Step time s | Temp °C. | Oscillation strain % | Oscillation stress Pa | Tan δ | Storage modulus Pa | Loss modulus Pa | Complex viscosity Pa·s |
|---|---|---|---|---|---|---|---|---|
| 0.628319 | 20.0055 | 24.998 | 4.98118 | 0.037881 | 12.4396 | 0.060937 | 0.758026 | 1.21033 |
| 0.995818 | 32.6948 | 25.003 | 4.9801 | 0.053834 | 9.95883 | 0.108002 | 1.07557 | 1.08552 |
| 1.57826 | 40.7157 | 25.001 | 4.98026 | 0.089181 | 13.6286 | 0.13104 | 1.78589 | 1.1346 |
| 2.50138 | 48.3168 | 25.003 | 4.98056 | 0.139413 | 16.3987 | 0.170376 | 2.79394 | 1.11903 |
| 3.96442 | 51.5447 | 24.993 | 4.97556 | 0.215148 | 18.2051 | 0.237164 | 4.31759 | 1.09073 |
| 6.28319 | 62.6393 | 24.997 | 4.9793 | 0.330594 | 21.7187 | 0.305374 | 6.63234 | 1.05669 |
| 9.95818 | 68.4048 | 25.001 | 4.98066 | 0.523024 | 24.8339 | 0.422511 | 10.4926 | 1.05452 |

TABLE 8-continued

Result of rheometry measurement of 50:50 PPF:DEF resin based of 4-arm star-shaped PPF total DP20

| Angular frequency rad · s$^{-1}$ | Step time s | Temp ° C. | Oscillation strain % | Oscillation stress Pa | Tan δ | Storage modulus Pa | Loss modulus Pa | Complex viscosity Pa · s |
|---|---|---|---|---|---|---|---|---|
| 15.7826 | 75.7262 | 24.998 | 4.97782 | 0.815855 | 27.9652 | 0.585706 | 16.3794 | 1.03847 |
| 25.0138 | 81.1482 | 24.995 | 4.97619 | 1.27843 | 33.6041 | 0.76418 | 25.6796 | 1.02707 |
| 39.6442 | 87.3825 | 24.997 | 4.96851 | 2.01181 | 37.0063 | 1.09377 | 40.4765 | 1.02137 |
| 62.8319 | 95.261 | 24.997 | 4.95101 | 3.16434 | 42.6607 | 1.49776 | 63.8954 | 1.01721 |
| 99.5818 | 101.177 | 24.997 | 4.9075 | 4.94856 | 48.9839 | 2.05814 | 100.816 | 1.0126 |
| 157.826 | 109.382 | 25.002 | 4.81798 | 7.66916 | 48.8236 | 3.25959 | 159.145 | 1.00857 |
| 250.138 | 117.511 | 24.997 | 4.67268 | 11.7487 | 46.2521 | 5.43494 | 251.377 | 1.00519 |
| 396.442 | 123.579 | 24.997 | 4.48668 | 17.8441 | 85.4375 | 4.65474 | 397.69 | 1.00322 |
| 628.319 | 130.662 | 24.997 | 4.24884 | 27.0853 | 37.3251 | 17.0733 | 637.263 | 1.0146 |

TABLE 9

Result of rheometry measurement of 70:30 PPF:DEF resin based of 4-arm star-shaped PPF total DP40

| Angular frequency rad · s$^{-1}$ | Step time s | Temp ° C. | Oscillation strain % | Oscillation stress Pa | Tan δ | Storage modulus Pa | Loss modulus Pa | Complex viscosity Pa · s |
|---|---|---|---|---|---|---|---|---|
| 0.628319 | 20.0053 | 24.994 | 4.98038 | 0.711185 | 21.3878 | 0.66693 | 14.2642 | 22.7269 |
| 0.995818 | 32.6945 | 25.001 | 4.97967 | 1.11261 | 24.1919 | 0.922784 | 22.3239 | 22.4368 |
| 1.57826 | 44.6965 | 25 | 4.98057 | 1.74771 | 28.0174 | 1.25165 | 35.0681 | 22.2336 |
| 2.50138 | 52.2965 | 24.996 | 4.98062 | 2.74819 | 29.964 | 1.84044 | 55.147 | 22.0589 |
| 3.96442 | 55.5222 | 25.001 | 4.97738 | 4.31617 | 30.4014 | 2.85082 | 86.6689 | 21.8735 |
| 6.28319 | 64.6162 | 24.999 | 4.97963 | 6.78973 | 32.4098 | 4.20507 | 136.285 | 21.7008 |
| 9.95818 | 70.3867 | 24.994 | 4.98418 | 10.6832 | 32.8373 | 6.52437 | 214.242 | 21.5242 |
| 15.7826 | 83.2845 | 24.997 | 4.98756 | 16.8124 | 32.457 | 10.3808 | 336.928 | 21.3581 |
| 25.0138 | 88.7028 | 24.996 | 4.99607 | 26.4729 | 31.8058 | 16.6514 | 529.613 | 21.1833 |
| 39.6442 | 94.9338 | 24.999 | 5.01101 | 41.705 | 30.9725 | 26.8572 | 831.834 | 20.9934 |
| 62.8319 | 103.911 | 24.993 | 5.01875 | 65.6126 | 30.5301 | 42.7986 | 1306.65 | 20.8071 |
| 99.5818 | 109.755 | 24.997 | 4.9912 | 102.505 | 30.0604 | 68.2816 | 2052.57 | 20.6233 |
| 157.826 | 116.126 | 24.998 | 4.86779 | 157.334 | 29.0554 | 111.175 | 3230.24 | 20.4792 |
| 250.138 | 124.225 | 25.001 | 4.5905 | 234.773 | 27.8356 | 183.615 | 5111.03 | 20.446 |
| 396.442 | 130.318 | 24.999 | 4.07418 | 329.323 | 20.1382 | 400.892 | 8073.23 | 20.3893 |
| 628.319 | 137.395 | 25.006 | 3.24963 | 407.45 | 10.9518 | 1140.12 | 12486.4 | 19.9554 |

TABLE 10

Result of rheometry measurement of 60:40 PPF:DEF resin based of 4-arm star-shaped PPF total DP40

| Angular frequency rad · s$^{-1}$ | Step time s | Temp ° C. | Oscillation strain % | Oscillation stress Pa | Tanδ | Storage modulus Pa | Loss modulus Pa | Complex viscosity Pa · s |
|---|---|---|---|---|---|---|---|---|
| 0.628319 | 30.0053 | 24.993 | 4.98209 | 0.125762 | 24.905 | 0.101275 | 2.52225 | 4.01752 |
| 0.995818 | 42.6897 | 24.993 | 4.97929 | 0.196584 | 27.3152 | 0.14444 | 3.9454 | 3.96462 |
| 1.57826 | 50.7107 | 24.996 | 4.98032 | 0.31406 | 57.2466 | 0.110139 | 6.30506 | 3.99554 |
| 2.50138 | 60.8235 | 24.994 | 4.98061 | 0.491104 | 39.3683 | 0.250383 | 9.85715 | 3.94195 |
| 3.96442 | 64.045 | 24.997 | 4.97642 | 0.776408 | 62.6057 | 0.249174 | 15.5998 | 3.93544 |
| 6.28319 | 73.1367 | 24.994 | 4.97896 | 1.21755 | 72.4956 | 0.337284 | 24.4516 | 3.89196 |
| 9.95818 | 81.4288 | 24.997 | 4.9809 | 1.92544 | 87.3879 | 0.442327 | 38.654 | 3.88189 |
| 15.7826 | 91.9462 | 24.999 | 4.97999 | 3.03863 | 107.015 | 0.570144 | 61.0142 | 3.86607 |
| 25.0138 | 98.8732 | 25 | 4.97989 | 4.81093 | 122.921 | 0.785905 | 96.6039 | 3.86215 |
| 39.6442 | 105.572 | 24.993 | 4.97581 | 7.6044 | 128.701 | 1.18742 | 152.823 | 3.85497 |
| 62.8319 | 113.457 | 25.001 | 4.96296 | 11.9993 | 159.058 | 1.52003 | 241.773 | 3.84801 |
| 99.5818 | 119.376 | 24.998 | 4.92301 | 18.8336 | 188.635 | 2.02803 | 382.557 | 3.84169 |
| 157.826 | 125.752 | 25.003 | 4.83027 | 29.2714 | 317.862 | 1.90648 | 605.997 | 3.83966 |
| 250.138 | 133.881 | 24.997 | 4.66331 | 44.8382 | −16436.4 | −0.0585 | 961.511 | 3.84392 |
| 396.442 | 139.949 | 24.993 | 4.41676 | 67.9622 | −95.0479 | −16.1881 | 1538.65 | 3.88136 |
| 678.319 | 147.033 | 24.997 | 4.04769 | 97.5835 | 5234.27 | 0.46059 | 2410.85 | 3.83698 |

TABLE 11

Result of rheometry measurement of 50:50 PPF:DEF resin based of 4-arm star-shaped PPF total DP40

| Angular frequency rad · s$^{-1}$ | Step time s | Temp ° C. | Oscillation strain % | Oscillation stress Pa | Tan δ | Storage modulus Pa | Loss modulus Pa | Complex viscosity Pa · s |
|---|---|---|---|---|---|---|---|---|
| 0.628319 | 20.0053 | 24.998 | 4.98075 | 0.030646 | 7.71957 | 0.079046 | 0.610198 | 0.979275 |
| 0.995818 | 32.6945 | 24.997 | 4.97917 | 0.047773 | 12.4565 | 0.076777 | 0.956376 | 0.963483 |
| 1.57826 | 48.6795 | 24.994 | 4.98095 | 0.073603 | 13.8861 | 0.106139 | 1.47387 | 0.93627 |
| 2.50138 | 56.2762 | 25.003 | 4.98073 | 0.117649 | 19.6836 | 0.119848 | 2.35904 | 0.944311 |
| 3.96442 | 59.5012 | 25 | 4.97644 | 0.177633 | 35.8383 | 0.099561 | 3.56809 | 0.900377 |
| 6.28319 | 68.5948 | 25 | 4.97819 | 0.28815 | 33.1728 | 0.174409 | 5.78563 | 0.921229 |
| 9.95818 | 74.3647 | 24.997 | 4.9804 | 0.453837 | 38.1879 | 0.238541 | 9.10934 | 0.915073 |
| 15.7826 | 81.6872 | 25 | 4.97907 | 0.713814 | 46.4548 | 0.308536 | 14.333 | 0.908358 |
| 25.0138 | 87.1108 | 25.001 | 4.97727 | 1.12522 | 58.5181 | 0.386272 | 22.6039 | 0.90379 |
| 39.6442 | 93.3462 | 24.998 | 4.9703 | 1.77676 | 79.0727 | 0.452049 | 35.7447 | 0.901709 |
| 62.8319 | 101.223 | 24.994 | 4.95252 | 2.804 | 93.8816 | 0.603039 | 56.6143 | 0.901096 |
| 99.5818 | 107.142 | 24.998 | 4.91038 | 4.38874 | 94.0976 | 0.949777 | 89.3717 | 0.897521 |
| 157.826 | 113.516 | 24.996 | 4.82111 | 6.82405 | 213.963 | 0.661533 | 141.543 | 0.896839 |
| 250.138 | 121.641 | 24.996 | 4.67957 | 10.4774 | −1270.74 | −0.1762 | 223.897 | 0.895094 |
| 396.442 | 127.71 | 24.997 | 4.49686 | 16.0521 | −55.6445 | −6.41403 | 356.906 | 0.900417 |
| 628.319 | 134.787 | 24.997 | 4.26858 | 24.3751 | −90.2358 | −6.3279 | 571.003 | 0.908836 |

TABLE 12

Result of rheometry measurement of 70:30 PPF:DEF resin based of 4-arm star-shaped PPF total DP80

| Angular frequency rad · s$^{-1}$ | Step time s | Temp ° C. | Oscillation strain % | Oscillation stress Pa | Tan δ | Storage modulus Pa | Loss modulus Pa | Complex viscosity Pa · s |
|---|---|---|---|---|---|---|---|---|
| 0.628319 | 20.0053 | 24.989 | 7.96988 | 0.496498 | 67.0551 | 0.092893 | 6.22898 | 9.91484 |
| 0.995818 | 32.6945 | 24.993 | 7.96748 | 0.786286 | 55.8367 | 0.176714 | 9.8671 | 9.91013 |
| 1.57826 | 40.7155 | 24.993 | 7.96973 | 1.24481 | 73.444 | 0.212649 | 15.6178 | 9.89649 |
| 2.50138 | 45.8048 | 24.995 | 7.96769 | 1.96916 | 79.8922 | 0.309322 | 24.7124 | 9.88028 |
| 3.96442 | 50.622 | 24.994 | 7.96301 | 3.11002 | 80.5528 | 0.484809 | 39.0528 | 9.85157 |
| 6.28319 | 61.7187 | 25.001 | 7.96776 | 4.92609 | 75.7224 | 0.816402 | 61.8199 | 9.8398 |
| 9.95818 | 67.4852 | 25.001 | 7.9723 | 7.79278 | 71.0192 | 1.37623 | 97.7386 | 9.81588 |
| 15.7826 | 74.8072 | 24.995 | 7.97269 | 12.3129 | 66.5171 | 2.32152 | 154.422 | 9.78537 |
| 25.0138 | 80.2298 | 24.997 | 7.97869 | 19.4651 | 62.3901 | 3.90979 | 243.932 | 9.75316 |
| 39.6442 | 86.4647 | 24.99 | 7.98621 | 30.7689 | 57.2967 | 6.72319 | 385.217 | 9.71833 |
| 62.8319 | 94.3447 | 24.992 | 7.98081 | 48.5754 | 51.6562 | 11.7806 | 608.539 | 9.68701 |
| 99.5818 | 100.26 | 24.999 | 7.92219 | 76.1801 | 45.0286 | 21.3501 | 961.367 | 9.65642 |
| 157.826 | 106.633 | 24.991 | 7.75708 | 117.801 | 36.3387 | 41.7751 | 1518.06 | 9.62215 |
| 250.138 | 114.762 | 24.992 | 7.41389 | 177.367 | 26.7389 | 89.4086 | 2390.69 | 9.56416 |
| 396.442 | 120.828 | 24.991 | 6.80412 | 257.354 | 20.6252 | 183.169 | 3777.89 | 9.54068 |
| 628.319 | 127.913 | 24.993 | 5.80904 | 333.771 | 12.174 | 470.383 | 5726.42 | 9.14458 |

TABLE 13

Result of rheometry measurement of 60:40 PPF:DEF resin based of 4-arm star-shaped PPF total DP80

| Angular frequency rad · s$^{-1}$ | Step time s | Temp ° C. | Oscillation strain % | Oscillation stress Pa | Tan δ | Storage modulus Pa | Loss modulus Pa | Complex viscosity Pa · s |
|---|---|---|---|---|---|---|---|---|
| 0.628319 | 20.0053 | 25.184 | 7.98569 | 0.097223 | 4.97873 | 0.239745 | 1.19363 | 1.93766 |
| 0.995818 | 32.6945 | 25.184 | 7.96773 | 0.143416 | 9.75623 | 0.183532 | 1.79058 | 1.80752 |
| 1.57826 | 40.7175 | 25.179 | 7.9706 | 0.221271 | 14.278 | 0.193957 | 2.76764 | 1.75895 |
| 2.50138 | 45.8067 | 25.175 | 7.96898 | 0.33823 | 18.9953 | 0.223133 | 4.23847 | 1.6968 |
| 3.96442 | 49.039 | 25.164 | 7.9607 | 0.526832 | 30.4672 | 0.217097 | 6.61434 | 1.66932 |
| 6.28319 | 58.1362 | 25.137 | 7.96364 | 0.827221 | 39.0461 | 0.265944 | 10.3841 | 1.65322 |
| 9.95818 | 65.17 | 25.11 | 7.96742 | 1.29715 | 51.7902 | 0.3143 | 16.2777 | 1.63491 |
| 15.7826 | 72.4985 | 25.088 | 7.96352 | 2.04755 | 63.2369 | 0.406542 | 25.7084 | 1.62911 |
| 25.0138 | 78.4283 | 25.072 | 7.96299 | 3.23256 | 81.1907 | 0.499956 | 40.5918 | 1.6229 |
| 39.6442 | 85.9178 | 25.051 | 7.95211 | 5.10614 | 91.5245 | 0.701532 | 64.2073 | 1.61968 |
| 62.8319 | 93.8077 | 25.033 | 7.92341 | 8.04886 | 105.328 | 0.964408 | 101.579 | 1.61675 |
| 99.5818 | 99.6528 | 25.024 | 7.85706 | 12.6091 | 144.453 | 1.11093 | 160.477 | 1.61155 |
| 157.826 | 106.024 | 25.015 | 7.71327 | 19.6286 | 155.349 | 1.63807 | 254.473 | 1.61239 |

TABLE 13-continued

Result of rheometry measurement of 60:40 PPF:DEF resin based of 4-arm star-shaped PPF total DP80

| Angular frequency rad · s$^{-1}$ | Step time s | Temp °C. | Oscillation strain % | Oscillation stress Pa | Tan δ | Storage modulus Pa | Loss modulus Pa | Complex viscosity Pa · s |
| --- | --- | --- | --- | --- | --- | --- | --- | --- |
| 250.138 | 114.122 | 25.003 | 7.47699 | 30.1755 | 844.295 | 0.478025 | 403.579 | 1.61343 |
| 396.442 | 120.166 | 24.999 | 7.16963 | 45.8178 | −57.0532 | −11.1994 | 638.959 | 1.61198 |
| 628.319 | 127.24 | 24.994 | 6.74922 | 71.3388 | −534.531 | −1.97743 | 1057 | 1.68227 |

TABLE 14

Result of rheometry measurement of 50:50 PPF:DEF resin based of 4-arm star-shaped PPF total DP80

| Angular frequency rad · s$^{-1}$ | Step time s | Temp °C. | Oscillation strain % | Oscillation stress Pa | Tan δ | Storage modulus Pa | Loss modulus Pa | Complex viscosity Pa · s |
| --- | --- | --- | --- | --- | --- | --- | --- | --- |
| 0.628319 | 20.0055 | 24.994 | 7.96973 | 0.039736 | 3.13596 | 0.151475 | 0.475019 | 0.793524 |
| 0.995818 | 32.6945 | 24.999 | 7.96677 | 0.059634 | 3.25986 | 0.219523 | 0.715615 | 0.751672 |
| 1.57826 | 40.7173 | 24.997 | 7.96878 | 0.087508 | 8.04462 | 0.135463 | 1.08975 | 0.695785 |
| 2.50138 | 45.8067 | 24.997 | 7.96837 | 0.127643 | 8.95749 | 0.177726 | 1.59198 | 0.640393 |
| 3.96442 | 49.039 | 24.997 | 7.96265 | 0.198064 | 15.1641 | 0.163677 | 2.48202 | 0.627433 |
| 6.28319 | 58.1363 | 25 | 7.96654 | 0.307516 | 18.3279 | 0.2103 | 3.85436 | 0.614353 |
| 9.95818 | 63.9078 | 25.001 | 7.96733 | 0.482796 | 26.2179 | 0.23096 | 6.05529 | 0.608514 |
| 15.7826 | 71.2322 | 25.001 | 7.96586 | 0.755326 | 40.7699 | 0.232505 | 9.47919 | 0.600789 |
| 25.0138 | 76.6567 | 25 | 7.96086 | 1.19087 | 46.4209 | 0.322173 | 14.9556 | 0.598032 |
| 39.6442 | 83.3673 | 24.997 | 7.94917 | 1.87683 | 60.3482 | 0.391182 | 23.6071 | 0.595557 |
| 62.8319 | 91.6575 | 25.003 | 7.91952 | 2.95083 | 81.3419 | 0.458035 | 37.2574 | 0.593015 |
| 99.5818 | 98.3892 | 24.994 | 7.84804 | 4.61048 | 153.056 | 0.383819 | 58.7458 | 0.589937 |
| 157.826 | 105.713 | 24.998 | 7.70421 | 7.15099 | 155.799 | 0.595752 | 92.8177 | 0.588112 |
| 250.138 | 113.838 | 24.997 | 7.46396 | 10.9484 | 374.413 | 0.391773 | 146.685 | 0.586419 |
| 396.442 | 119.908 | 24.997 | 7.14744 | 16.3275 | −36.7049 | −6.22153 | 228.36 | 0.576238 |
| 628.319 | 126.982 | 25.001 | 6.69777 | 24.9496 | 64.247 | 5.7977 | 372.485 | 0.592899 |

TABLE 15

Result of rheometry measurement of 70:30 PPF:DEF resin based on 5-arm star-shaped PPF total DP40

| Angular frequency rad · s$^{-1}$ | Step time s | Temp °C. | Oscillation strain % | Oscillation stress Pa | Tan δ | Storage modulus Pa | Loss modulus Pa | Complex viscosity Pa · s |
| --- | --- | --- | --- | --- | --- | --- | --- | --- |
| 0.628319 | 20.0053 | 25.246 | 7.98898 | 1.01622 | 51.0928 | 0.248916 | 12.7178 | 20.2449 |
| 0.995818 | 32.6943 | 25.21 | 7.96512 | 1.60244 | 69.1496 | 0.290907 | 20.1161 | 20.2027 |
| 1.57826 | 40.7173 | 25.183 | 7.96786 | 2.54431 | 60.7087 | 0.525919 | 31.9279 | 20.2325 |
| 2.50138 | 45.8065 | 25.161 | 7.96723 | 4.02539 | 53.6954 | 0.94078 | 50.5156 | 20.1986 |
| 3.96442 | 49.0388 | 25.144 | 7.96266 | 6.36925 | 52.0765 | 1.53571 | 79.9743 | 20.1767 |
| 6.28319 | 58.136 | 25.112 | 7.96596 | 10.0614 | 52.3313 | 2.41313 | 126.282 | 20.1021 |
| 9.95818 | 63.9082 | 25.095 | 7.97388 | 15.9232 | 55.0255 | 3.62847 | 199.659 | 20.053 |
| 15.7826 | 71.233 | 25.066 | 7.98158 | 25.2292 | 60.5933 | 5.21592 | 316.05 | 20.0279 |
| 25.0138 | 76.6572 | 25.056 | 7.99906 | 40.059 | 63.7338 | 7.85666 | 500.735 | 20.0208 |
| 39.6442 | 86.6963 | 25.033 | 8.02984 | 63.8014 | 63.3889 | 12.533 | 794.454 | 20.0421 |
| 62.8319 | 96.5838 | 25.017 | 8.05576 | 101.501 | 62.0669 | 20.2978 | 1259.82 | 20.0533 |
| 99.5818 | 105.531 | 25.008 | 8.02114 | 160.334 | 58.2985 | 34.2821 | 1998.59 | 20.0728 |
| 157.826 | 116.237 | 24.997 | 7.82024 | 249.136 | 58.577 | 54.3784 | 3185.32 | 20.1854 |
| 250.138 | 125.658 | 24.988 | 7.32764 | 371.535 | 46.5539 | 108.888 | 5069.15 | 20.2701 |
| 396.442 | 131.731 | 24.986 | 6.3729 | 517.353 | 27.7217 | 292.65 | 8112.74 | 20.4772 |
| 628.319 | 138.814 | 24.989 | 4.91623 | 619.053 | 10.9458 | 1145.63 | 12539.8 | 20.0408 |

TABLE 16

Result of rheometry measurement of 60:40 PPF:DEF resin based on 5-arm star-shaped PPF total DP40

| Angular frequency rad·s⁻¹ | Step time s | Temp °C. | Oscillation strain % | Oscillation stress Pa | Tanδ | Storage modulus Pa | Loss modulus Pa | Complex viscosity Pa·s |
|---|---|---|---|---|---|---|---|---|
| 0.628319 | 20.0055 | 25.137 | 8.01008 | 0.154419 | 33.7093 | 0.057164 | 1.92696 | 3.0682 |
| 0.995818 | 32.6947 | 25.181 | 7.97311 | 0.238207 | 50.8241 | 0.058772 | 2.98705 | 3.00018 |
| 1.57826 | 40.7157 | 25.17 | 7.96863 | 0.376937 | 54.8779 | 0.086182 | 4.72947 | 2.99712 |
| 2.50138 | 45.8048 | 25.166 | 7.96879 | 0.595445 | 52.7308 | 0.141679 | 7.47087 | 2.98723 |
| 3.96442 | 49.0373 | 25.163 | 7.96228 | 0.939347 | 58.9144 | 0.200219 | 11.7958 | 2.97583 |
| 6.28319 | 58.1345 | 25.143 | 7.96521 | 1.47777 | 65.8724 | 0.281616 | 18.5507 | 2.95277 |
| 9.95818 | 63.9065 | 25.123 | 7.96788 | 2.33714 | 74.4652 | 0.393866 | 29.3293 | 2.94552 |
| 15.7826 | 71.232 | 25.104 | 7.96635 | 3.70054 | 90.7 | 0.51212 | 46.4493 | 2.94324 |
| 25.0138 | 76.9077 | 25.088 | 7.96473 | 5.85182 | 109.217 | 0.672684 | 73.4686 | 2.93724 |
| 39.6442 | 83.303 | 25.073 | 7.9577 | 9.25235 | 123.572 | 0.940868 | 116.265 | 2.93282 |
| 62.8319 | 91.1813 | 25.048 | 7.93391 | 14.6112 | 147.517 | 1.24838 | 184.157 | 2.93101 |
| 99.5818 | 97.0978 | 25.034 | 7.87007 | 22.9715 | 176.501 | 1.6537 | 291.88 | 2.93111 |
| 157.826 | 103.471 | 25.028 | 7.72472 | 35.7238 | 409.587 | 1.12909 | 462.459 | 2.93018 |
| 250.138 | 111.598 | 25.017 | 7.47465 | 54.9072 | −479.64 | −1.53152 | 734.578 | 2.9367 |
| 396.442 | 117.666 | 25.012 | 7.13733 | 83.1836 | −172.103 | −6.77185 | 1165.45 | 2.93983 |
| 628.319 | 124.747 | 25.004 | 6.63306 | 123.946 | −76.9594 | −24.2784 | 1868.45 | 2.97398 |

TABLE 17

Result of rheometry measurement of 50:50 PPF:DEF resin based on a 5-arm star-shaped PPF total DP40

| Angular frequency rad·s⁻¹ | Step time s | Temp °C. | Oscillation strain % | Oscillation stress Pa | Tan δ | Storage modulus Pa | Loss modulus Pa | Complex viscosity Pa·s |
|---|---|---|---|---|---|---|---|---|
| 0.628319 | 20.0053 | 25.206 | 7.9964 | 0.046751 | 8.64552 | 0.067177 | 0.580779 | 0.930501 |
| 0.995818 | 32.6945 | 25.219 | 7.96847 | 0.068028 | 8.82497 | 0.096124 | 0.848289 | 0.857303 |
| 1.57826 | 40.7153 | 25.203 | 7.96792 | 0.100549 | 8.51595 | 0.147173 | 1.25332 | 0.799566 |
| 2.50138 | 45.8047 | 25.192 | 7.96699 | 0.159007 | 13.4441 | 0.148045 | 1.99033 | 0.797891 |
| 3.96442 | 49.037 | 25.18 | 7.96161 | 0.244266 | 11.0857 | 0.275639 | 3.05565 | 0.773897 |
| 6.28319 | 62.134 | 25.134 | 7.96142 | 0.381526 | 16.1596 | 0.295986 | 4.78303 | 0.7627 |
| 9.95818 | 71.0523 | 25.102 | 7.96541 | 0.594923 | 19.3398 | 0.385674 | 7.45887 | 0.75002 |
| 15.7826 | 78.3752 | 25.079 | 7.96419 | 0.930859 | 24.3681 | 0.479243 | 11.6782 | 0.740564 |
| 25.0138 | 86.5612 | 25.061 | 7.96 | 1.46765 | 31.2601 | 0.589518 | 18.4284 | 0.737104 |
| 39.6442 | 92.7927 | 25.044 | 7.94892 | 2.30867 | 40.7772 | 0.712042 | 29.0351 | 0.732612 |
| 62.8319 | 100.688 | 25.018 | 7.91768 | 3.63241 | 54.4369 | 0.842618 | 45.8695 | 0.730159 |
| 99.5818 | 106.596 | 25.016 | 7.84993 | 5.68292 | 81.2528 | 0.890913 | 72.3892 | 0.726987 |
| 157.826 | 112.965 | 25.013 | 7.70758 | 8.83227 | 112.983 | 1.0142 | 114.588 | 0.726065 |
| 250.138 | 121.132 | 25.006 | 7.47884 | 13.5733 | 325.598 | 0.557404 | 181.49 | 0.725561 |
| 396.442 | 127.2 | 24.996 | 7.19139 | 20.7281 | −58.6488 | −4.91393 | 288.196 | 0.727062 |
| 628.319 | 134.282 | 24.988 | 6.82547 | 32.1623 | −112.73 | −4.17996 | 471.205 | 0.749975 |

What is claimed is:

1. A star-shaped copolymer having three or more poly(propylene fumarate) arms extending outward from a central core comprising the residue of a multi-functional alcohol initiator having three or more hydroxyl functional groups, said star-shaped copolymer having the formula:

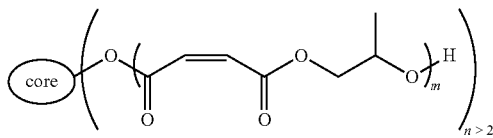

where m is an integer from about 1 to about 200, n is a number of arms greater than 2 and an absorbance at wavelengths from about 305 nm to about 405 nm of from about 0.001 to about 0.3, as measured by a UV-Visible spectrometer.

2. The star-shaped copolymer of claim 1, wherein said each of said three or more poly(propylene fumarate) arms comprise about 50 mole percent propylene oxide residues and 50 mole percent maleic anhydride residues.

3. The star-shaped copolymer of claim 1 having a degree of polymerization (DP) of from about 3 to about 650.

4. The star-shaped copolymer of claim 1 having a number average molecular weight ($\overline{M_n}$) of from about 0.5 kDa to about 100 kDa, as calculated for NMR spectroscopy or measured by one of size exclusion chromatography (SEC) and gel permeation chromatography (GPC).

5. The star-shaped copolymer of claim 1 having a molecular mass distribution ($Đ_m$) of from about 1 to about 2.

6. The star-shaped copolymer of claim 1 having an average complex viscosity of from about 0.2 Pa·s to about 2.0 Pa·s, as measured by a rheometer when diluted in 50 weight percent DEF.

7. The star-shaped copolymer of claim 1 having an average complex viscosity of from about 0.5 Pa·s to about 10.0 Pa·s, as measured by a rheometer when diluted in 40 weight percent DEF.

8. The star-shaped copolymer of claim 1 having an average complex viscosity of from about 2 Pa·s to about 30 Pa·s, as measured by a rheometer when diluted in 30 weight percent DEF.

9. A star-shaped copolymer for use in 3D printable resins comprising the isomerized reaction product of maleic anhydride, propylene oxide, and a multi-functional alcohol initiator having three or more hydroxyl functional groups, said star-shaped poly(propylene fumarate) copolymer having an absorbance at wavelengths from about 305 nm to about 405 nm of from about 0.001 to about 0.2, as measured by a UV-Visible spectrometer.

10. The star-shaped poly(propylene fumarate) copolymer of claim 9 having a degree of polymerization (DP) of from about 3 to about 325.

11. The star-shaped poly(propylene fumarate) copolymer of claim 9 having a number average molecular weight ($\overline{M_n}$) of from about 0.5 kDa to about 50 kDa, as calculated for NMR spectroscopy or measured by size exclusion chromatography (SEC) or gel permeation chromatography (GPC).

12. The star-shaped poly(propylene fumarate) copolymer of claim 9 having a molecular mass distribution ($Ð_m$) of from about 1 to about 1.7.

13. The star-shaped poly(propylene fumarate) copolymer of claim 9 having an average complex viscosity of from about 0.5 Pa·s to about 1.5 Pa·s, as measured by a rheometer when diluted in 50 weight percent DEF.

14. The star-shaped poly(propylene fumarate) copolymer of claim 9 having an average complex viscosity of from about 0.8 Pa·s to about 6 Pa·s, as measured by a rheometer when diluted in 40 weight percent DEF.

15. The star-shaped poly(propylene fumarate) copolymer of claim 9 having an average complex viscosity of from about 5 Pa·s to about 25 Pa·s, as measured by a rheometer when diluted in 30 weight percent DEF.

16. The star-shaped poly(propylene fumarate) copolymer of claim 9 having the formula:

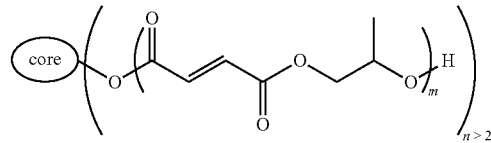

where m is an integer from about 1 to about 200, n is a number of arms greater than 2 and the core comprises the residue of a multi-functional alcohol initiator.

17. A polymer resin for use in 3D printing comprising the star-shaped copolymer of claim 1.

18. The polymer resin of claim 17 wherein the star-shaped copolymer of claim 1 comprises from about 50 wt % to about 70 wt % of said polymer resin.

19. A 3D printed polymer structure comprising the star-shaped copolymer of claim 1.

20. A 3D printed polymer structure comprising the polymer resin of claim 18.

21. The star-shaped copolymer of claim 1 having an absorbance at wavelengths from 305 nm to 405 nm of from 0.001 to 0.2.

22. The star-shaped copolymer of claim 1 having an absorbance at wavelengths from 305 nm to 405 nm of from 0.001 to 0.1.

23. The star-shaped copolymer of claim 9 having an absorbance at wavelengths from 305 nm to 405 nm of from 0.001 to 0.2.

24. The star-shaped copolymer of claim 9 having an absorbance at wavelengths from 305 nm to 405 nm of from 0.001 to 0.1.

* * * * *